United States Patent [19]
Folkman et al.

[11] Patent Number: 5,861,372
[45] Date of Patent: Jan. 19, 1999

[54] AGGREGATE ANGIOSTATIN AND METHOD OF USE

[75] Inventors: M. Judah Folkman, Brookline; Jie Lin, Newton Center; Michael S. O'Reilly, Winchester, all of Mass.

[73] Assignee: The Children's Medical Center Corporation, Boston, Mass.

[21] Appl. No.: 605,598

[22] Filed: Feb. 22, 1996

[51] Int. Cl.⁶ .......................... A61K 38/16; C07K 14/00
[52] U.S. Cl. ................. 514/2; 514/12; 530/350; 530/412; 530/417; 530/422
[58] Field of Search ................... 530/350, 412, 530/417, 422; 514/12, 2

[56] References Cited

U.S. PATENT DOCUMENTS

| | | | |
|---|---|---|---|
| 4,677,196 | 6/1987 | Rausch et al. | 530/412 |
| 4,966,963 | 10/1990 | Patroni | 530/351 |
| 5,288,502 | 2/1994 | McGinity et al. | 424/484 |
| 5,530,100 | 6/1996 | Darling et al. | 530/383 |

FOREIGN PATENT DOCUMENTS

WO 95/29242  11/1995  WIPO.

OTHER PUBLICATIONS

O'Reilly et al. 'Angiostatin:A Novel Antgogenesis Inhibior that Mediates the Suppression of Metastases by Lewis Lung Carcinoma'. Cell, vol. 79, pp. 315–328, Oct. 21, 1994.

Folkman J., Tumor angiogenesis: Therapeutic implications., N. Engl. Jour. Med. 285:11832 1186, 1971.

Algire GH, et al. Vascular reactions of normal and malignant tumors in vivo. I. Vascular reactions of mice to wounds and to normal neoplastic transplants. J. Natl. Cancer Inst. 6:73–85, 1945.

Folkman J, et al., Tumor behavior in isolated perfused organs: In vitro growth and metastasis of biopsy material in rabbit thyroid and canine intestinal segments. Annals of Surgery 164:491–502, 1966.

Gimbrone, M.A., Jr. et al., Tumor growth and neovascularization: An experimental model using the rabbit cornea. J. Natl. Cancer Institute 52:41–427, 1974.

Gimbrone MA Jr., et al., Tumor dormancy in vivo by prevention of neovascularization. J. Exp. Med. 136:261–276.

Knighton D., Avascular and vascular phases of tumor growth in the chick embryo. British J. Cancer, 35:347–356, 1977.

Lien W., et al., The blood supply of experimental liver metastases. II. A microcirculatory study of normal and tumor vessels of the liver with the use of perfused silicone rubber. Surgery 68:334–340, 1970.

Folkman J. et al., Induction of angiogenesis during the transition from hyperplasia to neoplastia. Nature 339:58–61, 1989.

Kim K J, et al., Inhibition of vascular endothelial growth factor–induced angiogenesis suppresses tumor growth in vivo. Nature 362:841–844, 1993.

Hori A, et al., Suppression of solid tumor growth by immunoneutralizing monoclonal antibody against human basic fibroblast growth factor. Cancer Research, 51:6180–6184, 1991.

Gross JL, et al. Modulation of solid tumor growth in vivo by bFGF. Proc. Amer. Assoc. Canc. Res. 31:79, 1990.

Ingber D, et al., Angioinhibins: Synthetic analogues of fumagillin which inhibit angiogenesis and suppress tumor growth. Nature, 48:555–557, 1990.

Weidner N, et al., Tumor angiogenesis and metastasis—correlation in invasive breast carcinoma. N. Engl. J. Med. 324:1–8, 1991.

Weidner N, et al., Tumor angiogensis: A new significant and independent prognostic indicator in early–stage breast carcinoma, J Natl. Cancer Inst. 84:1875–1887, 1992.

Weidner N, Carroll PR, Flax J, Blumenfeld W, Folkman J. Tumor angiogenesis correlates with metastasis in invasive prostate carcinoma. American Journal of Pathology, 143(2):401–409, 1993.

Srivastava A, et al., The prognostic significance of tumor vascularity in intermediate thickness (0.76–4.0 mm thick) skin melanoma. Amer. J. Pathol. 133:419–423, 1988.

Nguyen M, et al., Elevated levels of an angiogenic peptide, basic fibroblast growth factor, in urine of bladder cancer patients. J. Natl. Cancer Inst. 85:241–242, 1993.

Robbins, K.C., "The plasminogen–plasmin enzyme system" Hemostasis and Thrombosis, Basic Principles and Practice, 2nd Edition, ed. by Colman, R.W. et al. J.B. Lippincott Company, pp. 340–357, 1987.

Yoshimura, T, et al., "Cloning, sequencing, and expression of human macrophage stimulating protein (MSP, MST1) confirms MSP as a member of the family of kringle proteins and locates the MSP gene on Chromosome 3" J. Biol. Chem.., vol. 268, No. 21, pp. 15461–15468, 1993.

Browne, M.J., et al., "Expression of recombinant human plasminogen and aglycoplasminogen in HeLa cells" Fibrinolysis vol. 5 (4). 257–260, 1991.

Brem et al., "Interstitial chemotherapy with drug polymer implants for treatment of recurrent gliomas," J. Neurosurg. 74:441–446 (1991).

Muthukkaruppan Vr., et al., Angiogenesis in the mouse cornea. Science 205:1416–1418, 1979.

(List continued on next page.)

Primary Examiner—Cecilia J. Tsang
Assistant Examiner—Anish Gupta
Attorney, Agent, or Firm—Jones & Askew

[57] ABSTRACT

The present invention comprises an aggregate endothelial inhibitor and method of use therefor. The aggregate endothelial inhibitor comprises a protein having a molecular weight of between approximately 45 kilodaltons and 65 kilodaltons as determined by reducing polyacrylamide gel electrophoresis, and having an amino acid sequence substantially similar to that of a murine plasminogen fragment beginning at amino acid number 98 of a murine plasminogen molecule.

30 Claims, 29 Drawing Sheets

OTHER PUBLICATIONS

Passaniti A, et al., "A Simple, quantitative method for assessing angiogenesis and anti–angiogenic agents using reconstituted basement membrane, heparin and fibroblast growth factor," *Lab. Invest.,* vol. 67, p. 519 (1992).

Folkman J., Angiogenesis and its inhibitors in *"Important Advances in Oncology 1985"*, VT DeVita, S. Hellman and S. Rosenberg, editors, J.B. Lippincott, Philadelphia 1985.

Obeso, et al., "Methods in Laboratory Investigation, A Hemangioendothelioma–derived cell line; Its use as a Model for the Study of Endothelial Cell Biology," *Lab. Invest.,* 63(2), pp. 259–269, 1990.

Sotrrup–Jensen, L., et al., *Progress in Chemical Fibrinolysis and Thrombolysis,* vol. 3, Davidson, J.F., et al. eds Raven Press, New York, p. 191 (1978).

Grant, D.S., et al., "Scatter factor induces blood vessel formation in vivo," *Proc. Natl. Acad. Sci.,* vol. 90, pp. 1937–1941 (1993).

Shi, G. et al., "Kringle Domains and Plasmin Denaturation," *Biochem. and Biophys. Res. Comm.,* vol. 178, No. 1, pp. 360–368 (1991).

Scaller, J. et al., "Structural Aspects of the Plasminogen of Various Species," *Enzyme.,* vol. 40, pp. 63–69 (1988).

Wiman, B., et al., "On the Specific Interaction between the Lysine–binding sites in Plasmin and Complementary Sites in $\alpha_2$–Antiplasmin and in Fibrinogen," *Biochemica et Biophysica Acta,* 579, 142 (1979).

Derwent Publications, Ltd., London; JP 58–036–391 (Sankyo KK) Mar. 3, 1983 (Abstract).

M. O'Reilly et al., "The Suppression of Tumor Metastases by a Primary Tumor" *Science* vol. 44, pp. 474–476; 1993.

T. E. Maione et al., "Inhibition of Angiogenesis by Recombinant Human Platelet Factor–4 and Related Peptides" *Science* vol. 247, pp. 77–79; Jan. 5, 1990.

M. A. Moses et al., "Identification of an Inhibitor of Neovascularization from Cartilage" *Science* vol. 248, pp. 1408–1410; Jun. 15, 1990.

O;Reilly, M.S. Holmgren, L., Shing, Y., Chen, C., Rosenthal, R.A., Moses, M., Lane, W.S., Cao, Y., Sage, E.H., and Folkman, J., *Cell* (1994) 79:315–328.

Mouse Plasminogen Sequence:

```
met asp his lys glu val ile leu leu phe leu leu leu leu lys
pro gly gln gly asp ser leu asp gly tyr ile ser thr gln gly
ala ser leu phe ser leu thr lys lys gln leu ala ala gly gly
val ser asp cys leu ala lys cys glu gly glu thr asp phe val
cys arg ser phe gln tyr his ser lys glu gln gln cys val ile
met ala glu asn ser lys thr ser ser ile ile arg met arg asp
val ile leu phe glu lys arg val tyr leu ser glu cys lys thr
gly ile gly asn gly tyr arg gly thr met ser arg thr lys ser
gly val ala cys gln lys trp gly ala thr phe pro his val pro
asn tyr ser pro ser thr his pro asn glu gly leu glu glu asn
tyr cys arg asn pro asp asn asp glu gln gly pro trp cys tyr
thr thr asp pro asp lys arg tyr asp tyr cys asn ile pro glu
cys glu glu glu cys met tyr cys ser gly glu lys tyr glu gly
lys ile ser lys thr met ser gly leu asp cys gln ala trp asp
ser gln ser pro his ala his gly tyr ile pro ala lys phe pro
ser lys asn leu lys met asn tyr cys his asn pro asp gly glu
pro arg pro trp cys phe thr thr asp pro thr lys arg trp glu
tyr cys asp ile pro arg cys thr thr pro pro pro pro pro ser
pro thr tyr gln cys leu lys gly arg gly glu asn tyr arg gly
thr val ser val thr val ser gly lys thr cys gln arg trp ser
glu gln thr pro his arg his asn arg thr pro glu asn phe pro
cys lys asn leu glu glu asn tyr cys arg asn pro asp gly glu
thr ala pro trp cys tyr thr thr asp ser gln leu arg trp glu
tyr cys glu ile pro ser cys glu ser ser ala ser pro asp gln
ser asp ser ser val pro pro glu glu gln thr pro val val gln
glu cys tyr gln ser asp gly gln ser tyr arg gly thr ser ser
thr thr ile thr gly lys lys cys gln ser trp ala ala met phe
pro his arg his ser lys thr pro glu asn phe pro asp ala gly
leu glu met asn tyr cys arg asn pro asp gly asp lys gly pro
trp cys tyr thr thr asp pro ser val arg trp glu tyr cys asn
leu lys arg cys ser glu thr gly gly ser val val glu leu pro
thr val ser gln glu pro ser gly pro ser asp ser glu thr asp
cys met tyr gly asn gly lys asp tyr arg gly lys thr ala val
thr ala ala gly thr pro cys gln gly trp ala ala gln glu pro
his arg his ser ile phe thr pro gln thr asn pro arg ala asp
leu glu lys asn tyr cys arg asn pro asp gly asp val asn gly
pro trp cys tyr thr thr asn pro arg lys leu tyr asp tyr cys
asp ile pro leu cys ala ser ala ser ser phe glu cys gly lys
pro gln val glu pro lys lys cys pro gly arg val val gly gly
cys val ala asn pro his ser trp pro trp gln ile ser leu arg
thr arg phe thr gly gln his phe cys gly gly thr leu ile ala
pro glu trp val leu thr ala ala his cys leu glu lys ser ser
arg pro glu phe tyr lys val ile leu gly ala his glu glu tyr
ile arg gly leu asp val gln glu ile ser val ala lys leu ile
leu glu pro asn asn arg asp ile ala leu leu lys leu ser arg
pro ala thr ile thr asp lys val ile pro ala cys leu pro ser
```

Fig. 1A

```
pro asn tyr met val ala asp arg thr ile cys tyr ile thr gly
trp gly glu thr gln gly thr phe gly ala gly arg leu lys glu
ala gln leu pro val ile glu asn lys val cys asn arg val glu
tyr leu asn asn arg val lys ser thr glu leu cys ala gly gln
leu ala gly gly val asp ser cys gln gly asp ser gly gly pro
leu val cys phe glu lys asp lys tyr ile leu gln gly val thr
ser trp gly leu gly cys ala arg pro asn lys pro gly val tyr
val arg val ser arg phe val asp trp ile glu arg glu met arg
asn asn
```

Fig. 1B

```
MOUSE
HUMAN
RHESUS MONKEY
PORCINE
BOVINE val tyr leu ser glu cys lys thr gly ile gly asn gly tyr arg gly
val tyr leu ser glu cys lys thr gly asn gly lys asn tyr arg gly
val tyr leu ser glu cys lys thr gly asn gly lys asn tyr arg gly
ile tyr leu ser glu cys lys thr gly asn gly lys asn tyr arg gly
ile tyr leu leu glu cys lys thr gly asn gly gln thr tyr arg gly thr met ser arg thr lys ser gly val ala cys gln lys trp gly ala
thr met ser lys thr lys asn gly ile thr cys gln lys trp ser ser
thr met ser lys thr arg thr gly ile thr cys gln lys trp ser ser
thr thr ser lys thr lys ser gly val ile cys gln lys trp ser val
thr thr ala glu thr lys ser gly val thr cys gln lys trp ser ala thr phe pro his val pro asn tyr ser pro ser thr his pro asn glu
thr ser pro his arg pro arg phe ser pro ala thr his pro ser glu
thr ser pro his arg pro thr phe ser pro ala thr his pro ser glu
ser ser pro his ile pro lys tyr ser pro glu lys phe pro leu ala
thr ser pro his val pro lys phe ser pro glu lys phe pro leu ala gly leu glu glu asn tyr cys arg asn pro asp asn asp glu gln gly
gly leu glu glu asn tyr cys arg asn pro asp asn asp pro gln gly
gly leu glu glu asn tyr cys arg asn pro asp asn asp gly gln gly
gly leu glu glu asn tyr cys arg asn pro asp asn asp glu lys gly
gly leu glu glu asn tyr cys arg asn pro asp asn asp glu asn gly pro trp cys tyr thr thr asp pro asp lys arg tyr asp tyr cys asn
pro trp cys tyr thr thr asp pro glu lys arg tyr asp tyr cys asp
pro trp cys tyr thr thr asp pro glu glu arg phe asp tyr cys asp
pro trp cys tyr thr thr asp pro glu thr arg phe asp tyr cys asp
pro trp cys tyr thr thr asp pro asp lys arg tyr asp tyr cys asp ile pro glu cys glu glu glu cys met tyr cys ser gly glu lys tyr
ile leu glu cys glu glu glu cys met his cys ser gly glu asn tyr
ile pro glu cys glu asp glu cys met his cys ser gly glu asn tyr
ile pro glu cys glu asp glu cys met his cys ser gly glu his tyr
ile pro glu cys glu asp lys cys met his cys ser gly glu asn tyr glu gly lys ile ser lys thr met ser gly leu asp cys gln ala trp
asp gly lys ile ser lys thr met ser gly leu glu cys gln ala trp
asp gly lys ile ser lys thr met ser gly leu glu cys gln ala trp
glu gly lys ile ser lys thr met ser gly ile glu cys gln ser trp
glu gly lys ile ala lys thr met ser gly arg asp cys gln ala trp
```

```
asp ser gln ser pro his ala his gly tyr ile pro ala lys phe pro
asp ser gln ser pro his ala his gly tyr ile pro ser lys phe pro
asp ser gln ser pro his ala his gly tyr ile pro ser lys phe pro
gly ser gln ser pro his ala his gly tyr leu pro ser lys phe pro
asp ser gln ser pro his ala his gly tyr ile pro ser lys phe pro ser lys asn leu lys met asn tyr cys his asn pro asp gly glu pro
asn lys asn leu lys lys asn tyr cys arg asn pro asp arg glu leu
asn lys asn leu lys lys asn tyr cys arg asn pro asp gly glu pro
asn lys asn leu lys met asn tyr cys arg asn pro asp gly glu pro
asn lys asn leu lys met asn tyr cys arg asn pro asp gly glu pro arg pro trp cys phe thr thr asp pro thr lys arg trp glu tyr cys
arg pro trp cys phe thr thr asp pro asn lys arg trp glu leu cys
arg pro trp cys phe thr thr asp pro asn lys arg trp glu leu cys
arg pro trp cys phe thr thr asp pro asn lys arg trp glu phe cys
arg pro trp cys phe thr thr asp pro gln lys arg trp glu phe cys asp ile pro arg cys thr thr pro pro pro pro ser pro thr tyr
asp ile pro arg cys thr thr pro pro pro ser ser gly pro thr tyr
asp ile pro arg cys thr thr pro pro pro ser ser gly pro thr tyr
asp ile pro arg cys thr thr pro pro pro thr ser gly pro thr tyr
asp ile pro arg cys thr thr pro pro pro ser ser gly pro lys tyr gln cys leu lys gly arg gly glu asn tyr arg gly thr val ser val
gln cys leu lys gly thr gly glu asn tyr arg gly asn val ala val
gln cys leu lys gly thr gly glu asn tyr arg gly asp val ala val
gln cys leu lys gly arg gly glu asn tyr arg gly thr val ser val
gln cys leu lys gly thr gly lys asn tyr gly gly thr val ala val thr val ser gly lys thr cys gln arg trp ser glu gln thr pro his
thr val ser gly his thr cys gln his trp ser ala gln thr pro his
thr val ser gly his thr cys his gly trp ser ala gln thr pro his
thr ala ser gly his thr cys gln arg trp ser

```
thr asp ser gln leu arg trp glu tyr cys glu ile pro ser cys glu
thr asn ser gln val arg trp glu tyr cys lys ile pro ser cys asp
thr asn ser gln val arg trp glu tyr cys lys ile pro ser cys glu
thr asp ser glu val arg trp asp tyr cys lys ile pro ser cys gly
thr asn ser glu val arg trp glu tyr cys thr ile pro ser cys glu ser ser ala ser pro asp gln ser asp ser ser val pro pro glu glu
ser ser pro val ser thr glu gln leu ala pro thr ala pro pro glu
ser ser pro val ser thr glu pro leu asp pro thr ala pro pro glu
ser ser thr thr ser thr glu his leu asp ala pro val pro pro glu
ser ser pro leu ser thr glu arg met asp val pro val pro pro glu gln thr pro val val gln glu cys tyr gln ser asp gly gln ser tyr
leu thr pro val val gln asp cys tyr his gly asp gly gln ser tyr
leu thr pro val val gln glu cys tyr his gly asp gly gln ser tyr
gln thr pro val ala gln asp cys tyr arg gly asn gly glu ser tyr
gln thr pro val pro gln asp cys tyr his gly asn gly gln ser tyr arg gly thr ser ser thr thr ile thr gly lys lys cys gln ser trp
arg gly thr ser ser thr thr thr gly lys lys cys gln ser trp
arg gly thr ser ser thr thr thr gly lys lys cys gln ser trp
arg gly thr ser ser thr thr ile thr gly arg lys cys gln ser trp
arg gly thr ser ser thr thr ile thr gly arg lys cys gln ser trp ala ala met phe p

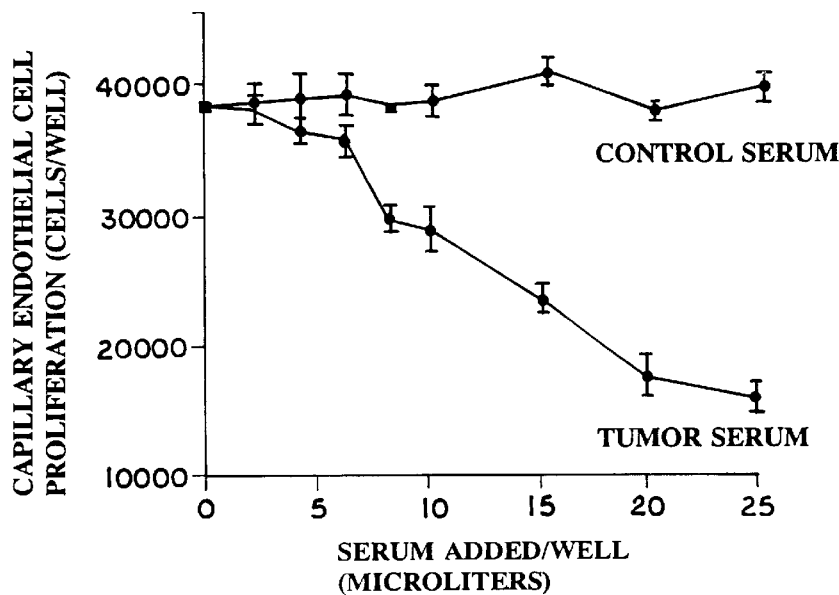
Fig_5
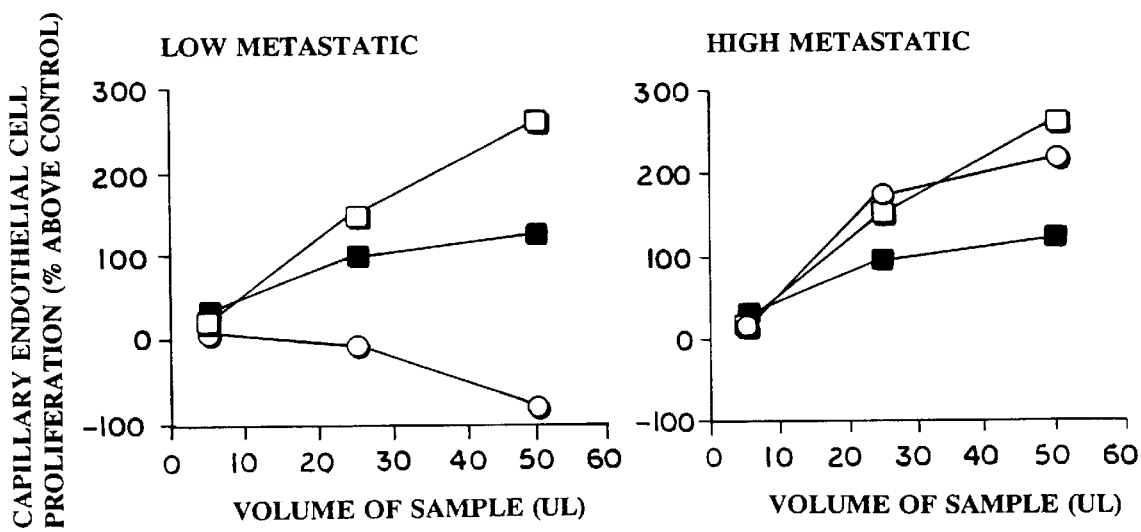
Fig_6A    Fig_6B

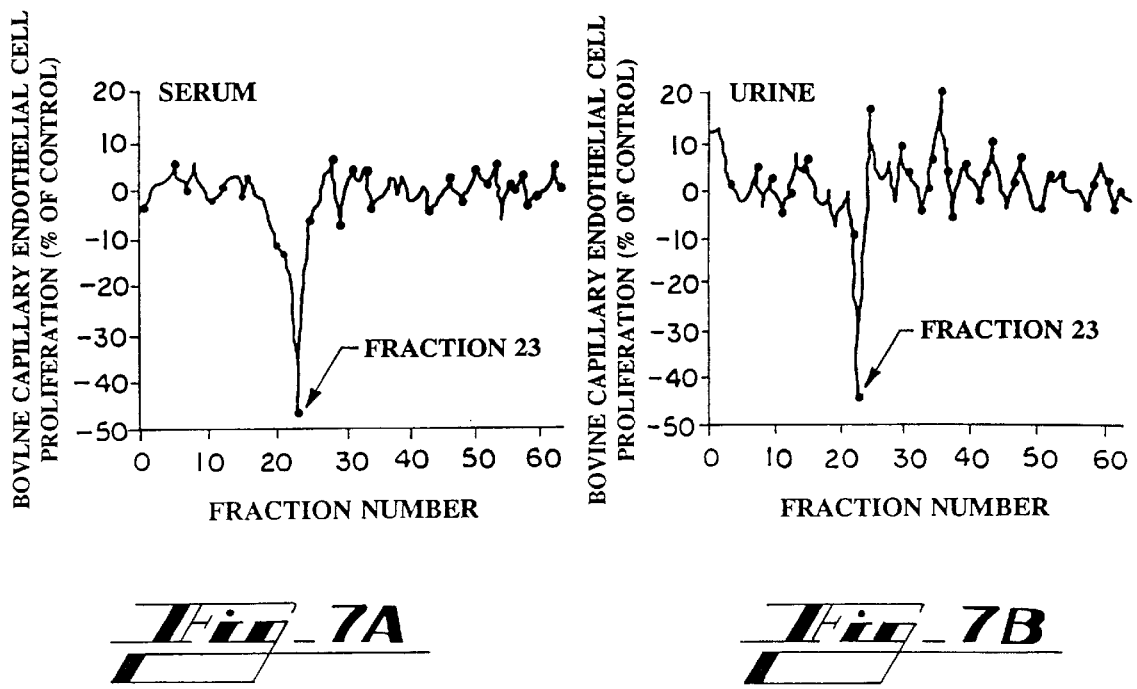
FIG_7A FIG_7B

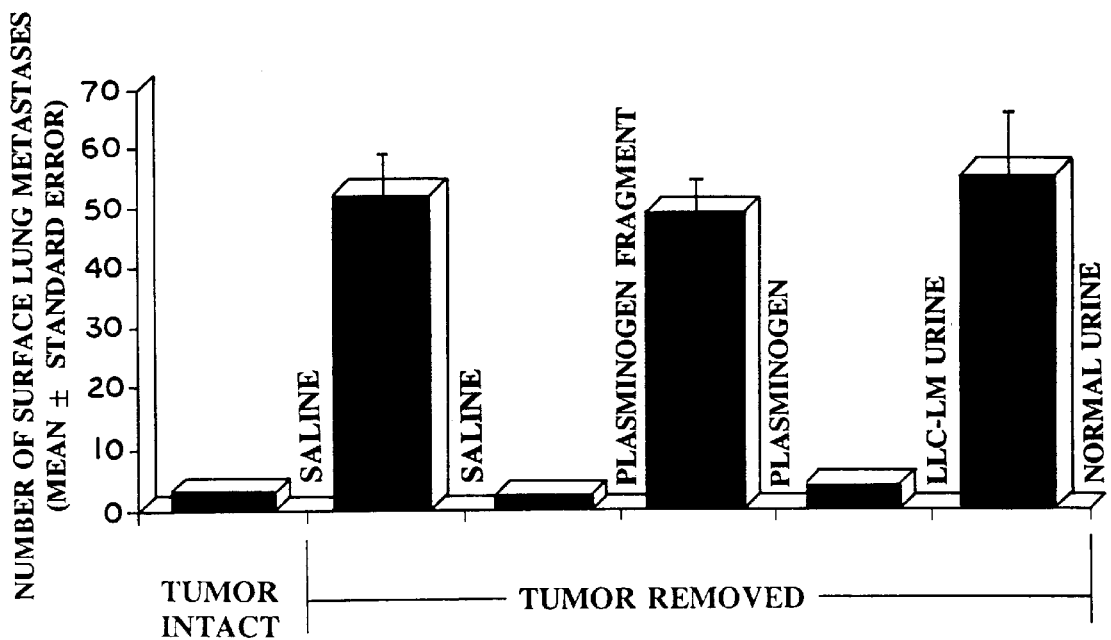
Fig_8
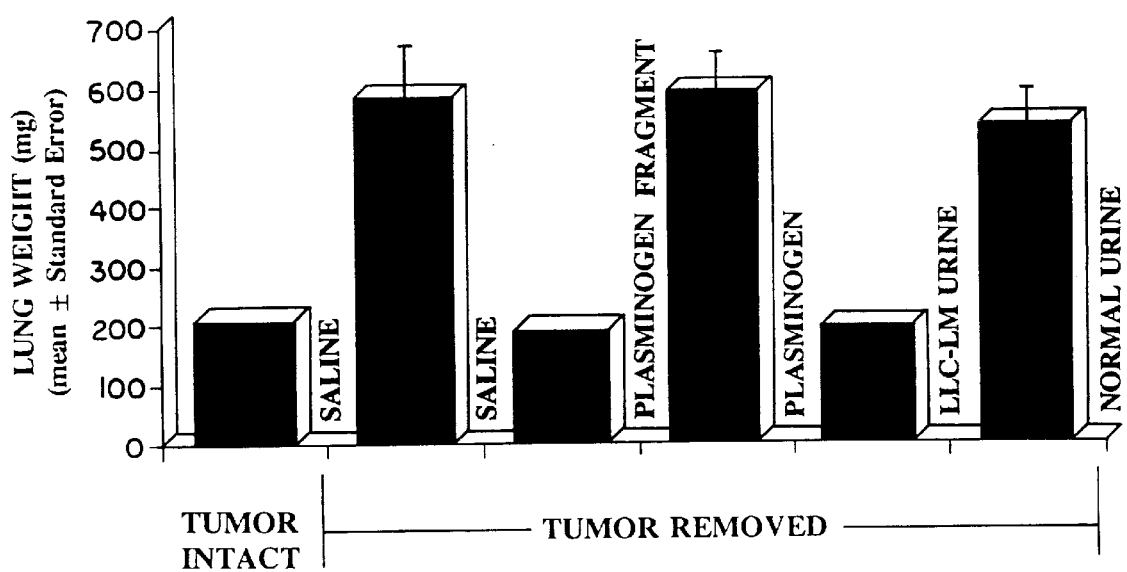
Fig_9

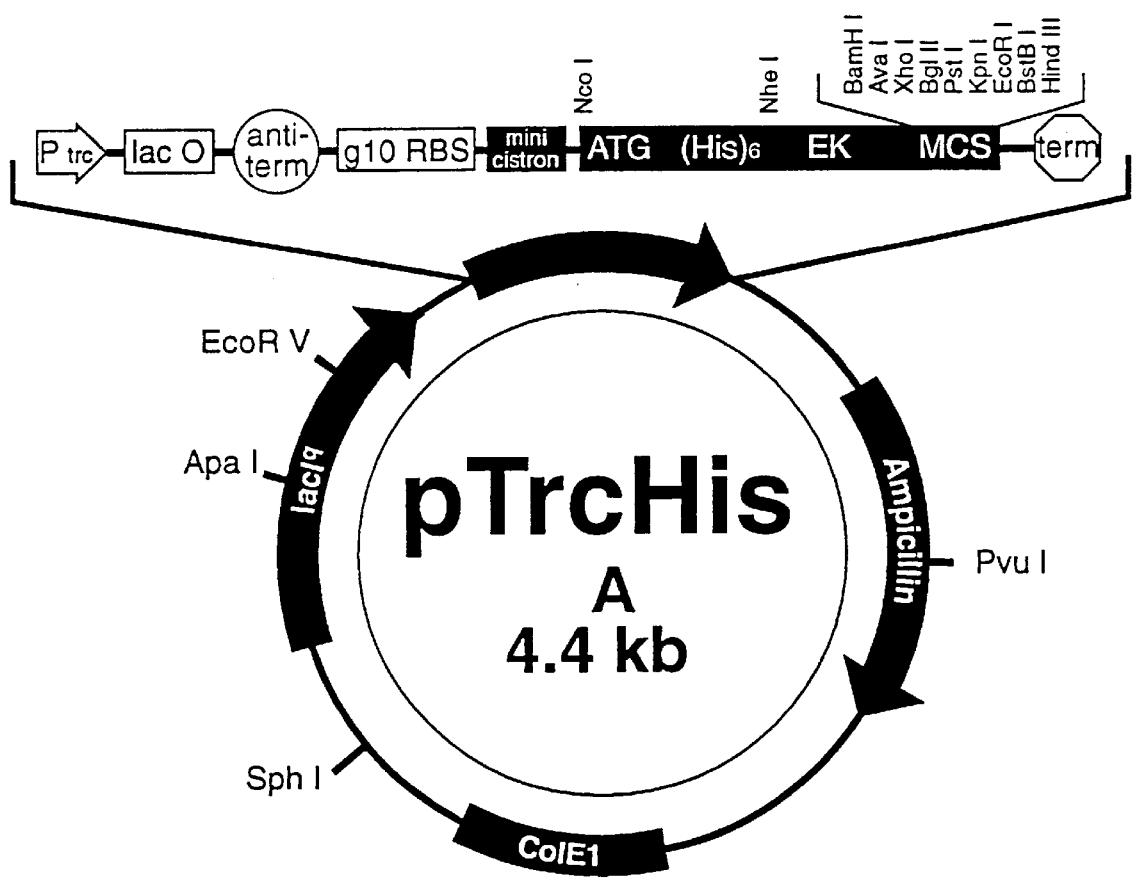
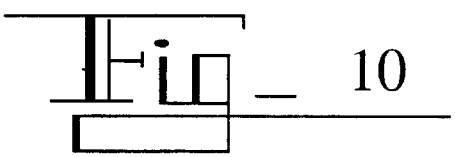

Fig_11

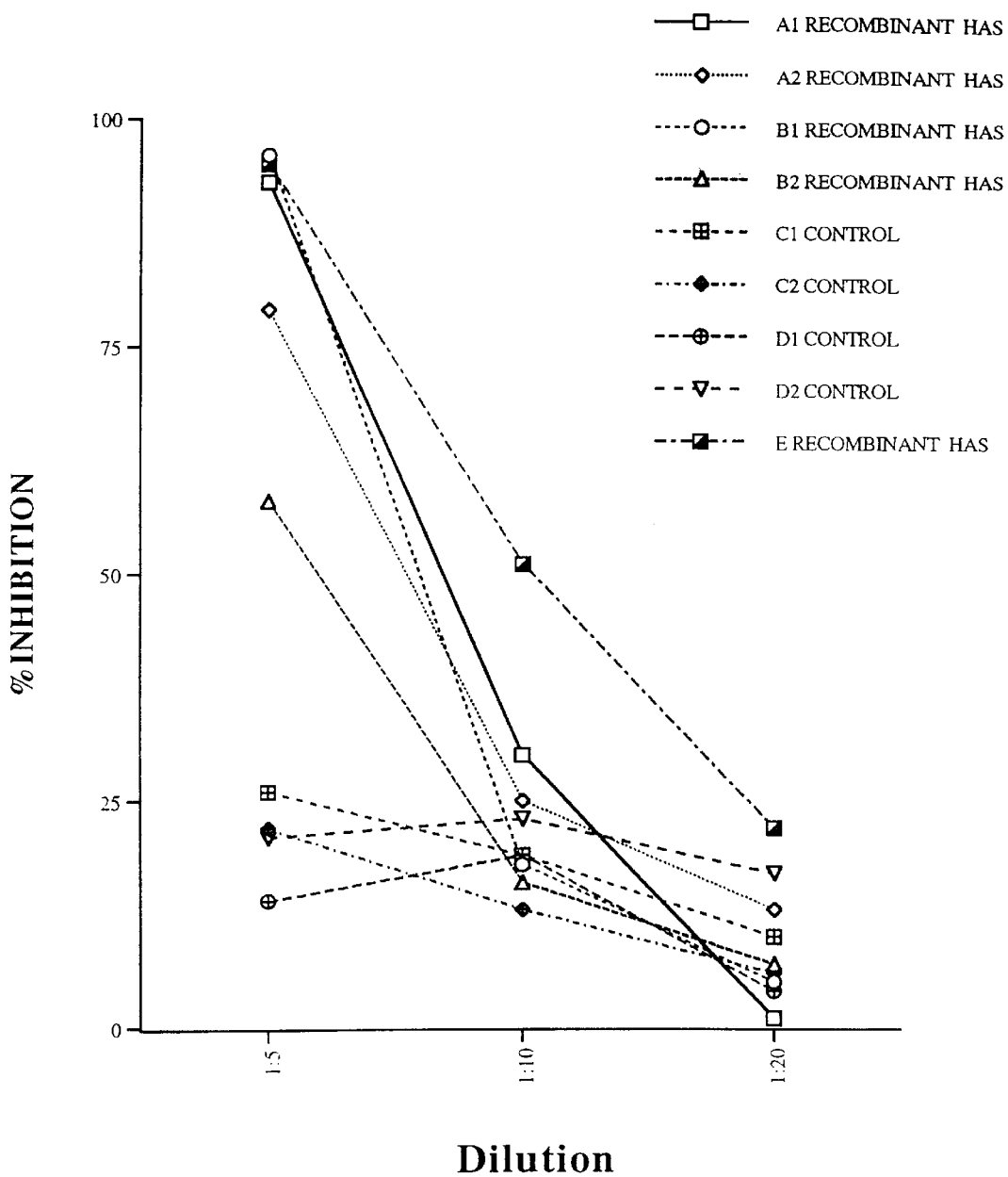

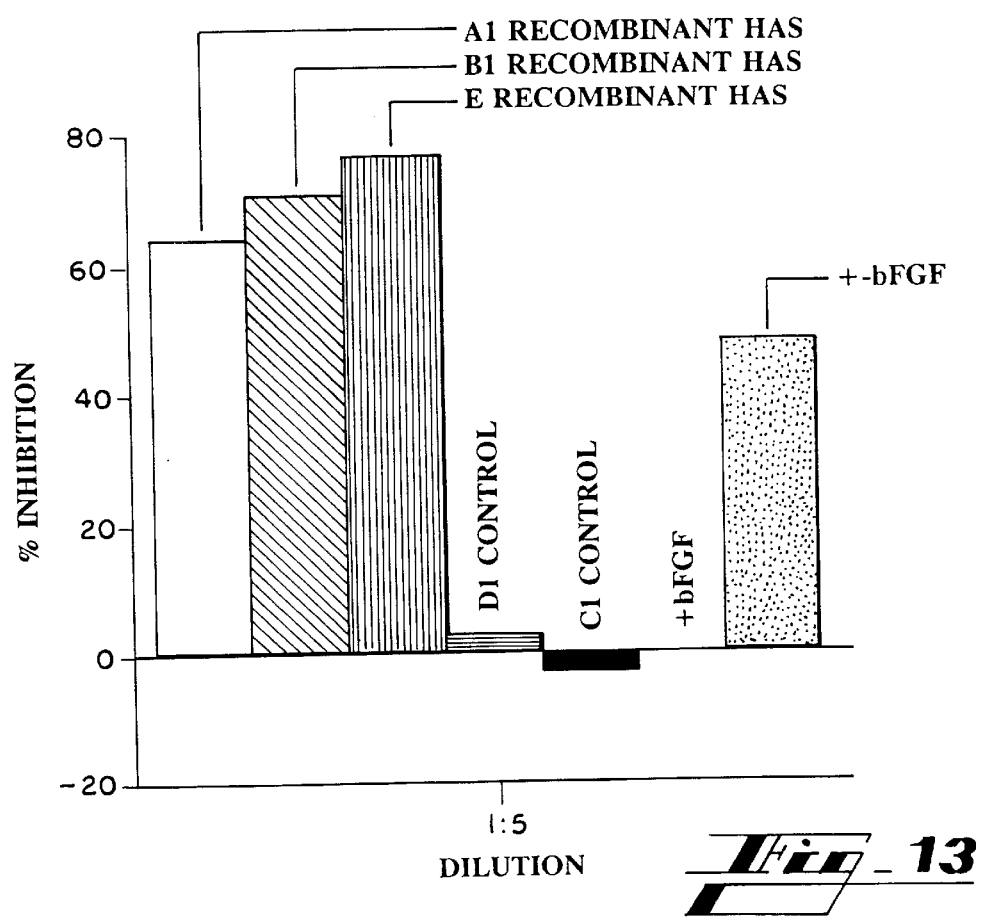

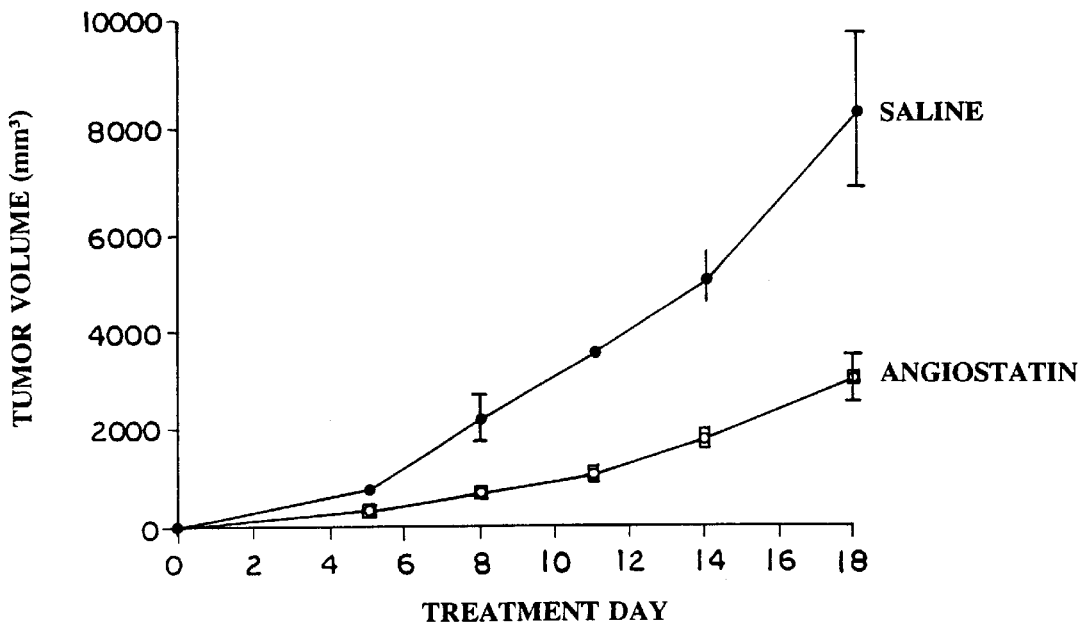
Fig_17
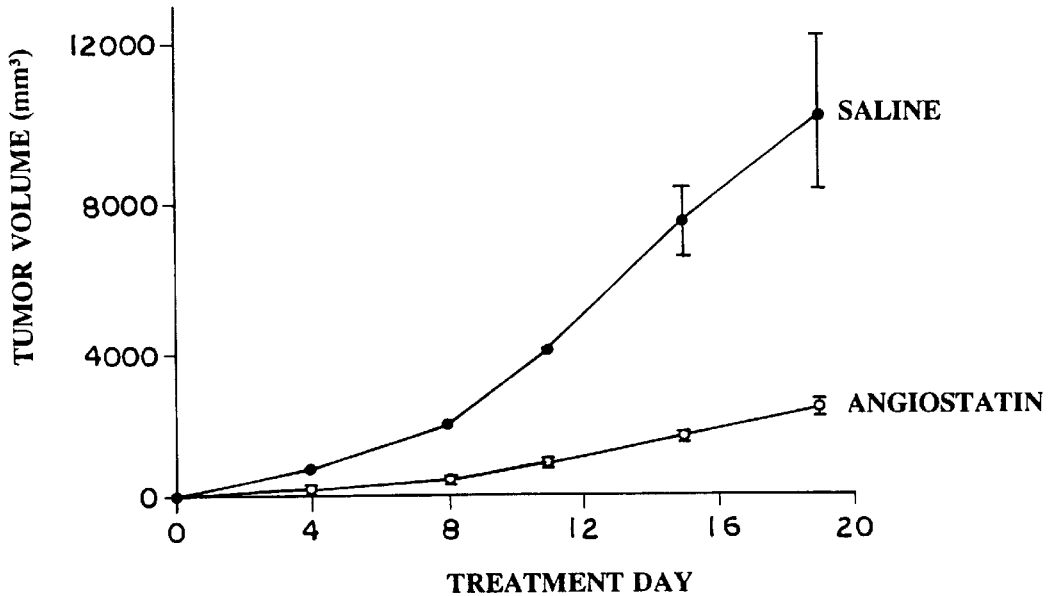
Fig_18

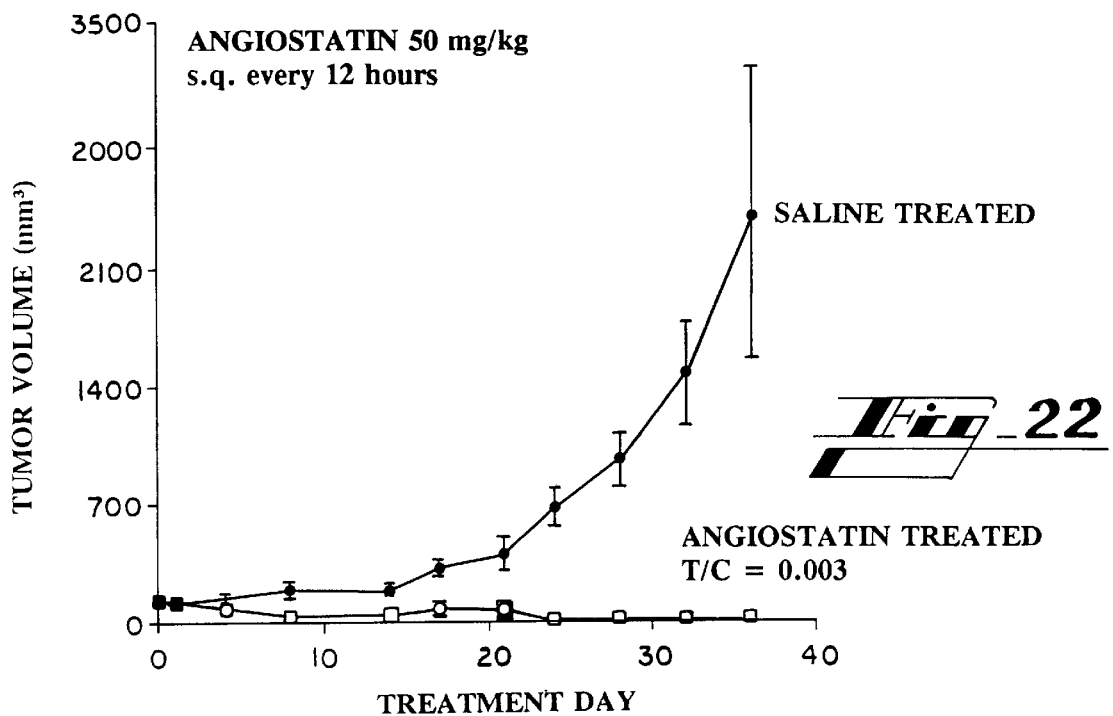
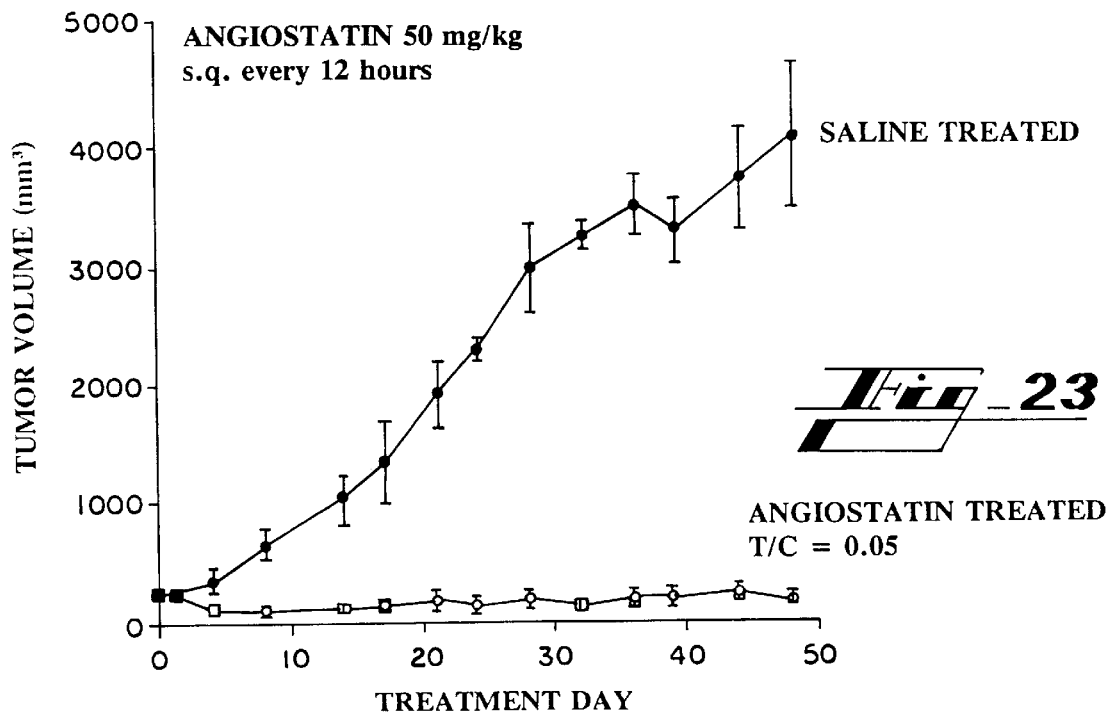

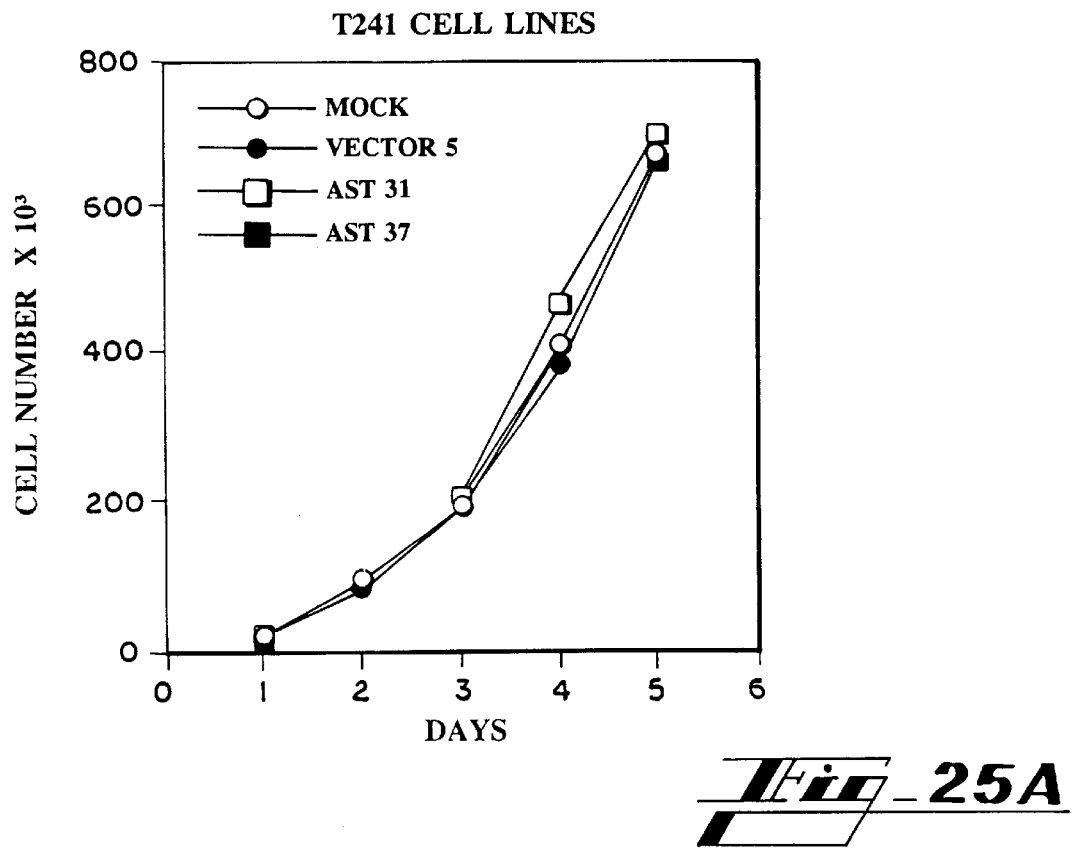
Fig_25A
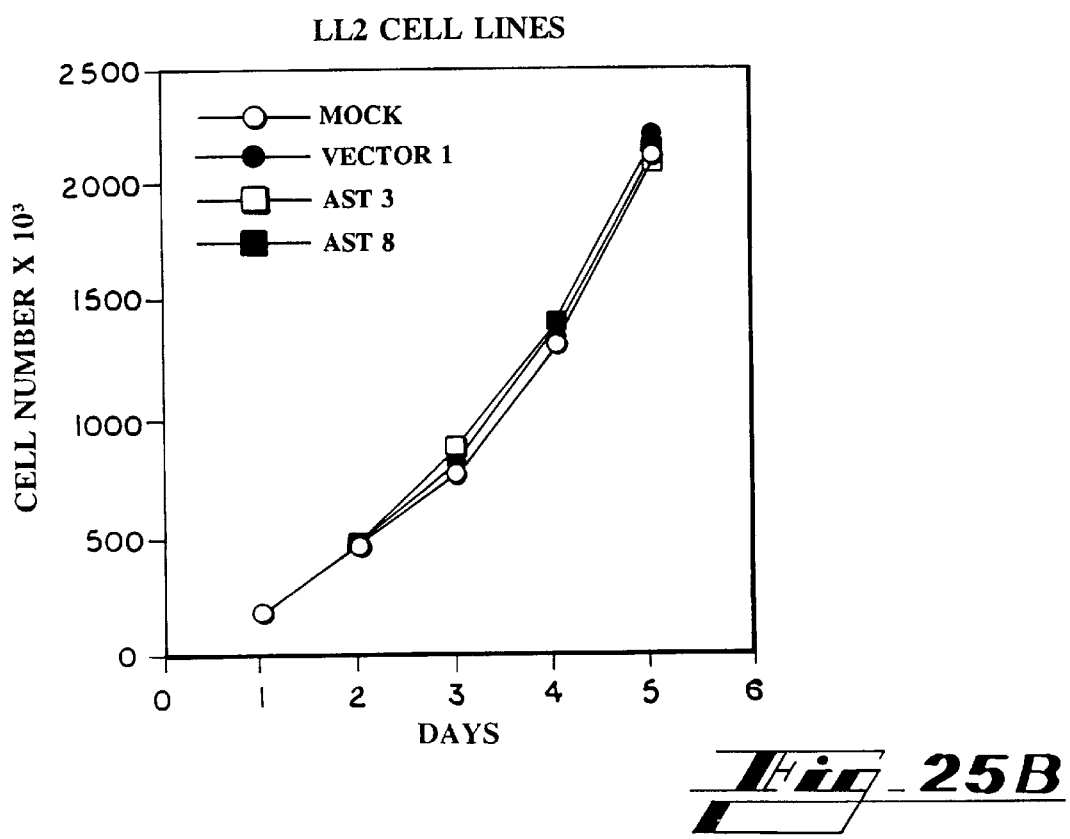
Fig_25B

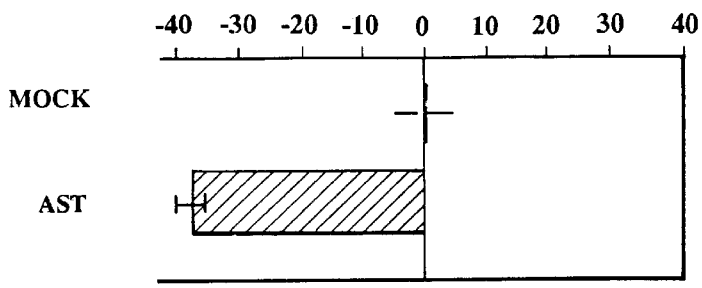
Fig_26A
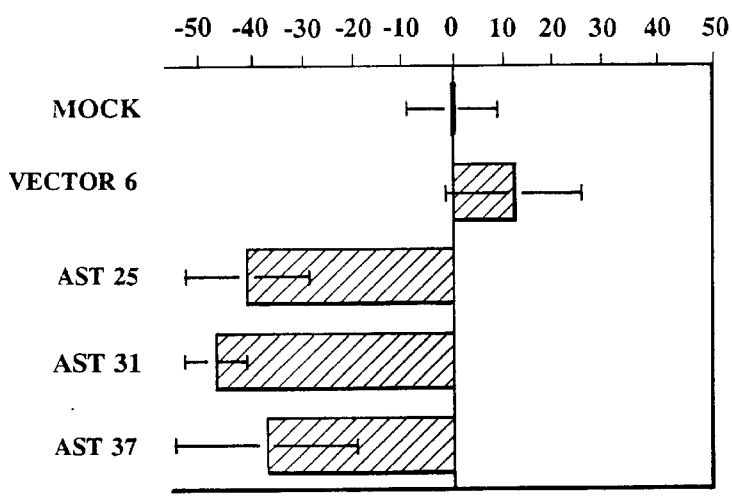
Fig_26B
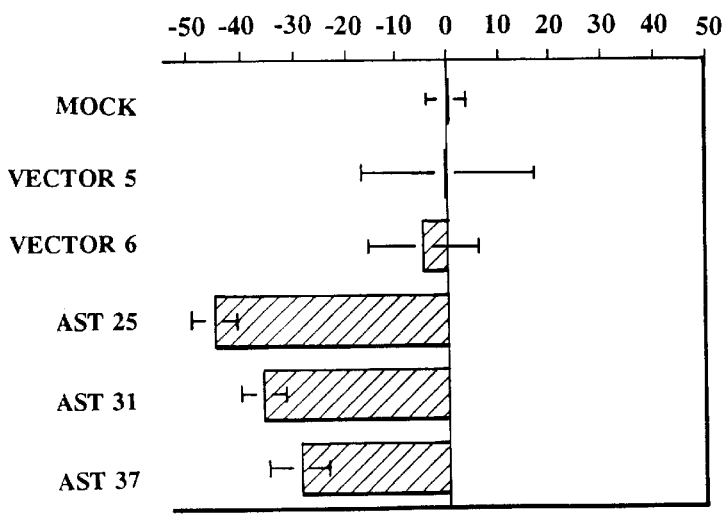
Fig_26C

Fig_28

5,861,372

AGGREGATE ANGIOSTATIN AND METHOD OF USE

FIELD OF THE INVENTION

The present invention relates to endothelial inhibitors, called angiostatin, which reversibly inhibit proliferation of endothelial cells. More particularly, the present invention relates to angiostatin proteins that can be isolated from body fluids such as blood or urine, or can be synthesized by recombinant, enzymatic or chemical methods. The angiostatin is capable of inhibiting angiogenesis related diseases and modulating angiogenic processes. In addition, the present invention relates to diagnostic assays and kits for angiostatin measurement, to histochemical kits for localization of angiostatin, to DNA sequences coding for angiostatin and molecular probes to monitor angiostatin biosynthesis, to antibodies that are specific for the angiostatin, to the development of peptide agonists and antagonists to the angiostatin receptor, to anti-angiostatin receptor-specific antibody agonists and antagonists, and to cytotoxic agents linked to angiostatin peptides.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

The hypothesis that tumor growth is angiogenesis-dependent was first proposed in 1971. (Folkman J., Tumor angiogenesis: Therapeutic implications., *N. Engl. Jour. Med.* 285:1182 1186, 1971) In its simplest terms it states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire G H, et al. Vascular reactions of normal and malignant tumors in vivo. I. Vascular reactions of mice to wounds and to normal and neoplastic transplants. *J. Natl. Cancer Inst.* 6:73–85, 1945)

(2) Tumors grown in isolated perfused organs where blood vessels do not proliferate are limited to 1–2 mm$^3$ but expand rapidly to >1000 times this volume when they are transplanted to mice and become neovascularized. (Folkman J, et al., Tumor behavior in isolated perfused organs: In vitro growth and metastasis of biopsy material in rabbit thyroid and canine intestinal segments. *Annals of Surgery* 164:491–502, 1966)

(3) Tumor growth in the avascular cornea proceeds slowly and at a linear rate, but switches to exponential growth after neovascularization. (Gimbrone, M. A., Jr. et al., Tumor growth and neovascularization: An experimental model using the rabbit cornea. *J. Natl. Cancer Institute* 52:41–427, 1974)

(4) Tumors suspended in the aqueous fluid of the anterior chamber of the rabbit eye, remain viable, avascular and limited in size to <1 mm$^3$. Once they are implanted on the iris vascular bed, they become neovascularized and grow rapidly, reaching 16,000 times their original volume within 2 weeks. (Gimbrone M A Jr., et al., Tumor dormancy in vivo by prevention of neovascularization. *J. Exp. Med.* 136:261–276)

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0 +2.5 mm. (Knighton D., Avascular and vascular phases of tumor growth in the chick embryo. *British J. Cancer*, 35:347–356, 1977)

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien W., et al., The blood supply of experimental liver metastases. II. A microcirculatory study of normal and tumor vessels of the liver with the use of perfused silicone rubber. *Surgery* 68:334–340, 1970)

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman J, et al., Induction of angiogenesis during the transition from hyperplasia to neoplasia. *Nature* 339:58–61, 1989)

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim K J, et al., Inhibition of vascular endothelial growth factor-induced angiogenesis suppresses tumor growth in vivo. *Nature* 362:841–844, 1993)

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori A, et al., Suppression of solid tumor growth by immunoneutralizing monoclonal antibody against human basic fibroblast growth factor. *Cancer Research,* 51:6180–6184, 1991)

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross J L, et al. Modulation of solid tumor growth in vivo by bFGF. *Proc. Amer. Assoc. Canc. Res.* 31:79, 1990)

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber D, et al., Angioinhibins: Synthetic analogues of fumagillin which inhibit angiogenesis and suppress tumor growth. *Nature,* 48:555–557, 1990). There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 mm$^3$). These implants rarely grow larger until one or more of them becomes neovascularized.

(14) Intensity of neovascularization in breast cancer (Weidner N, et al., Tumor angiogenesis correlates with metastasis in invasive breast carcinoma. *N. Engl. J. Med.* 324:1–8, 1991, and Weidner N, et al., Tumor angiogenesis: A new significant and independent prognostic indicator in early-stage breast carcinoma, *J Natl. Cancer Inst.* 84:1875–1887, 1992) and in prostate cancer (Weidner N, Carroll P R, Flax J, Blumenfeld W, Folkman J. Tumor angiogenesis correlates with metastasis in invasive prostate carcinoma. *American Journal of Pathology,* 143(2):401–409, 1993) correlates highly with risk of future metastasis.

(15) Metastasis from human cutaneous melanoma is rare prior to neovascularization. The onset of neovascularization leads to increased thickness of the lesion and an increasing risk of metastasis. (Srivastava A, et al., The prognostic significance of tumor vascularity in intermediate thickness (0.76–4.0 mm thick) skin melanoma. *Amer. J. Pathol.* 133:419–423, 1988)

(16) In bladder cancer, the urinary level of an angiogenic peptide, bFGF, is a more sensitive indicator of status and extent of disease than is cytology. (Nguyen M, et al., Elevated levels of an angiogenic peptide, basic fibroblast growth factor, in urine of bladder cancer patients. *J. Natl. Cancer Inst.* 85:241–242, 1993)

Thus, it is clear that angiogenesis plays a major role in the metastasis of a cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

What is needed therefore is a composition and method which can inhibit the unwanted growth of blood vessels, especially into tumors. Also needed is a method for detecting, measuring, and localizing the composition. The composition should be able to overcome the activity of endogenous growth factors in premetastatic tumors and prevent the formation of the capillaries in the tumors thereby inhibiting the growth of the tumors. The composition, fragments of the composition, and antibodies specific to the composition, should also be able to modulate the formation of capillaries in other angiogenic processes, such as wound healing and reproduction. The composition and method for inhibiting angiogenesis should preferably be non-toxic and produce few side effects. Also needed is a method for detecting, measuring, and localizing the binding sites for the composition as well as sites of biosynthesis of the composition. The composition and fragments of the composition should be capable of being conjugated to other molecules for both radioactive and non-radioactive labeling purposes

SUMMARY OF THE INVENTION

In accordance with the present invention, compositions and methods are provided that are effective for modulating angiogenesis, and inhibiting unwanted angiogenesis, especially angiogenesis related to tumor growth. The present invention includes a protein, which has been named "angiostatin", defined by its ability to overcome the angiogenic activity of endogenous growth factors such as bFGF, in vitro, and by it amino acid sequence homology and structural similarity to an internal portion of plasminogen beginning at approximately plasminogen amino acid 98. Angiostatin comprises a protein having a molecular weight of between approximately 38 kilodaltons and 45 kilodaltons as determined by reducing polyacrylamide gel electrophoresis and having an amino acid sequence substantially similar to that of a fragment of murine plasminogen beginning at amino acid number 98 of an intact murine plasminogen molecule (SEQ ID NO:2).

The amino acid sequence of angiostatin varies slightly between species. For example, in human angiostatin the amino acid sequence is substantially similar to the sequence of the above described murine plasminogen fragment, although an active human angiostatin sequence may start at either amino acid number 97 or 99 of an intact human plasminogen amino acid sequence. Further, fragments of human plasminogen has similar anti-angiogenic activity as shown in a mouse tumor model. It is to be understood that the number of amino acids in the active angiostatin molecule may vary and all amino acid sequences that have endothelial inhibiting activity are contemplated as being included in the present invention.

The present invention provides methods and compositions for treating diseases and processes mediated by undesired and uncontrolled angiogenesis by administering to a human or animal a composition comprising a substantially purified angiostatin or angiostatin derivative in a dosage sufficient to inhibit angiogenesis. The present invention is particularly useful for treating, or for repressing the growth of, tumors. Administration of angiostatin to a human or animal with prevascularized metastasized tumors will prevent the growth or expansion of those tumors.

The present invention also encompasses DNA sequences encoding angiostatin, expression vectors containing DNA sequences encoding angiostatin, and cells containing one or more expression vectors containing DNA sequences encoding angiostatin. The present invention further encompasses gene therapy methods whereby DNA sequences encoding angiostatin are introduced into a patient to modify in vivo angiostatin levels.

The present invention also includes diagnostic methods and kits for detection and measurement of angiostatin in biological fluids and tissues, and for localization of angiostatin in tissues and cells. The diagnostic method and kit can be in any configuration well known to those of ordinary skill in the art. The present invention also includes antibodies specific for the angiostatin molecule and portions thereof, and antibodies that inhibit the binding of antibodies specific for the angiostatin. These antibodies can be polyclonal antibodies or monoclonal antibodies. The antibodies specific for the angiostatin can be used in diagnostic kits to detect the presence and quantity of angiostatin which is diagnostic or prognostic for the occurrence or recurrence of cancer or other disease mediated by angiogenesis. Antibodies specific for angiostatin may also be administered to a human or animal to passively immunize the human or animal against angiostatin, thereby reducing angiogenic inhibition.

The present invention also includes diagnostic methods and kits for detecting the presence and quantity of antibodies that bind angiostatin in body fluids. The diagnostic method and kit can be in any configuration well known to those of ordinary skill in the art.

The present invention also includes anti-angiostatin receptor-specific antibodies that bind to the angiostatin receptor and transmit the appropriate signal to the cell and act as agonists or antagonists.

The present invention also includes angiostatin peptide fragments and analogs that can be labeled isotopically or with other molecules or proteins for use in the detection and visualization of angiostatin binding sites with techniques, including, but not limited to, positron emission tomography, autoradiography, flow cytometry, radioreceptor binding assays, and immunohistochemistry.

These angiostatin peptides and analogs also act as agonists and antagonists at the angiostatin receptor, thereby enhancing or blocking the biological activity of angiostatin. Such peptides are used in the isolation of the angiostatin receptor.

The present invention also includes angiostatin, angiostatin fragments, angiostatin antisera, or angiostatin receptor agonists and angiostatin receptor antagonists linked to cytotoxic agents for therapeutic and research applications. Still further, angiostatin, angiostatin fragments, angiostatin antisera, angiostatin receptor agonists and angiostatin receptor antagonists are combined with pharmaceutically acceptable excipients, and optionally sustained-release compounds or compositions, such as biodegradable polymers, to form therapeutic compositions.

The present invention includes molecular probes for the ribonucleic acid and deoxyribonucleic acid involved in transcription and translation of angiostatin. These molecular probes provide means to detect and measure angiostatin biosynthesis in tissues and cells.

Accordingly, it is an object of the present invention to provide a composition comprising an angiostatin.

It is another object of the present invention to provide a method of treating diseases and processes that are mediated by angiogenesis.

It is yet another object of the present invention to provide a diagnostic or prognostic method and kit for detecting the presence and amount of angiostatin in a body fluid or tissue.

It is yet another object of the present invention to provide a method and composition for treating diseases and processes that are mediated by angiogenesis including, but not limited to, hemangioma, solid tumors, blood borne tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

It is another object of the present invention to provide a composition for treating or repressing the growth of a cancer.

It is an object of the present invention to provide compounds that modulate or mimic the production or activity of enzymes that produce angiostatin in vivo or in vitro.

It is a further object of the present invention to provide angiostatin or anti-angiostatin antibodies by direct injection of angiostatin DNA into a human or animal needing such angiostatin or anti-angiostatin antibodies.

It is an object of present invention to provide a method for detecting and quantifying the presence of an antibody specific for an angiostatin in a body fluid.

Still another object of the present invention is to provide a composition consisting of antibodies to angiostatin that are selective for specific regions of the angiostatin molecule that do not recognize plasminogen.

It is another object of the present invention to provide a method for the detection or prognosis of cancer.

It is another object of the present invention to provide a composition for use in visualizing and quantitating sites of angiostatin binding in vivo and in vitro.

It is yet another object of the present invention to provide a composition for use in detection and quantification of angiostatin biosynthesis.

It is yet another object of the present invention to provide a therapy for cancer that has minimal side effects.

Still another object of the present invention is to provide a composition comprising angiostatin or an angiostatin peptide linked to a cytotoxic agent for treating or repressing the growth of a cancer.

Another object of the present invention is to provide a method for targeted delivery of angiostatin-related compositions to specific locations.

Yet another object of the invention is to provide compositions and methods useful for gene therapy for the modulation of angiogenic processes.

These and other objects, features and advantages of the present invention will become apparent after a review of the following detailed description of the disclosed embodiments and the appended claims.

BRIEF DESCRIPTION OF THE FIGURES

FIG. 1 shows SEQ ID NO:1, the amino acid sequence of the whole murine plasminogen.

FIG. 2 shows the beginning sequence of the angiostatin for murine (SEQ ID NO:2) and compares the murine sequence with corresponding human (SEQ ID NO:3), Rhesus monkey (SEQ ID NO:4), porcine (SEQ ID NO:5) and bovine (SEQ ID NO:6) plasminogen peptide fragments. The mouse sequence is listed first, followed by human, Rhesus, porcine and bovine.

FIG. 5 shows dose response curve for serum derived from mice bearing Lewis lung carcinoma (LLC-Low) versus serum from normal mice. Bovine capillary endothelial cells were assayed in a bFGF-driven 72-hour proliferation assay.

FIG. 6 shows that both low and high metastatic tumors contain endothelial mitogenic activity in their ascites, but only the low metastatic tumor line has endothelial inhibitory activity in the serum.

FIG. 7 shows a C4 Reverse Phase Chromatographic profile of partially purified serum or urine from tumor-bearing animals.

FIG. 8 shows surface lung metastases after the 13 day treatment of mice with intact plasminogen molecule, active fraction from a lysine binding site I preparation of human plasminogen, concentrated urine from tumor bearing mice and concentrated urine from normal mice.

FIG. 9 shows lung weight after the 13 day treatment of mice with intact plasminogen molecule of human plasminogen, active fraction from lysine binding site I preparation, concentrated urine from tumor bearing mice and concentrated urine from normal mice.

FIG. 10 is a schematic representation of the pTrcHis vector.

FIG. 11 depicts an immunoblot of $E.coli$ expressed human angiostatin from a 10 L scaled-up fermentation probed with monoclonal antibody against human plasminogen kringle region 1–3. Arrow shows recombinant human angiostatin. A) shows recombinant angiostatin eluted with 0.2M amino caproic acid; B) shows the last wash with 1×PBS of the lysine column; and C) shows clarified lysate from cracked cells.

FIG. 12. Is a graph depicting percent inhibition of growing bovine capillary endothelial cells as a function of dilution of stock; A1, A2, B1, B2,and E are recombinant clones that express human angiostatin anti-angiogenesis activity; C1, C2, D1, and D2 controls are negative controls clones containing vector only without the human DNA sequence coding for angiostatin.

FIG. 13 shows the inhibitory effect on proliferation of recombinant human angiostatin on bovine capillary endothelial cells in vitro.

FIG. 17 shows the effect of the removal of a Lewis lung carcinoma primary tumor on the growth of its lung metastases.

FIG. 18 shows the growth proliferation and apoptotic index after tumor resection.

FIG. 22 shows the effect of administration of angiostatin protein to immunodeficient SCID mice having implanted human prostate carcinoma PC-3 cells on total tumor volume as a function of time over a 24 day period.

FIG. 23 shows the effect of administration of angiostatin protein to immunodeficient SCID mice having implanted human breast carcinoma MDA-MB cells on total tumor volume as a function of time over a 24 day period.

FIG. 25 depicts the number of cells as a function of days for non-transfected cells (mock); cells transfected with the vector alone, without the DNA sequence coding for angiostatin (Vector 5), and two angiostatin expressing clones (AST 31 and AST 37). Panel (a) represents the results of transfection of T241 cells. Panel (b) represents the results of LL2 cells.

FIG. 26 shows the results of culture medium derived from $E.\ coli$ cells containing the angiostatin clone on cell number. Non-transfected cells (mock); cells transfected with the vector alone, without the DNA sequence coding for angiostatin (Vector 5), and three angiostatin expressing clones (AST 25, AST 31 and AST 37). Panel (a) represents the results of incubation of culture medium from control (mock) and all angiostatin clones (expressing and non-expressing) on cell number. Panel (b) represents the results of incubation of culture medium from control (mock), vector alone (vector 6) and angiostatin clones expressing mouse angiostatin on cell number. Panel (c) represents the results of incubation of purified culture medium from control (mock) and angiostatin clones expressing mouse angiostatin on cell number, wherein the culture medium was purified over a lysine-sepharose colume to yield lysine binding components.

DETAILED DESCRIPTION

Figure 3A:
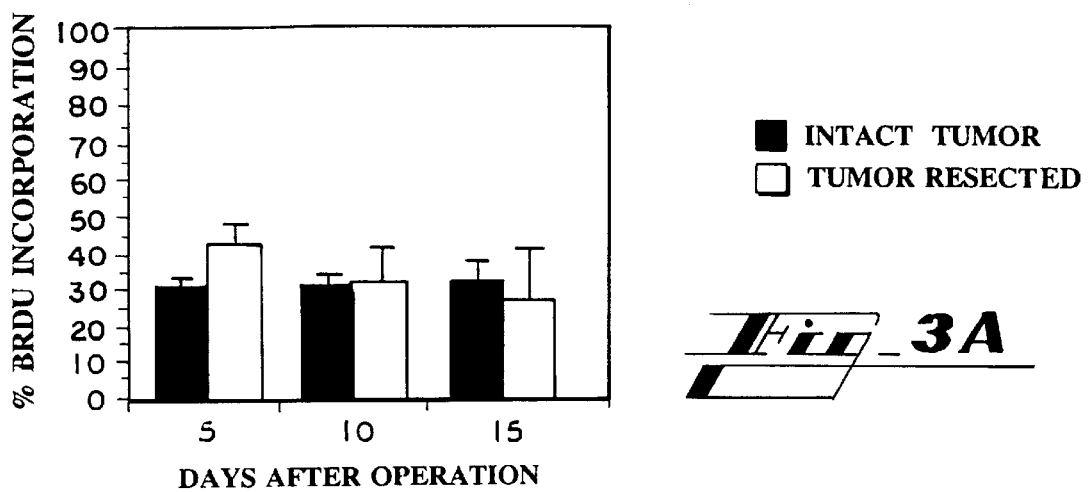
FIG. 3 shows BrdU labeling index of tumor cells in the lung in the presence or absence of a primary tumor.

The present invention includes compositions and methods for the detection and treatment of diseases and processes that are mediated by or associated with angiogenesis. The composition is angiostatin, which can be isolated from body fluids including, but not limited to, serum, urine and ascites, or synthesized by chemical or biological methods (e.g. cell culture, recombinant gene expression, peptide synthesis, and in vitro enzymatic catalysis of plasminogen or plasmin to yield active angiostatin). Recombinant techniques include gene amplification from DNA sources using the polymerase chain reaction (PCR), and gene amplification from RNA sources using reverse transcriptase/PCR. Angiostatin inhibits the growth of blood vessels into tissues such as unvascularized or vascularized tumors.

The present invention also encompasses a composition comprising, a vector containing a DNA sequence encoding angiostatin, wherein the vector is capable of expressing angiostatin when present in a cell, a composition comprising a cell containing a vector, wherein the vector contains a DNA sequence encoding angiostatin or fragments or analogs thereof, and wherein the vector is capable of expressing angiostatin when present in the cell, and a method comprising, implanting into a human or non-human animal a cell containing a vector, wherein the vector contains a DNA sequence encoding angiostatin, and wherein the vector is capable of expressing angiostatin when present in the cell.

Still further, the present invention encompasses angiostatin, angiostatin fragments, angiostatin antisera, angiostatin receptor agonists or angiostatin receptor antagonists that are combined with pharmaceutically acceptable excipients, and optionally sustained-release compounds or compositions, such as biodegradable polymers, to form therapeutic compositions. In particular, the invention includes a composition comprising an antibody that specifically binds to angiostatin, wherein the antibody does not bind to plasminogen.

More particularly, the present invention includes a protein designated angiostatin that has a molecular weight of approximately 38 to 45 kilodaltons (kD) that is capable of overcoming the angiogenic activity of endogenous growth factors such as bFGF, in vitro. Angiostatin is a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The term "substantially similar," when used in reference to angiostatin amino acid sequences, means an amino acid sequence having anti-angiogenic activity and having a molecular weight of approximately 38 kD to 45 kD, which also has a high degree of sequence homology to the peptide fragment of mouse plasminogen beginning approximately at amino acid number 98 in mouse plasminogen and weighing 38 kD to 45 kD. A high degree of homology means at least approximately 60% amino acid homology, desirably at least approximately 70% amino acid homology, and more desirably at least approximately 80% amino acid homology. The term "endothelial inhibiting activity" as used herein means the capability of a molecule to inhibit angiogenesis in general and, for example, to inhibit the growth of bovine capillary endothelial cells in culture in the presence of fibroblast growth factor.

The amino acid sequence of the complete murine plasminogen molecule is shown in FIG. 1 and in SEQ ID NO:1, The sequence for angiostatin begins approximately at amino acid 98. Active human angiostatin may start at either amino acid 97 or 99 of the intact human plasminogen molecule. The amino acid sequence of the first 339 amino acids of angiostatin from mouse is shown in FIG. 2, (SEQ ID NO:2), and is compared with the sequences of corresponding plasminogen peptide fragments from human (SEQ ID NO:3, Rhesus monkey (SEQ ID NO:4), porcine (SEQ ID NO:5) and bovine (SEQ ID NO:6) plasminogen. Given that these sequences are identical in well over 50% of their amino acids, it is to be understood that the amino acid sequence of the angiostatin is substantially similar among species. The total number of amino acids in angiostatin is not known precisely but is defined by the molecular weight of the active molecule. The amino acid sequence of the angiostatin of the present invention may vary depending upon from which species the plasminogen molecule is derived. Thus, although the angiostatin of the present invention that is derived from human plasminogen has a slightly different sequence than angiostatin derived from mouse, it has anti-angiogenic activity as shown in a mouse tumor model.

Angiostatin has been shown to be capable of inhibiting the growth of endothelial cells in vitro. Angiostatin does not inhibit the growth of cell lines derived from other cell types. Specifically, angiostatin has no effect on Lewis lung carcinoma cell lines, mink lung epithelium, 3T3 fibroblasts, bovine aortic smooth muscle cells, bovine retinal pigment epithelium, MDCk cells (canine renal epithelium), WI38 cells (human fetal lung fibroblasts) EFN cells (murine fetal fibroblasts) and LM cells (murine connective tissue). Endogenous angiostatin in a tumor bering mouse is effective at inhibiting metastases at a systemic concentration of approximately 10 mg angiostatin/kg body weight.

Angiostatin has a specific three dimensional conformation that is defined by the kringle region of the plasminogen molecule. (Robbins, K. C., "The plasminogen-plasmin enzyme system" *Hemostasis and Thrombosis, Basic Principles and Practice,* 2nd Edition, ed. by Colman, R. W. et al. J. B. Lippincott Company, pp. 340–357, 1987). There are five such kringle regions, which are conformationally related motifs and have substantial sequence homology, in the $NH_2$ terminal portion of the plasminogen molecule. The three dimensional conformation of angiostatin is believed to encompass plasminogen kringle regions 1 through 3 and a part of kringle region 4. Each kringle region of the plasminogen molecule contains approximately 80 amino acids and contains 3 disulfide bonds. This cysteine motif is known to exist in other biologically active proteins. These proteins include, but are not limited to, prothrombin, hepatocyte growth factor, scatter factor and macrophage stimulating protein. (Yoshimura, T, et al., "Cloning, sequencing, and expression of human macrophage stimulating protein (MSP, MST1) confirms MSP as a member of the family of kringle proteins and locates the MSP gene on Chromosome 3" *J. Biol. Chem.*, Vol. 268, No. 21, pp. 15461–15468, 1993). It is contemplated that any isolated protein or peptide having a three dimensional kringle-like conformation or cysteine motif that has anti-angiogenic activity in vivo, is part of the present invention.

The present invention also includes the detection of the angiostatin in body fluids and tissues for the purpose of diagnosis or prognosis of diseases such as cancer. The present invention also includes the detection of angiostatin binding sites and receptors in cells and tissues. The present invention also includes methods of treating or preventing angiogenic diseases and processes including, but not limited to, arthritis and tumors by stimulating the production of angiostatin, and/or by administering substantially purified angiostatin, or angiostatin agonists or antagonists, and/or angiostatin antisera or antisera directed against angiostatin antisera to a patient. Additional treatment methods include administration of angiostatin, angiostatin fragments, angiostatin analogs, angiostatin antisera, or angiostatin receptor agonists and antagonists linked to cytotoxic agents. It is to be understood that the angiostatin can be animal or human in origin. Angiostatin can also be produced synthetically by chemical reaction or by recombinant techniques in conjunction with expression systems. Angiostatin can also be produced by enzymatically cleaving isolated plasminogen or plasmin to generate peptides having anti-angiogenic activity. Angiostatin may also be produced by compounds that mimic the action of endogenous enzymes that cleave plasminogen to angiostatin. Angiostatin production may also be modulated by compounds that affect the activity of plasminogen cleaving enzymes.

Passive antibody therapy using antibodies that specifically bind angiostatin can be employed to modulate angiogenic-dependent processes such as reproduction, development, and wound healing and tissue repair. In addition, antisera directed to the Fab regions of angiostatin antibodies can be administered to block the ability of endogenous angiostatin antisera to bind angiostatin.

The present invention also encompasses gene therapy whereby the gene encoding angiostatin is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a gene such as angiostatin may be placed in a patient and thus prevent occurrence of angiogenesis; or a gene that makes tumor cells more susceptible to radiation could be inserted and then radiation of the tumor would cause increased killing of the tumor cells.

Many protocols for transfer of angiostatin DNA or angiostatin regulatory sequences are envisioned in this invention. Transfection of promoter sequences, other than one normally found specifically associated with angiostatin, or other sequences which would increase production of angiostatin protein are also envisioned as methods of gene therapy. An example of this technology is found in Transkaryotic Therapies, Inc., of Cambridge, Mass., using homologous recombination to insert a "genetic switch" that turns on an erythropoietin gene in cells. See Genetic Engineering News, Apr. 15, 1994. Such "genetic switches" could be used to activate angiostatin (or the angiostatin receptor) in cells not normally expressing angiostatin (or the angiostatin receptor).

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of angiostatin DNA or angiostatin regulatory sequences.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of angiostatin may be accomplished by administering compounds that bind to the angiostatin gene, or control regions associated with the angiostatin gene, or its corresponding RNA transcript to modify the rate of transcription or translation. Additionally, cells transfected with a DNA sequence encoding angiostatin may be administered to a patient to provide an in vivo source of angiostatin. For example, cells may be transfected with a vector containing a nucleic acid sequence encoding angiostatin.

The term "vector" as used herein means a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising an angiostatin DNA sequence is operatively linked to an expression control sequence to form an expression vector capable of expressing angiostatin. The transfected cells may be cells derived from the patient's normal tissue, the patient's diseased tissue, or may be non-patient cells.

For example, tumor cells removed from a patient can be transfected with a vector capable of expressing the angiostatin protein of the present invention, and re-introduced into the patient. The transfected tumor cells produce angiostatin levels in the patient that inhibit the growth of the tumor. Patients may be human or non-human animals. Cells may also be transfected by non-vector, or physical or chemical methods known in the art such as electroporation, ionoporation, or via a "gene gun." Additionally, angiostatin DNA may be directly injected, without the aid of a carrier, into a patient. In particular, angiostatin DNA may be injected into skin, muscle or blood.

The gene therapy protocol for transfecting angiostatin into a patient may either be through integration of the angiostatin DNA into the genome of the cells, into minichromosomes or as a separate replicating or non-replicating DNA construct in the cytoplasm or nucleoplasm of the cell. Angiostatin expression may continue for a long-period of time or may be reinjected periodically to maintain a desired level of the angiostatin protein in the cell, the tissue or organ or a determined blood level.

Angiostatin can be isolated on an HPLC C4 column (see Table 3). The angiostatin protein is eluted at 30 to 35% in an acetonitrile gradient. On a sodium dodecyl sulfate polyacrylamide gel electrophoresis (PAGE) gel under reducing conditions, the protein band with activity eluted as a single peak at approximately 38 kilodaltons.

The inventors have shown that a growing primary tumor is associated with the release into the blood stream of specific inhibitor(s) of endothelial cell proliferation, including angiostatin which can suppress angiogenesis within a metastasis and thereby inhibit the growth of the metastasis itself. The source of the angiostatin associated with the primary tumor is not known. The compound may be produced by degradation of plasminogen by a specific protease, or angiostatin could be produced by expression of a specific gene coding for angiostatin.

The angiogenic phenotype of a primary tumor depends on production of angiogenic peptides in excess of endothelial cell inhibitors which are elaborated by normal cells, but are believed to be down-regulated during transformation to neoplasia. While production of angiostatin may be down-regulated in an individual tumor cell relative to production by its parent cell type, the total amount of inhibitor elaborated by the whole tumor may be sufficient to enter the circulation and suppress endothelial growth at remote sites of micrometastases. Angiostatin remains in the circulation for a significantly longer time than the angiogenic peptide(s) released by a primary tumor. Thus, the angiogenic peptides appear to act locally, whereas angiostatin acts globally and circulates in the blood with a relatively long half-life. The half-life of the angiostatin is approximately 12 hours to 5 days.

Although not wanting to be bound by the following hypothesis, it is believed that when a tumor becomes angiogenic it releases one or more angiogenic peptides (e.g., aFGF, bFGF, VEGF, IL-8, GM-CSF, etc.), which act locally, target endothelium in the neighborhood of a primary tumor from an extravascular direction, and do not circulate (or circulate with a short half-life). These angiogenic peptides must be produced in an amount sufficient to overcome the action of endothelial cell inhibitor (inhibitors of angiogenesis) for a primary tumor to continue to expand its population. Once such a primary tumor is growing well, it continues to release endothelial cell inhibitors into the circulation. According to this hypothesis, these inhibitors act remotely at a distance from the primary tumor, target capillary endothelium of a metastasis from an intravascular direction, and continue to circulate. Thus, just at the time when a remote metastasis might begin to initiate angiogenesis, the capillary endothelium in its neighborhood could be inhibited by incoming angiostatin.

Once a primary tumor has reached sufficient size to cause angiostatin to be released continuously into the circulation, it is difficult for a second tumor implant (or a micrometastasis) to initiate or increase its own angiogenesis. If a second tumor implant (e.g., into the subcutaneous space, or into the cornea, or intravenously to the lung) occurs shortly after the primary tumor is implanted, the primary tumor will not be able to suppress the secondary tumor (because angiogenesis in the secondary tumor will already be well underway). If two tumors are implanted simultaneously (e.g., in opposite flanks), the inhibitors may have an equivalent inhibiting effect on each other.

The angiostatin of the present invention can be:
  (i) Administered to tumor-bearing humans or animals as anti-angiogenic therapy;
  (ii) Monitored in human or animal serum, urine, or tissues as prognostic markers; and
  (iii) Used as the basis to analyze serum and urine of cancer patients for similar angiostatic molecules.

It is contemplated as part of the present invention that angiostatin can be isolated from a body fluid such as blood or urine of patients or the angiostatin can be produced by recombinant DNA methods or synthetic peptide chemical methods that are well known to those of ordinary skill in the art. Protein purification methods are well known in the art and a specific example of a method for purifying angiostatin, and assaying for inhibitor activity is provided in the examples below. Isolation of human endogenous angiostatin is accomplished using similar techniques.

One example of a method of producing angiostatin using recombinant DNA techniques entails the steps of (1) identifying and purifying angiostatin as discussed above, and as more fully described below, (2) determining the N-terminal amino acid sequence of the purified inhibitor, (3) synthetically generating 5' and 3' DNA oligonucleotide primers for the angiostatin sequence, (4) amplifying the angiostatin gene sequence using polymerase, (5) inserting the amplified sequence into an appropriate vector such as an expression vector, (6) inserting the gene containing vector into a microorganism or other expression system capable of expressing the inhibitor gene, and (7) isolating the recombinantly produced inhibitor. Appropriate vectors include viral, bacterial and eukaryotic (such as yeast) expression vectors. The above techniques are more fully described in laboratory manuals such as "Molecular Cloning: A Laboratory Manual" Second Edition by Sambrook et al., Cold Spring Harbor Press, 1989. The DNA sequence of human plasminogen has been published (Browne, M. J., et al., "Expression of recombinant human plasminogen and aglycoplasminogen in HeLa cells" Fibrinolysis Vol.5 (4). 257–260, 1991) and is incorporated herein by reference.

The gene for angiostatin may also be isolated from cells or tissue (such as tumor cells) that express high levels of angiostatin by (1) isolating messenger RNA from the tissue, (2) using reverse transcriptase to generate the corresponding DNA sequence and then (3) using the polymerase chain reaction (PCR) with the appropriate primers to amplify the DNA sequence coding for the active angiostatin amino acid sequence.

Yet another method of producing angiostatin, or biologically active fragments thereof, is by peptide synthesis. Once a biologically active fragment of an angiostatin is found using the assay system described more fully below, it can be sequenced, for example by automated peptide sequencing methods. Alternatively, once the gene or DNA sequence which codes for angiostatin is isolated, for example by the methods described above, the DNA sequence can be determined using manual or automated sequencing methods well know in the art. The nucleic acid sequence in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the peptide is known, the fragment can be synthesized by techniques well known in the art, as exemplified by "Solid Phase Peptide Synthesis: A Practical Approach" E. Atherton and R. C. Sheppard, IRL Press, Oxford, England. Similarly, multiple fragments can be synthesized which are subsequently linked together to form larger fragments. These synthetic peptide fragments can also be made with amino acid substitutions at specific locations to test for agonistic and antagonistic activity in vitro and in vivo. Peptide fragments that possess high affinity binding to tissues can be used to isolate the angiostatin receptor on affinity columns. Isolation and purification of the angiostatin receptor is a fundamental step towards elucidating the mechanism of action of angiostatin. Isolation of an angiostatin receptor and identification of angiostatin agonists and antagonists will facilitate development of drugs to modulate the activity of the angiostatin receptor, the final pathway to biological activity. Isolation of the receptor enables the construction of nucleotide probes to monitor the location and synthesis of the receptor, using in situ and solution hybridization technology. Further, the gene for the angiostatin receptor can be isolated, incorporated into an expression vector and transfected into cells, such as patient tumor cells to increase the ability of a cell type, tissue or tumor to bind angiostatin and inhibit local angiogenesis.

Angiostatin is effective in treating diseases or processes that are mediated by, or involve, angiogenesis. The present invention includes the method of treating an angiogenesis mediated disease with an effective amount of angiostatin, or a biologically active fragment thereof, or combinations of angiostatin fragments that collectively possess anti-angiogenic activity, or angiostatin agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Angiostatin is useful in the treatment of disease of excessive or abnormal stimulation of endothelial cells. These diseases include, but are not limited to, intestinal adhesions, Crohn's disease, atherosclerosis, scleroderma, and hypertrophic scars, i.e., keloids. Angiostatin can be used as a birth control agent by preventing vascularization required for embryo implantation. Angiostatin is useful in the treatment of diseases that have angiogenesis as a pathologic consequence such as cat scratch disease (*Rochele minalia quintosa*) and ulcers (*Helicobacter pylori*).

The synthetic peptide fragments of angiostatin have a variety of uses. The peptide that binds to the angiostatin receptor with high specificity and avidity is radiolabeled and employed for visualization and quantitation of binding sites using autoradiographic and membrane binding techniques. This application provides important diagnostic and research tools. Knowledge of the binding properties of the angiostatin receptor facilitates investigation of the transduction mechanisms linked to the receptor.

In addition, labeling angiostatin peptides with short lived isotopes enables visualization of receptor binding sites in vivo using positron emission tomography or other modern radiographic techniques to locate tumors with angiostatin binding sites.

Systematic substitution of amino acids within these synthesized peptides yields high affinity peptide agonists and antagonists to the angiostatin receptor that enhance or diminish angiostatin binding to its receptor. Such agonists are used to suppress the growth of micrometastases, thereby limiting the spread of cancer. Antagonists to angiostatin are applied in situations of inadequate vascularization, to block the inhibitory effects of angiostatin and promote angiogenesis. For example, this treatment may have therapeutic effects to promote wound healing in diabetics.

Angiostatin peptides are employed to develop affinity columns for isolation of the angiostatin receptor from cultured tumor cells. Isolation and purification of the angiostatin receptor is followed by amino acid sequencing. Using this information the gene or genes coding for the angiostatin receptor can be identified and isolated. Next, cloned nucleic acid sequences are developed for insertion into vectors capable of expressing the receptor. These techniques are well known to those skilled in the art. Transfection of the nucleic acid sequence(s) coding for angiostatin receptor into tumor cells, and expression of the receptor by the transfected tumor cells enhances the responsiveness of these cells to endogenous or exogenous angiostatin and thereby decreasing the rate of metastatic growth.

Cytotoxic agents such as ricin, are linked to angiostatin, and high affinity angiostatin peptide fragments, thereby providing a tool for destruction of cells that bind angiostatin. These cells may be found in many locations, including but not limited to, micrometastases and primary tumors. Peptides linked to cytotoxic agents are infused in a manner designed to maximize delivery to the desired location. For example, ricin-linked high affinity angiostatin fragments are delivered through a cannula into vessels supplying the target site or directly into the target. Such agents are also delivered in a controlled manner through osmotic pumps coupled to infusion cannulae. A combination of angiostatin antagonists may be co-applied with stimulators of angiogenesis to increase vascularization of tissue. This therapeutic regimen provides an effective means of destroying metastatic cancer.

Angiostatin may be used in combination with other compositions and procedures for the treatment of diseases. For example, a tumor may be treated conventionally with surgery, radiation or chemotherapy combined with angiostatin and then angiostatin may be subsequently administered to the patient to extend the dormancy of micrometastases and to stabilize and inhibit the growth of any residual primary tumor. Additionally, angiostatin, angiostatin fragments, angiostatin antisera, angiostatin receptor agonists, angiostatin receptor antagonists, or combinations thereof, are combined with pharmaceutically acceptable excipients, and optionally sustained-release matrix, such as biodegradable polymers, to form therapeutic compositions.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating therapeutic composition of the present invention may be a solid, liquid or aerosol and may be administered by any known route of administration. Examples of solid therapeutic compositions include pills, creams, and implantable dosage units. The pills may be administered orally, the therapeutic creams may be administered topically. The implantable dosage unitst may be administered locally, for example at a tumor site, or which may be implanted for systemic release of the therapeutic angiogenesis-modulating composition, for example subcutaneously. Examples of liquid composition include formulations adapted for injection subcutaneously, intravenously, intraarterially, and formulations for topical and intraocular administration. Examples of aersol formulation include inhaler formulation for administration to the lungs.

The angiostatin of the present invention also can be used to generate antibodies that are specific for the inhibitor and its receptor. The antibodies can be either polyclonal antibodies or monoclonal antibodies. These antibodies that specifically bind to the angiostatin or angiostatin receptors can be used in diagnostic methods and kits that are well known to those of ordinary skill in the art to detect or quantify the angiostatin or angiostatin receptors in a body fluid or tissue. Results from these tests can be used to diagnose or predict the occurrence or recurrence of a cancer and other angiogenic mediated diseases.

The angiostatin also can be used in a diagnostic method and kit to detect and quantify antibodies capable of binding angiostatin. These kits would permit detection of circulating angiostatin antibodies which indicates the spread of micrometastases in the presence of angiostatin secreted by primary tumors in situ. Patients that have such circulating anti-angiostatin antibodies may be more likely to develop multiple tumors and cancers, and may be more likely to have recurrences of cancer after treatments or periods of remission. The Fab fragments of these anti-angiostatin antibodies may be used as antigens to generate anti-angiostatin Fab-fragment antisera which can be used to neutralize anti-angiostatin antibodies. Such a method would reduce the removal of circulating angiostatin by anti-angiostatin antibodies, thereby effectively elevating circulating angiostatin levels.

Another aspect of the present invention is a method of blocking the action of excess endogenous angiostatin. This can be done by passively immunizing a human or animal with antibodies specific for the undesired angiostatin in the system. This treatment can be important in treating abnormal ovulation, menstruation and placentation, and vasculogenesis. This provides a useful tool to examine the effects of angiostatin removal on metastatic processes. The Fab fragment of angiostatin antibodies contains the binding site for angiostatin. This fragment is isolated from angiostatin antibodies using techniques known to those skilled in the art. The Fab fragments of angiostatin antisera are used as antigens to generate production of anti-Fab fragment serum. Infusion of this antiserum against the Fab fragments of angiostatin prevents angiostatin from binding to angiostatin antibodies. Therapeutic benefit is obtained by neutralizing endogenous anti-angiostatin antibodies by blocking the binding of angiostatin to the Fab fragments of anti-angiostatin. The net effect of this treatment is to facilitate the ability of endogenous circulating angiostatin to reach target cells, thereby decreasing the spread of metastases.

It is to be understood that the present invention is contemplated to include any derivatives of the angiostatin that have endothelial inhibitory activity. The present invention includes the entire angiostatin protein, derivatives of the angiostatin protein and biologically-active fragments of the angiostatin protein. These include proteins with angiostatin activity that have amino acid substitutions or have sugars or other molecules attached to amino acid functional groups. The present invention also includes genes that code for angiostatin and the angiostatin receptor, and to proteins that are expressed by those genes.

The proteins and protein fragments with the angiostatin activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the angiostatin may be incorporated into biodegradable polymers allowing for sustained release of the compound, the polymers being implanted in the vicinity of where drug delivery is desired, for example, at the site of a tumor or implanted so that the angiostatin is slowly released systemically. Osmotic minipumps may also be used to provide controlled delivery of high concentrations of angiostatin through cannulae to the site of interest, such as directly into a metastatic growth or into the vascular supply to that tumor. The biodegradable polymers and their use are described, for example, in detail in Brem et al., *J. Neurosurg.* 74:441–446 (1991), which is hereby incorporated by reference in its entirety.

The dosage of the angiostatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the angiostatin can be administered. Depending upon the half-life of the angiostatin in the particular animal or human, the angiostatin can be administered between several times per day to once a week. It is to be understood that the present invention has application for both human and veterinary use. The methods of the present invention contemplate single as well as multiple administrations, given either simultaneously or over an extended period of time.

The angiostatin formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The angiostatin formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit- dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with angiostatin proteins, or biologically functional peptide fragements thereof, to provide dual therapy to the patient.

Angiogenesis inhibiting peptides of the present invention can be synthesized in a standard microchemical facility and purity checked with HPLC and mass spectrophotometry. Methods of peptide synthesis, HPLC purification and mass spectrophotometry are commonly known to those skilled in these arts. Angiostatin peptides and angiostatin receptors peptides are also produced in recombinant E. coli or yeast expression systems, and purified with column chromatography.

Different peptide fragments of the intact angiostatin molecule can be synthesized for use in several applications including, but not limited to the following; as antigens for the development of specific antisera, as agonists and antagonists active at angiostatin binding sites, as peptides to be linked to, or used in combination with, cytotoxic agents for targeted killing of cells that bind angiostatin. The amino acid sequences that comprise these peptides are selected on the basis of their position on the exterior regions of the molecule and are accessible for binding to antisera. The amino and carboxyl termini of angiostatin, as well as the mid-region of the molecule are represented separately among the fragments to be synthesized.

These peptide sequences are compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules, thereby enhancing the potential for high specificity in the development of antisera, agonists and antagonists to angiostatin.

Angiostatin and angiostatin derived peptides can be coupled to other molecules using standard methods. The amino and carboxyl termini of angiostatin both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. Alternatively, tyrosine or lysine is added to fragments that do not have these residues to facilitate labeling of reactive amino and hydroxyl groups on the peptide. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Angiostatin peptides are chemically coupled to isotopes, enzymes, carrier proteins, cytotoxic agents, fluorescent molecules, chemiluminescent, bioluminescent and other compounds for a variety of applications. The efficiency of the coupling reaction is determined using different techniques appropriate for the specific reaction. For example, radiolabeling of an angiostatin peptide with $^{125}I$ is accomplished using chloramine T and $Na^{125}I$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted $Na^{125}I$ is separated from the labeled angiostatin peptide. The peptide fractions with the highest specific radioactivity are stored for subsequent use such as analysis of the ability to bind to angiostatin antisera.

Another application of peptide conjugation is for production of polyclonal antisera. For example, angiostatin peptides containing lysine residues are linked to purified bovine serum albumin using glutaraldehyde. The efficiency of the reaction is determined by measuring the incorporation of radiolabeled peptide. Unreacted glutaraldehyde and peptide are separated by dialysis. The conjugate is stored for subsequent use.

Antiserum against angiostatin, angiostatin analogs, peptide fragments of angiostatin and the angiostatin receptor can be generated. After peptide synthesis and purification, both monoclonal and polyclonal antisera are raised using established techniques known to those skilled in the art. For example, polyclonal antisera may be raised in rabbits, sheep, goats or other animals. Angiostatin peptides conjugated to a carrier molecule such as bovine serum albumin, or angiostatin itself, is combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4° C. and are centrifuged at approximately 2400×g at 4° C. for about 30 minutes. The serum is removed, aliquoted, and stored at 4° C. for immediate use or at −20° to −90° C. for subsequent analysis.

All serum samples from generation of polyclonal antisera or media samples from production of monoclonal antisera are analyzed for determination of antibody titer. Titer is established through several means, for example, using dot blots and density analysis, and also with precipitation of radiolabeled peptide-antibody complexes using protein A, secondary antisera, cold ethanol or charcoal-dextran followed by activity measurement with a gamma counter. The highest titer antisera are also purified on affinity columns which are commercially available. Angiostatin peptides are coupled to the gel in the affinity column. Antiserum samples are passed through the column and anti-angiostatin antibodies remain bound to the column. These antibodies are subsequently eluted, collected and evaluated for determination of titer and specificity.

The highest titer angiostatin antisera is tested to establish the following; a) optimal antiserum dilution for highest specific binding of the antigen and lowest non-specific binding, b) the ability to bind increasing amounts of angiostatin peptide in a standard displacement curve, c) potential cross-reactivity with related peptides and proteins, including plasminogen and also angiostatin of related species, d) ability to detect angiostatin peptides in extracts of plasma, urine, tissues, and in cell culture media.

Kits for measurement of angiostatin, and the angiostatin receptor, are also contemplated as part of the present invention. Antisera that possess the highest titer and specificity and can detect angiostatin peptides in extracts of plasma, urine, tissues, and in cell culture media are further examined to establish easy to use kits for rapid, reliable, sensitive, and specific measurement and localization of angiostatin. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. An angiostatin RIA is illustrated below. After successful radioiodination and purification of angiostatin or an angiostatin peptide, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4° C. for 24 hours, protein A is added and the tubes are vortexed, incubated at room temperature for 90 minutes, and centrifuged at approximately 2000–2500×g at 4° C. to precipitate the complexes of antibody bound to labeled antigen. The supernatant is removed by aspiration and the radioactivity in the pellets counted in a gamma counter. The antiserum dilution that binds approximately 10 to 40% of the labeled peptide after subtraction of the non-specific binding is further characterized.

Next, a dilution range (approximately 0.1 pg to 10 ng) of the angiostatin peptide used for development of the antiserum is evaluated by adding known amounts of the peptide to tubes containing radiolabeled peptide and antiserum. After an additional incubation period, for example, 24 to 48 hours, protein A is added and the tubes centrifuged, supernatant removed and the radioactivity in the pellet counted. The displacement of the binding of radiolabeled angiostatin peptide by the unlabeled angiostatin peptide (standard) provides a standard curve. Several concentrations of other angiostatin peptide fragments, plasminogen, angiostatin from different species, and homologous peptides are added to the assay tubes to characterize the specificity of the angiostatin antiserum.

Extracts of various tissues, including but not limited to primary and secondary tumors, Lewis lung carcinoma, cultures of angiostatin producing cells, placenta, uterus, and other tissues such as brain, liver, and intestine, are prepared using extraction technique that have been successfully employed to extract angiostatin. After lyophilization or Speed Vac of the tissue extracts, assay buffer is added and different aliquots are placed into the RIA tubes. Extracts of known angiostatin producing cells produce displacement curves that are parallel to the standard curve, whereas extracts of tissues that do not produce angiostatin do not displace radiolabeled angiostatin from the angiostatin antiserum. In addition, extracts of urine, plasma, and cerebrospinal fluid from animals with Lewis lung carcinoma are added to the assay tubes in increasing amounts. Parallel displacement curves indicate the utility of the angiostatin assay to measure angiostatin in tissues and body fluids.

Tissue extracts that contain angiostatin are additionally characterized by subjecting aliquots to reverse phase HPLC. Eluate fractions are collected, dried in Speed Vac, reconstituted in RIA buffer and analyzed in the angiostatin RIA. The maximal amount of angiostatin immunoreactivity is located in the fractions corresponding to the elution position of angiostatin.

The assay kit provides instructions, antiserum, angiostatin or angiostatin peptide, and possibly radiolabeled angiostatin and/or reagents for precipitation of bound angiostatin-angiostatin antibody complexes. The kit is useful for the measurement of angiostatin in biological fluids and tissue extracts of animals and humans with and without tumors.

Another kit is used for localization of angiostatin in tissues and cells. This angiostatin immunohistochemistry kit provides instructions, angiostatin antiserum, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This angiostatin immunohistochemistry kit permits localization of angiostatin in tissue sections and cultured cells using both light and electron microscopy. It is used for both research and clinical purposes. For example, tumors are biopsied or collected and tissue sections cut with a microtome to examine sites of angiostatin production. Such information is useful for diagnostic and possibly therapeutic purposes in the detection and treatment of cancer. Another method to visualize sites of angiostatin biosynthesis involves radiolabeling nucleic acids for use in in situ hybridization to probe for angiostatin messenger RNA. Similarly, the angiostatin receptor can be localized, visualized and quantitated with immunohistochemistry techniques.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Choice of an animal-tumor system in which growth of metastasis is inhibited by the primary tumor and is accelerated after removal of the primary tumor By screening a variety of murine tumors capable of inhibiting their own metastases, a Lewis lung carcinoma was selected in which the primary tumor most efficiently inhibited lung metastasis. Syngeneic C57Bl6/J six-week-old male mice were injected (subcutaneous dorsum) with $1 \times 10^6$ tumor cells. Visible tumors first appeared after 3–4 days. When tumors were approximately 1500 mm$^3$ in size, mice were randomized into two groups. The primary tumor was completely excised in the first group and left intact in the second group after a sham operation. Although tumors from 500 mm$^3$ to 3000 mm$^3$ inhibited growth of metastases, 1500 mm$^3$ was the largest primary tumor that could be safely resected with high survival and no local recurrence.

After 21 days, all mice were sacrificed and autopsied. In mice with an intact primary tumor, there were four +2 visible metastases, compared to fifty +5 metastases in the mice in which the tumor had been removed ($p < 0.0001$). These data were confirmed by lung weight, which correlates closely with tumor burden, as has been previously demonstrated. There was a 400% increase in wet lung weight in the mice that had their tumors removed compared to mice in which the tumor remained intact ($p < 0.0001$).

This experimental model gave reproducible data and the experiment described is reproducible. This tumor is labeled "Lewis lung carcinoma—low metastatic" (LLC-Low). The tumor also suppressed metastases in a nearly identical pattern in SCID mice, which are deficient in both B and T lymphocytes.

EXAMPLE 2

Isolation of a variant of Lewis lung carcinoma tumor that is highly metastatic, whether or not the primary tumor is removed A highly metastatic variant of Lewis lung carcinoma arose spontaneously from the LLC-Low cell line of Example 1 in one group of mice and has been isolated according to the methods described in Example 1 and repeatedly transplanted. This tumor (LLC-High) forms more than 30 visible lung metastases whether or not the primary tumor is present.

EXAMPLE 3

Size of metastases and proliferation rate of tumor cells within them. Effect of the primary tumor that inhibits metastases (LLC-Low)

C57Bl6/J mice were used in all experiments. Mice were inoculated subcutaneously with LLC-Low cells, and 14 days later the primary tumor was removed in half of the mice. At 5, 10 and 15 days after the tumor had been removed, mice were sacrificed. Histological sections of lung metastases were obtained. Mice with an intact primary tumor had micrometastases in the lung which were not neovascularized. These metastases were restricted to a diameter of 12–15 cell layers and did not show a significant size increase even 15 days after tumor removal. In contrast, animals from which the primary tumor was removed, revealed large vascularized metastases as early as 5 days after operation. These metastases underwent a further 4-fold increase in volume by the 15th day after the tumor was removed (as reflected by lung weight and histology). Approximately 50% of the animals who had a primary tumor removed died of lung metastases before the end of the experiment. All animals with an intact primary tumor survived to the end of the experiment.

Figure 3B:
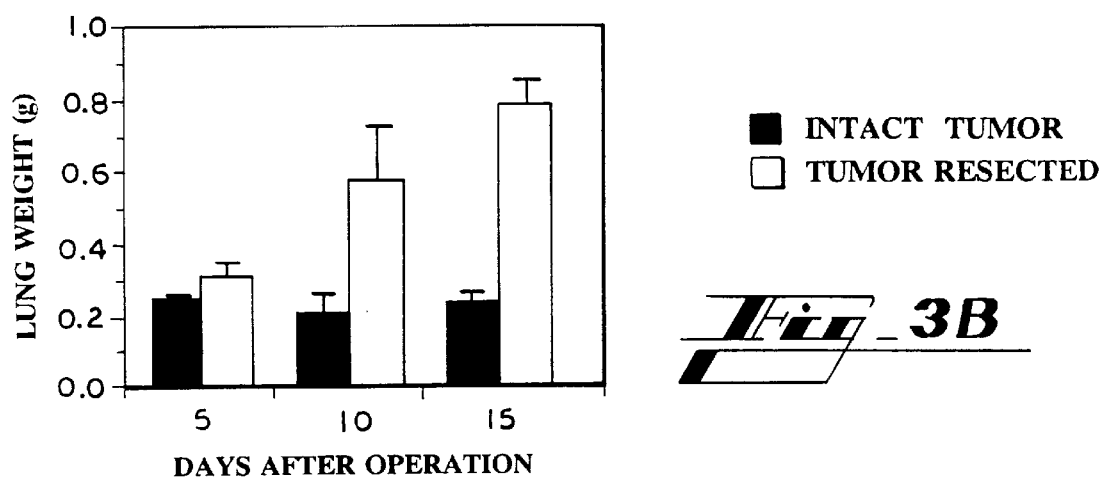

Replication rate of tumor cells within metastases was determined by counting nuclei stained with BrdU which had been previously injected into the mice. The high percentage of tumor cells incorporating BrdU in small, avascular metastases of animals with an intact primary tumor was equivalent to the BrdU incorporation of tumor cells in the large vascularized metastases of mice from which the primary tumor had been removed (FIG. 3). This finding suggests that the presence of a primary tumor has no direct effect on the replication rate of tumor cells within a metastasis.

In FIG. 3, the left panel shows BrdU labeling index of tumor cells in the lung in the presence or absence of a primary tumor. Before immunohistochemical staining, sections were permeabilized with 0.2M HCl for 10 minutes and digested with 1 µg/ml proteinase K (Boehringer Mannheim GmbH, Mannheim, Germany) in 0.2M Tris-HCl, 2 mM CaCl$_2$ at 37° C. for 15 minutes. Labeling index was estimated by counting percentage of positive nuclei at 250 power. The right panel of FIG. 3 depicts an analysis of total lung weight of tumors with primary tumors intact or removed 5, 10 and 15 days after operation. Animals were sacrificed 6 hours after intraperitoneal injection of BrdU (0.75 mg/mouse).

EXAMPLE 4

Inhibition of angiogenesis in lung metastases in the presence of an intact primary tumor To measure the degree of vascularization in lung metastases, tissues were stained with antibodies against von Willebrand factor (an endothelial specific marker, available from Dako Inc., Carpenteria, Calif.). Metastases from animals with intact tumors formed a thin cuff (8–12 tumor cell layers) around existing pulmonary vessels. Except for the endothelial cells of the vessel lining, no or few cells were positive for von Willebrand factor. In contrast, lung metastases of animals 5 days after removal of the primary tumor were not only larger but were also infiltrated with capillary sprouts containing endothelial cells which stained strongly for von Willebrand factor.

In immunohistochemical analysis of the presence of endothelial cells in lung metastases, a lung metastasis with the primary lung tumor intact 19 days after inoculation, had a cuff of tumor cells around a pre-existing microvessel in the lung. The metastasis was limited to 8 to 12 cell layers. There was no evidence of neovascularization around the microvessel, and it did not contain any new microvessels. This was typical of the maximum size of an avascular pre-angiogenic metastasis.

In an immunohistochemical analysis of tissue collected five days after the primary tumor was resected (19 days after inoculation of the primary tumor), the metastasis surrounded a pre-existing vessel in the lung. In contrast, in the sample where the primary tumor was not resected, the tumor was neovascularized. Thus, an intact primary tumor inhibits formation of new capillary blood vessels in metastases, but proliferation of tumor cells within a metastasis are not affected by the primary tumor.

EXAMPLE 5

A primary tumor inhibits angiogenesis of a second tumor implanted in the mouse cornea. Growth of this second tumor is inhibited A 0.25 to 0.5 mm² Lewis lung tumor (LLC-Low) was implanted in the mouse cornea on day 0. (Muthukkaruppan Vr., et al., Angiogenesis in the mouse cornea. *Science* 205:1416–1418, 1979). A primary tumor was formed by inoculating $1 \times 10^6$ LLC-Low cells subcutaneously in the dorsum, either 4 or 7 days before the corneal implant; or on the day of the corneal implant; or 4 or 7 days after the corneal implant. Control mice received the corneal implant but not the subcutaneous tumor. Other control mice received the corneal implant and an inoculation of LLC-High tumor cells in the dorsum 4 days before the corneal implant. The corneas were evaluated daily by slit-lamp stereomicroscopy for the growth of the corneal tumor (measured by an ocular micrometer) and for the growth of new capillary vessels from the edge of the corneal limbus.

In control mice not bearing a primary subcutaneous tumor, a majority of corneas (6/8) developed neovascularization starting at day 6 to 7 days after corneal implantation and continuing to day 10. By day 10, the vascularized corneal tumors had reached approximately a quarter of the volume of the whole eye. In the presence of the primary subcutaneous LLC-Low tumor, the corneal implants did not become vascularized if the primary tumor was in place by at least 4 days or more before the corneal implant (Table 1). In the absence of neovascularization, corneal tumors grew slowly as thin, white, avascular discs within the cornea.

However, if the primary tumor was not implanted until 4 days after the corneal implant, corneas became vascularized and 3/3 corneal tumors grew at similar rates as the non-tumor bearing controls. In the presence of the primary subcutaneous LLC-High tumor, the majority of corneas (2/3) developed neovascularization starting at day 7 after corneal implantation and continuing to day 10. By day 10, the vascularized corneal tumors again had reached approximately a quarter of the volume of the whole eye.

TABLE 1

Inhibition of tumor angiogenesis in the cornea by a primary subcutaneous tumor. [All primary tumors are LLC-Low except (*) which is LLC-High].

| Day of eye implant | 0 | 0 | 0 | 0 | 0 | 0 | 0 |
|---|---|---|---|---|---|---|---|
| Day of primary tumor implant | −7 | −4 | −4* | 0 | none | +4 | +7 |
| Number of mice with new corneal vessels at day 10 | 2/10 | 0/9 | 2/3 | 2/3 | 6/8 | 3/3 | 2/3 |

It would be expected that 0/10 corneas would show neovascularization when the primary LLC-Low subcutaneous tumor was implanted 7 days before the eye tumor implant (i.e.−7). However, 2 of the tumors (2/10) had become necrotic because they were too large (>3 cm³).

EXAMPLE 6

Primary intact tumor inhibits angiogenesis induced by a secondary subcutaneous implant of basic fibroblast growth factor (bFGF.)

Although the experiments described in Examples V and VI show that a primary tumor inhibits angiogenesis in a secondary metastasis, these studies do not reveal whether the primary tumor: (i) inhibits endothelial proliferation (or angiogenesis) directly, or (ii) indirectly by down-regulating the angiogenic activity of the metastatic tumor cells. To distinguish between these two possibilities, a focus of subcutaneous angiogenesis was induced by an implant of matrigel containing basic fibroblast growth factor (bFGF). (Passaniti A, et al., A simple, quantitative method for assessing angiogenesis and anti-angiogenic agents using reconstituted basement membrane, heparin and fibroblast growth factor. *Lab. Invest.* 67:519, 1992)

Figure 4:
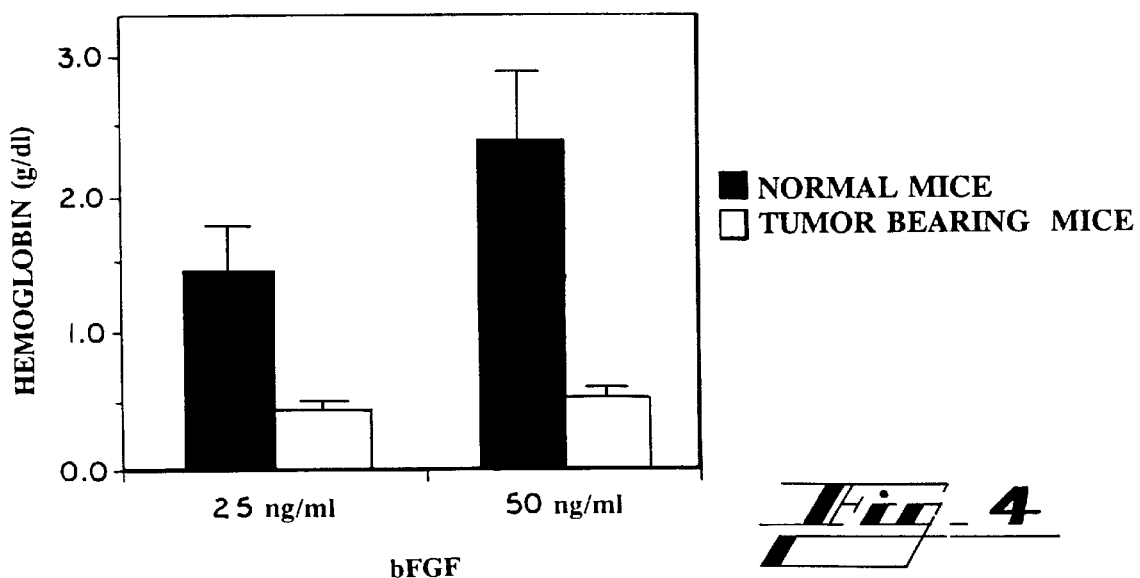
FIG. 4 shows Matrigel analysis of the influence of a Lewis lung primary tumor on bFGF driven angiogenesis in vivo.

Matrigel (an extract of basement membrane proteins), containing either 25 or 50 ng/ml bFGF in the presence of heparin, was injected subcutaneously on the ventral surface of normal and tumor-bearing mice (LLC-Low). Mice were sacrificed 4 days later and hemoglobin concentration in the gel was measured to quantify blood vessel formation. It has previously been shown that the number of new vessels which enter the matrigel is correlated with hemoglobin concentration. (Folkman J., Angiogenesis and its inhibitors in "*Important Advances in Oncology* 1985", V T DeVita, S. Hellman and S. Rosenberg, editors, J. B. Lippincott, Philadelphia 1985) Some gels were also prepared for histological examination. In normal mice, matrigel pellets which contained 50 ng/ml bFGF were completely red. They were heavily invaded by new capillary vessels, and contained 2.4 g/dl hemoglobin. Matrigel which lacked bFGF was translucent and gray and contained only 0.4 g/dl hemoglobin (a 6-fold difference). In contrast, matrigel from mice with a primary tumor contained only 0.5 g/dl (FIG. 4).

The near complete inhibition of angiogenesis in this experiment suggests that the presence of a Lewis lung primary tumor can inhibit bFGF-induced angiogenesis directly.

EXAMPLE 7

Transfer of serum from a tumor-bearing animal to an animal from which the primary tumor has been removed suppresses metastases Mice were implanted with Lewis lung carcinoma as described above. After 15 days, when tumors were approximately 1500 mm³, the mice were randomized into four groups. Three groups underwent complete surgical resection of the primary tumor; in one group the tumors were left in place (after a sham surgical procedure). The mice in the three resection groups then received daily intraperitoneal injections of saline, serum from normal nontumor bearing mice, or serum from mice with 1500 mm³ Lewis lung carcinomas. The group of mice with the tumors left intact received intraperitoneal saline injections. All mice were treated for 21 days, after which the animals were metastases wed lung metastases were counted (Table 2).

TABLE 2

| Treatment (Intraperitoneal Injections) | Primary Tumor Removed | | | Primary Tumor Intact |
|---|---|---|---|---|
| | Saline | Serum from normal mice | Serum from tumor-bearing mice | Saline Injections |
| Number of Lung Metastases: | 55 ± 5 | 50 ± 4 | 7 ± 2 | 3 ± 1 |

These results were confirmed by lung weight. p=<0.0001 for the difference between the two groups [(55 & 50) vs. (7 & 3)]. Similar results have been obtained using angiostatin from the urine of tumor-bearing animals.

EXAMPLE 8

Bovine capillary endothelial (BCE) cell assay

BCE cells are used between passages 9 and 14 only. At day 0, BCE cells are plated onto gelatinized (1.5 % gelatin in PBS at 37°, 10% $CO_2$ for 24 hours and then rinsed with 0.5 ml PBS) 24 well plates at a concentration of 12,500 cells/well. Cell counts are performed using a hemocytometer. Cells are plated in 500 μl DMEM with 10% heatinactivated (56° C. for 20 minutes) bovine calf serum and 1% glutamine-pen-strep (GPS).

BCE cells are challenged as follows: Media is removed and replaced with 250 µl of DMEM/5% BCS/1%GPS. The sample to be tested is then added to wells. (The amount varies depending on the sample being tested). Plates are placed at 37° C./10% $CO_2$ for approximately 10 minutes. 250 µl of DMEM/5% BCS/1% GPS with 2 ng/ml bFGF is added to each well. The final media is 500 µl of DMEM/5% BCS/1%GPS/ with 1 ng/ml bFGF. The plate is returned to 37° C./10% $CO_2$ incubator for 72 hours.

At day 4, cells are counted by removing the medium and then trypsinizing all wells (0.5 ml trypsin/EDTA) for 2 to 3 minutes. The suspended cells are then transferred to scintillation vials with 9.5 ml Hemetall and counted using a Coulter counter. A unit of activity is that amount of serum containing angiostatin that is capable of producing half-maximal inhibition of capillary endothelial proliferation when endothelial cells are incubated in bFGF 1 ng/ml for 72 hours.

EXAMPLE 9

Serum from mice bearing the low metastatic Lewis lung tumor (LLC-Low) inhibits capillary endothelial cell proliferation in vitro Bovine capillary endothelial cells were stimulated by basic fibroblast growth factor (bFGF 1 ng/ml), in a 72-hour proliferation assay. The serum of tumor-bearing mice added to these cultures inhibited endothelial cell proliferation in a dose-dependent and reversible manner. Normal serum was not inhibitory (FIG. 5). Endothelial cell proliferation was inhibited in a similar manner (relative to controls) by serum obtained from tumor-bearing nu/nu mice and SCID mice. After the primary tumor was removed, angiostatin activity disappeared from the serum by 3–5 days.

Tumor-bearing serum also inhibited bovine aortic endothelial cells and endothelial cells derived from a spontaneous mouse hemangioendothelioma, (Obeso, et al., "Methods in Laboratory Investigation, A Hemangioendothelioma-derived cell line; Its use as a Model for the Study of Endothelial Cell Biology," Lab Invest., 63(2), pgs 259–269, 1990) but did not inhibit Lewis lung tumor cells, 3T3 fibroblasts, aortic smooth muscle cells, mink lung epithelium, or W138 human fetal lung fibroblasts.

EXAMPLE 10

Serum from mice bearing the Lewis lung tumor (LLC-High) that does not inhibit metastases, does not inhibit capillary endothelial cell proliferation in vitro Serum from mice bearing a primary tumor of the LLC-High did not significantly inhibit proliferation of bFGF-stimulated bovine capillary endothelial cells relative to controls. Also, when this serum was subjected to the first two steps of purification (heparin-Sepharose chromatography and gel filtration), angiostatin activity was not found in any fractions.

EXAMPLE 11

Ascites from Lewis lung carcinoma (low metastatic), also generates angiostatin serum Mice received intraperitoneal injections of either LLC-Low or LLC-High tumor cells ($10^6$), and one week later, 1–2 ml of bloody ascites was obtained from each of 10–20 mice. Mesenteric tumor seeding was seen. The mice were then euthanized. Serum was obtained by cardiac puncture. Serum was also obtained from normal, non-tumor-bearing mice as a control. Serum and ascites were centrifuged to remove cells, and the supernate was assayed on bovine capillary endothelial cells stimulated by bFGF (1 ng/ml) (see Example IX). Ascites originating from both tumor types stimulated significant proliferation of capillary endothelial cells (e.g., 100% proliferation) over controls after 72 hours (FIG. 6). In contrast, serum from the low metastatic mice inhibited endothelial cell proliferation (inhibition to 79% of controls). The serum from the high metastatic line was stimulatory by 200%.

These data show that the ascites of the low metastatic line contains a predominance of endothelial growth stimulator over angiostatin. This condition is analogous to a solid primary tumor. Furthermore, angiostatin activity appears in the serum, as though it were unopposed by stimulatory activity. This pattern is similar to the solid primary tumor (LLC-Low). The ascites from the high metastatic tumor (LLC-High) also appears to contain a predominance of endothelial cell stimulator, but angiostatin cannot be identified in the serum.

EXAMPLE 12

Fractionation of angiostatin from serum by column chromatography and analysis of growth-inhibitory fractions by SDS-PAGE To purify the angiostatin(s), serum was pooled from tumor-bearing mice. The inhibitory activity, assayed according the above-described in vitro inhibitor activity assay, was sequentially chromatographed using heparin-Sepharose, Biogel AO.5 mm agarose, and several cycles of C4-reverse phase high performance liquid chromatography (HPLC). SDS-PAGE of the HPLC fraction which contained endothelial inhibitory activity, revealed a discrete band of apparent reduced $M_r$ of 38,000 Daltons, which was purified approximately 1 million-fold (see Table 3) to a specific activity of approximately $2 \times 10^7$. At different stages of the purification, pooled fractions were tested with specific antibodies for the presence of known endothelial inhibitors. Platelet factor-4, thrombospondin, or transforming growth factor beta, were not found in the partially purified or purified fractions.

TABLE 3

|  | Specific activity (units*/mg) | Fold purification |
| --- | --- | --- |
| Serum | 1.69 | 1 |
| Heparin Sepharose | 14.92 | 8.8 |
| Bio-gel AO.5m | 69.96 | 41.4 |
| HPLC/C4 | $2 \times 10^7$ | $1.2 \times 10^6$ |

*A unit of activity is that amount of serum containing angiostatin that is capable of producing half-maximal inhibition of capillary endothelial proliferation when endothelial cells are incubated in bFGF 1 ng/ml for 72 hours.

EXAMPLE 13

Fractionation of angiostatin from urine by column chromatography and analysis of growth-inhibitory fractions by SDS-PAGE Purification of the endothelial cell inhibitor(s) from serum is hampered by the small volume of serum that can be obtained from each mouse and by the large amount of protein in the serum.

Urine from tumor bearing mice was analyzed and found that it contains an inhibitor of endothelial cell proliferation that is absent from the urine of non-tumor bearing mice and from mice with LLC-high tumors. Purification of the endothelial cell inhibitory activity was carried out by the same strategy that was employed for purification of serum (described above) (FIG. 7).

FIG. 7 shows C4 reverse phase chromatography of partially purified serum or urine from tumor-bearing animals. All fractions were assayed on bovine capillary endothelial cells with bFGF in a 72-hour proliferation assay as described in Example IX. A discrete peak of inhibition was seen in both cases eluting at 30–35% acetonitrile in fraction 23. SDS-polyacrylamide gel electrophoresis of inhibitory fraction from the third cycle of C4 reverse phase chromatography of serum from tumor-bearing animals showed a single band at about 38,000 Daltons.

EXAMPLE 14
Characterization of circulating angiostatin

Endothelial inhibition was assayed according to the procedure described in Example 9. Angiostatin was isolated on a Synchropak HPLC C4 column. (Synchrom, Inc. Lafayette, Ind.) The inhibitor was eluted at 30 to 35% acetonitrile gradient. On a sodium dodecyl sulfate polyacrylamide gel electrophoresis (PAGE) gel under reducing conditions (b-mercaptoethanol(5% v/v), the protein band with activity eluted at 38 kilodaltons. Under non-reducing conditions, the protein with activity eluted at 28 kilodaltons. The activity is found at similar points whether the initial sample was isolated from urine or from serum. Activity was not detected with any other bands.

Activity associated with the bands was lost when heated (100° C. for 10 minutes) or treated with trypsin. When the band with activity was extracted with a water/chloroform mixture (1:1), the activity was found in the aqueous phase only.

EXAMPLE 15
Purification of inhibitory fragments from human plasminogen

Plasminogen lysine binding site I was obtained from Sigma Chemical Company. The preparation is purified human plasminogen after digestion with elastase. Lysine binding site I obtained in this manner is a population of peptides that contain, in aggregate, at least the first three triple-loop structures (numbers 1 through 3) in the plasmin A-chain (Kringle 1+2+3). (Sotrrup-Jensen, L., et al. in *Progress in Chemical Fibrinolysis and Thrombolysis*, Vol. 3, 191, Davidson, J. F., et al. eds. Raven Press, New York 1978 and Wiman, B., et al., *Biochemica et Biophysica Acta*, 579, 142 (1979)). Plasminogen lysine binding site I (Sigma Chemical Company, St. Louis, Mo.) was resuspended in water and applied to a C4-reversed phase column that had been equilibrated with HPLC-grade water/0.1% TFA. The column was eluted with a gradient of water/0.1% TFA to acetonitrile/0.1%. TFA and fractions were collected into polypropylene tubes. An aliquot of each was evaporated in a speed vac, resuspended with water, and applied to BCEs in a proliferation assay. This procedure was repeated two times for the inhibitory fractions using a similar gradient for elution. The inhibitory activity eluted at 30–35% acetonitrile in the final run of the C4 column. SDS-PAGE of the inhibitory fraction revealed 3 discrete bands of apparent reduced molecular mass of 40, 42.5, and 45 kd. SDS-PAGE under non-reducing conditions revealed three bands of molecular mass 30, 32.5, and 35 kd respectively.

EXAMPLE 16
Extraction of inhibitory activity from SDS-PAGE

Purified inhibitory fractions from human plasminogen based purifications were resolved by SDS-PAGE under non-denaturing conditions. Areas of the gel corresponding to bands seen in neighboring lanes loaded with the same samples by silver staining were cut from the gel and incubated in 1 ml of phosphate buffered saline at 4° C. for 12 hours in polypropylene tubes. The supernatant was removed and dialyzed twice against saline for 6 hours (MWCO= 6–8000) and twice against distilled water for 6 hours. The dialysate was evaporated by vacuum centrifugation. The product was resuspended in saline and applied to bovine capillary endothelial cells stimulated by 1 ng/ml basic fibroblast growth factor in a 72 hour assay. Protein extracted from each of the three bands inhibited the capillary endothelial cells.

EXAMPLE 17
Plasminogen Fragment Treatment Studies

Mice were implanted with Lewis lung carcinomas and underwent resections when the tumors were 1500–2000 $mm^3$. On the day of operation, mice were randomized into 6 groups of 6 mice each. The mice received daily intraperitoneal injections with the three purified inhibitory fragments of human plasminogen, whole human plasminogen, urine from tumor-bearing animals, urine from normal mice, or saline. One group of tumor-bearing animals that had only a sham procedure was treated with saline injections. Immediately after removal of the primary tumor, the mice receive an intraperitoneal injection of 24 µg (1.2 mg/kg/day/mouse) of the inhibitory plasminogen fragments as a loading dose. They then receive a daily intraperitoneal injections of 12 µg of the inhibitory fragment (0.6 mg/kg/day/mouse) for the duration of the experiment. Control mice receive the same dose of the whole plasminogen molecule after tumor removal. For the urine treatments, the urine of normal or tumor bearing mice is filtered, dialyzed extensively, lyophilized, and then resuspended in sterile water to obtain a 250 fold concentration. The mice are given 0.8 ml of the dialyzed urine concentrate, either from tumor bearing mice or normal mice, in two intraperitoneal injections on the day of removal of the primary tumor as a loading dose. They then receive daily intraperitoneal injections of 0.4 ml of the dialyzed and concentrated urine for the course of the experiment. Treatments were continued for 13 days at which point all mice were sacrificed and autopsied.

The results of the experiment are shown in FIGS. 8 and 9. FIG. 8 shows surface lung metastases after the 13 day treatment. Surface lung metastases refers to the number of metastases seen in the lungs of the mice at autopsy. A stereomicroscope was used to count the metastases. FIG. 8 shows the mean number of surface lung metastases that was counted and the standard error of the mean. As shown, the group of mice with the primary tumor present showed no metastases. The mice in which the primary tumor was resected and were treated with saline showed extensive metastases. The mice treated with the human derived plasminogen fragment showed no metastases. The mice treated with whole plasminogen showed extensive metastases indicating that the whole plasminogen molecule has no endothelial inhibitory activity. Those mice treated with dialyzed and concentrated urine from tumor bearing mice showed no metastases. Mice treated with concentrated urine from normal mice showed extensive metastases. When the weight of the lung was measured, similar results were obtained (FIG. 9).

EXAMPLE 18
Amino acid sequence of murine and human angiostatin

The amino acid sequence of angiostatin isolated from mouse urine and angiostatin isolated from the human lysine binding site I fragment preparation was determined on an Applied Biosystem Model 477A protein sequencer. Phenylthiohydantoin amino acid fractions were identified with an on-line ABI Model 120A HPLC. The amino acid sequence determined from the N-terminal sequence and the tryptic digests of the murine and human angiostatin indicate that the sequence of the angiostatin is similar to the sequence beginning at amino acid number 98 of murine plasminogen. Thus, the amino acid sequence of the angiostatin is a molecule comprising a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The beginning amino acid sequence of the murine angiostatin (SEQ ID NO:2) is shown in FIG. 1. The length of the amino acid sequence may be slightly longer or shorter than that shown in the FIG. 1.

N terminal amino acid analysis and tryptic digests of the active fraction of human lysine binding site I (See Example 15) show that the sequence of the fraction begins at approximately amino acid 97 or 99 of human plasminogen and the human angiostatin is homologous with the murine angiostatin. The beginning amino acid sequence of the human angiostatin (starting at amino acid 98) is shown in FIG. 2, (SEQ ID NO:3). The amino acid sequence of murine and human angiostatin is compared in FIG. 2 to corresponding internal amino acid sequences from plasminogen of other species including porcine, bovine, and Rhesus monkey plasminogen, indicating the presence of angiostatin in those species.

EXAMPLE 19

Expression of human angiostatin in *E. coli*

The pTrcHisA vector (Invitrogen) (FIG. 10) was used to obtain high-level, regulated transcription from the trc promoter for enhanced translation efficiency of eukaryotic genes in *E. coli*. Angiostatin is expressed fused to an N-terminal nickel-binding poly-histidine tail for one-step purification using metal affinity resins. The enterokinase cleavage recognition site in the fusion peptide allows for subsequent removal of the N-terminal histidine fusion peptide from the purified recombinant protein. The recombinant human angioststin protein was found to bind lysine; is cross-reactive with monoclonal antibodies specific for kringle regions 1, 2 and 3, and inhibits bFGF-driven endothelial cell proliferation in vitro.

To construct the insert, the gene fragment encoding human angiostatin is obtained from human liver mRNA which is reverse transcribed and amplified using the polymerase chain reaction (PCR) and specific primers. The product of 1131 base pairs encodes amino acids 93 to 470 of human plasminogen. The amplified fragment was cloned into the XhoI/KpnI site of pTrcHisA, and the resultant construct transformed into XL-1B (available from Stratagene) *E. coli* host cells. A control clone containing the plasmid vector pTrcHisA alone was transformed inot XL-1B *E. coli* host cells as well. This clone is referred to as the vector control clone. Both clones were purified identically as described below.

Expressing colonies were selected in the following manner. Colony lifts of *E. coli* transformed with the gene encoding angiostatin were grown on IPTG impregnated nitrocellulose filters and overlaid on an LB agar plate. Following IPTG induction of expression, colonies were lysed on nitrocellulose filters. The nitrocellulose lifts were blocked, rinsed and probed with two separate monoclonal antibodies (mAbs Dcd and Vap; gift of S. G. McCance and F. J. Castellino, University of Notre Dame) which recognize specific conformations of angiostatin. Strongly expressing colonies recognized by the mAbs were selected.

To identify the optimal time for maximal expression, cells were collected at various times before and after IPTG induction and exposed to repeated freeze-thaw cycles, followed by analysis with SDS-PAGE, immunoblotting and probing with mAbs Dcd and Vap.

From these, clone pTrcHisA/HAsH4 was selected. Induction with IPTG was for 4 hours after which the cell pellet was collected and resuspended in 50 mM Tris pH 8.0, 2 mM EDTA, 5% glycerol and 200 mg/ml lysozyme and stirred for 30 min. at 4° C. The slurry was centrifuged at 14,000 rpm for 25 min. and the pellet resuspended in 50 mM Tris pH 8.0, 2 mM EDTA, 5% glycerol and 0.1% DOC. This suspension was stirred for 1 hr. at 4° C., and then centrifuged at 14,000 rpm for 25 min. The supernatant fraction at this step contains expressed angiostatin. The *E. coli* expressed human angiostatin was found to possess the physical property of native angiostatin, that is the ability to bind lysine. The *E. coli* expressed angiostatin was thus purified over a lysine-sepharose (Pharmacia or Sigma) column in a single step. Elution of angiostatin from the column was with 0.2M epsilon-amino-n-caproic acid pH7.5.

Subsequent to these experiments, scale-up 10 L fermentation batches of clone pTrcHisA/HAsH4 was performed. The cells obtained from this scaled-up induction were pelleted and resuspended in50 mM Tris pH7.5, cracked at 10,000 psi thrice chilling at 10° C. in-between passes. The lysate obtained was clarified by centrifugation at 10,000 rpm for 30 min at 4° C., and expressed angiostatin isolated over lysine-sepharose (FIG. 11).

Purified *E. coli* expressed human angiostatin was dialysed exhaustively against water and lyophilized. The expressed human angiostatin was resuspended in media (DMEM, 5% BCS, 1% Gentamycin/ penicillin/streptomycin) to an estimated concentration of 3 ug/ml, and used in bovine capillary endothelial (BCE) cell assays in vitro, as described in EXAMPLE 8, pg.39. Similarly, the control clone containing the vector alone was treated in the identical fashion as the clone pTrcHisA/HAsH4. It was induced with IPTG identically, and the bacterial lysate used to bind lysine, eluted with 0.2M amino caproic acid, dialysed exhaustively and lyophilized. This control preparation was resuspended in media also at an estimated concentration of 3 ug/ml. The samples of recombinant angiostatin, and controls were obtained from different induction and fermentation batches as well as seperate purification runs, and were all coded at EntreMed, Maryland. BCE assays were performed with these coded samples in a blinded fashion at Children's Hospital, Boston.

The results of BCE assays of recombinant human angiostatin showed that human angiostatin expressed in *E.coli* inhibited the proliferation of BCE cells due to bFGF (used at 1 ng/ml) (FIG. 12). The stock recombinant angiostatin in media (at about 3 ug/ml) was used at a 1:5, 1:10 and 1:20 dilution. Percent inhibition was calculated as follows:

$$1 - \frac{\text{number of cells with angiostatin} - \text{number of cells at day 0}}{\text{number of cells with } bFGF \text{ alone} - \text{number of cells at day 0}}$$

The percent inhibition of BCE cell proliferation was comparable or higher to that of plasminogen derived angiostatin at similar concentrations. The results from a repeat run of the BCE assay are depicted in Fig. 13, where at a 1:5 dilution of the stock, recombinant angiostatin gave similar percent inhibitions to those obtained with plasminogen derived angiostatin. FIG. 13 shows the surprising result that human recombinant angiostatin protein inhibits over 60%, and as much as over 75% of BCE proliferation in culture.

Figure 14:
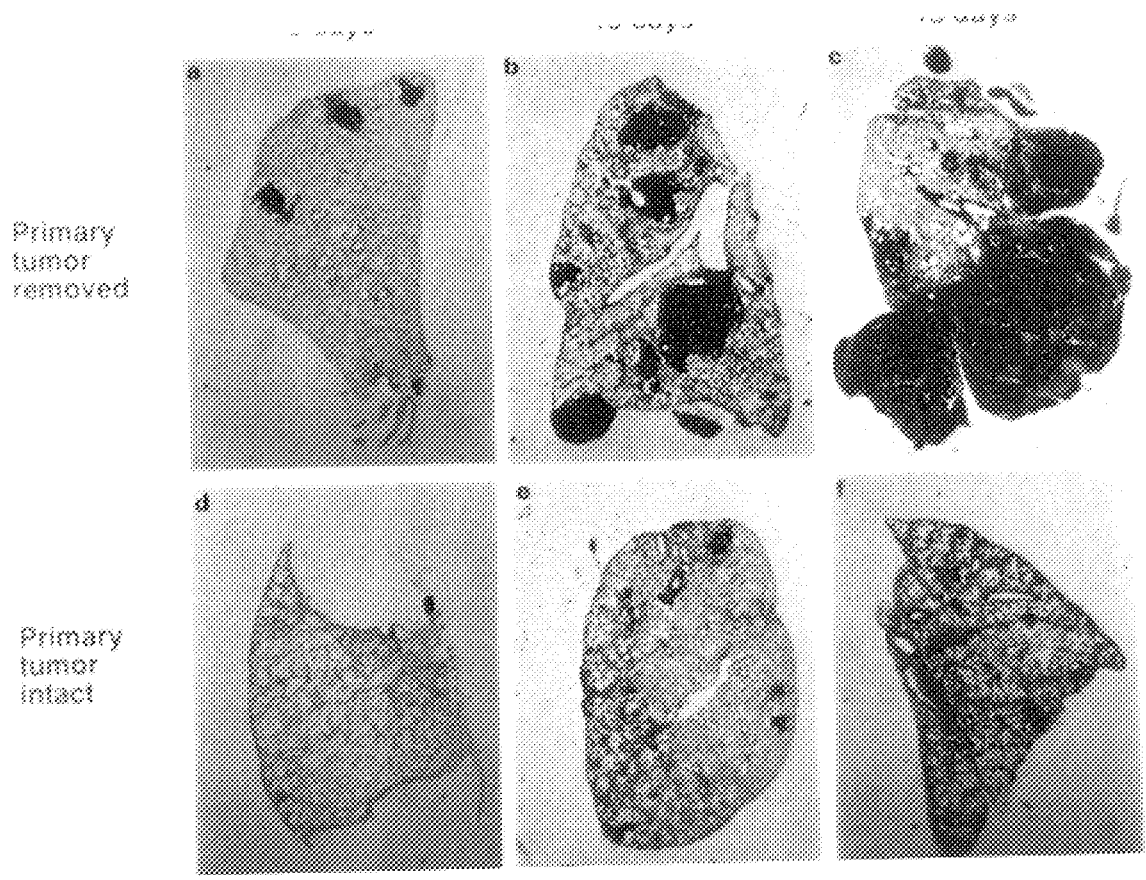
FIG. 14 shows the growth proliferation index and apoptotic index after removal of the primary tumor and treatment with saline or a fumagillin analogue with anti-angiogenic activity.

EXAMPLE 20
Angiostatin maintains dormancy of micrometastases by increasing the rate of apoptosis Following subcutaneous inoculation of C57 BL6/J mice with Lewis lung carcinoma cells ($1\times10^6$), primary tumors of approximately 1.5 cm$^3$ developed. Animals were subject to either surgical removal of the primary tumor or sham surgery. At 5, 10 and 15 days after surgery, mice were sacrificed and their lungs prepared for histological examination. Animals with resected primary tumors showed massive proliferation of micrometastases compared to sham operated controls (FIG. 14). These changes were accompanied by a significant increase in lung weight.

Figure 15A:
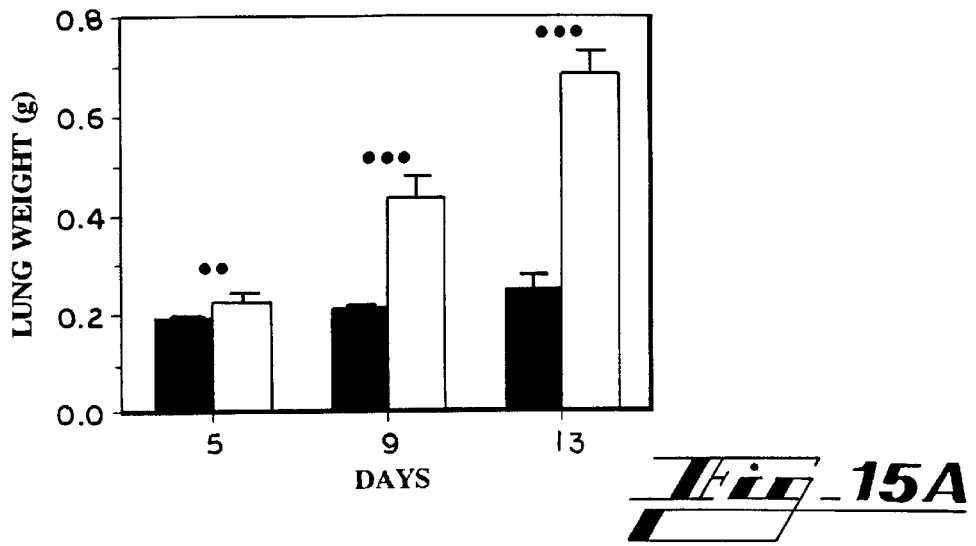
FIG. 15 shows the inhibition of growth of a T241 primary tumor in mice by treatment with human angiostatin in vivo with a single injection of 40 mg/kg/day.
Figure 15B:
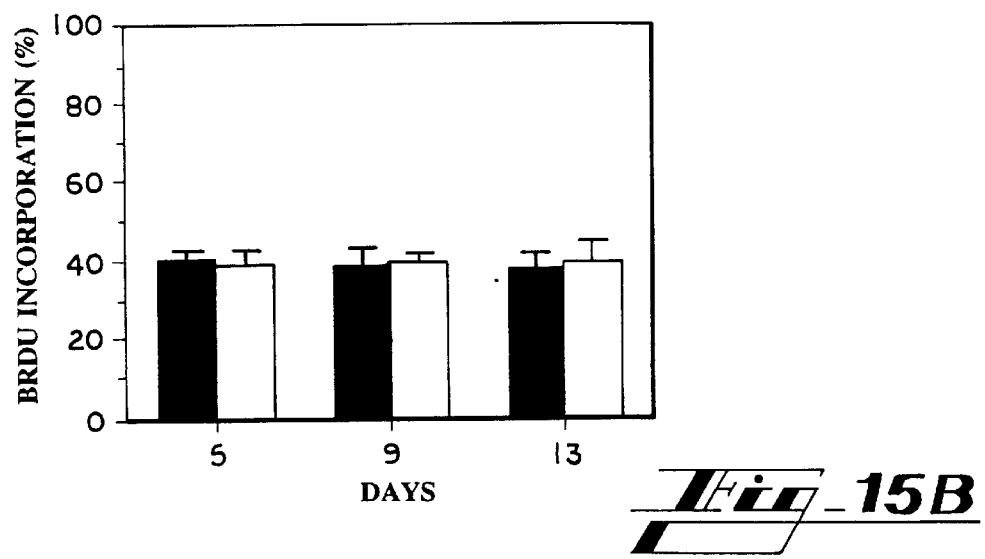
Figure 15C:
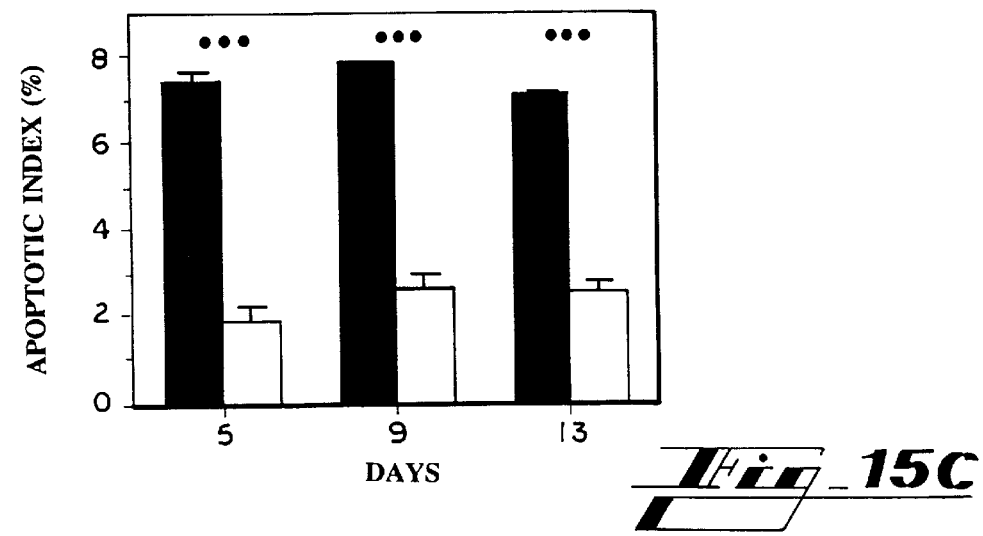

Analysis of tumor cell proliferation, as measured by uptake of bromo-deoxyuridine (BrdU) showed no differences between animals with intact primary tumors or resected tumors at 5, 9 and 13 days, indicating that the increase in tumor mass could not be explained by increased proliferation (FIG. 15). Accordingly, cell death was examined in these animals. Apoptosis, a process of cell death that is dependent on changes in gene expression and accounts for elimination of cells during development and in rapidly proliferating tissues such as the small intestine, was examined by immunohistochemically labeling fragmented DNA with the terminal deoxynucleotidyl transferase (TdT) technique. The apoptotic index was determined at each time of sacrifice. The removal of primary tumors caused a statistically significant increase (approximately 3 to 4 fold) in the apoptotic index at all times examined (FIG. 15).

Figure 16A:
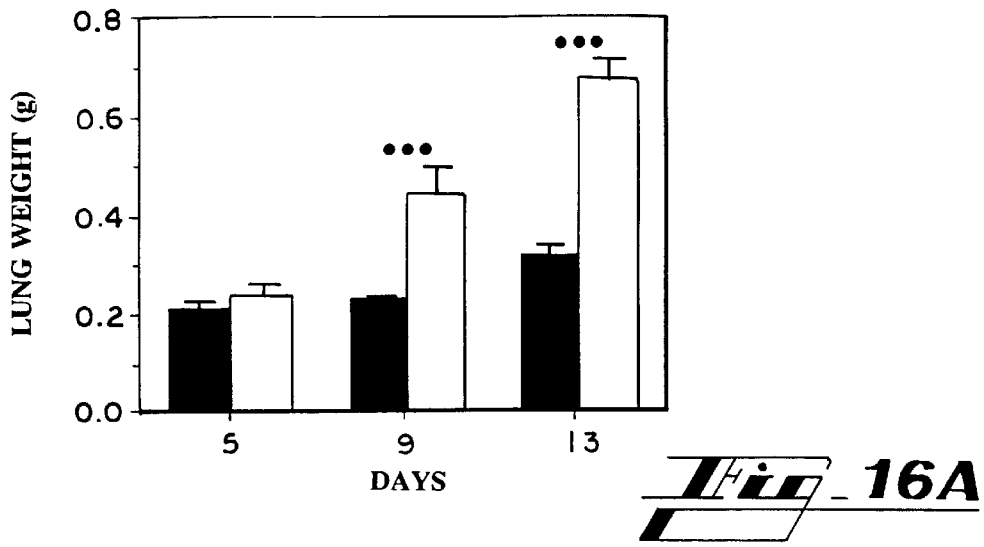
FIG. 16 shows the inhibition of growth of a LLC-LM primary tumor in mice by treatment with human angiostatin in vivo at two doses of 40 mg/kg per dose (80 mg/kg/day).
Figure 16B:
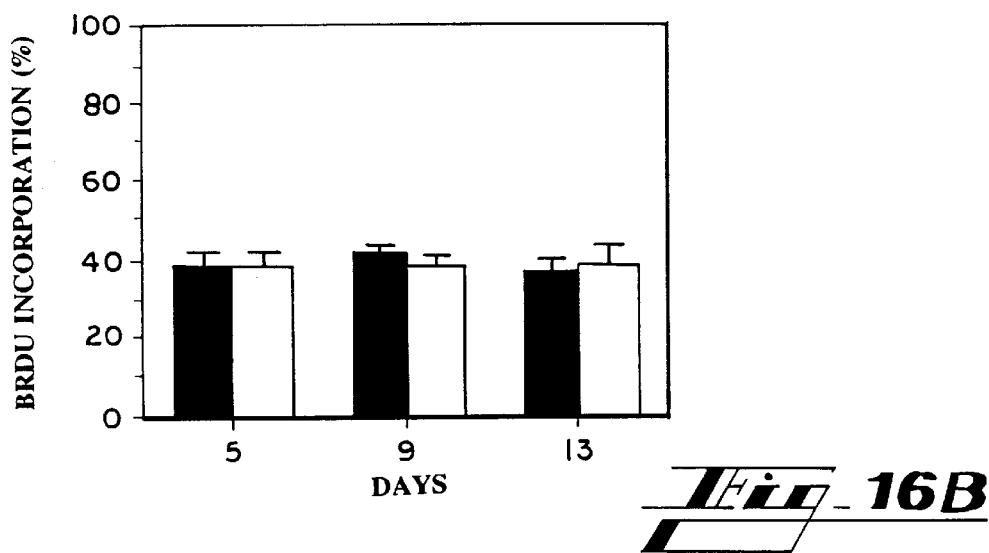
Figure 16C:
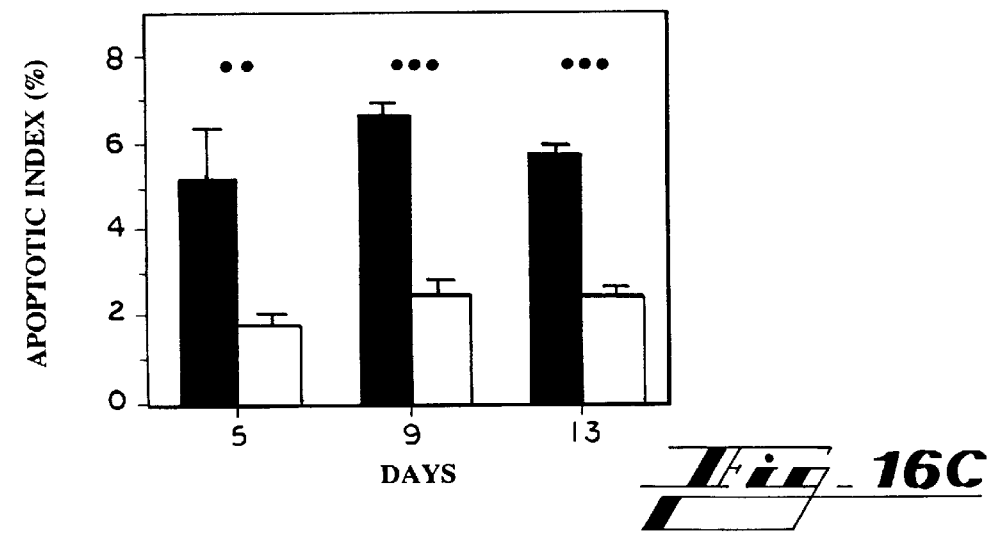

Supporting evidence was obtained by treating mice with removed primary tumors with an exogenous suppressor of angiogenesis. This substance, TNP-1470 (O-chloroacetylcarbamoyl fumagillol, previously named AGM-1470), is an analogue of fumagillin with reported anti-angiogenic activity. Subcutaneous injection of TNP-1470 (30 mg/kg every two days) produced results that were strikingly similar to those described above for animals that had intact primary tumors. These animals displayed a lower lung weight, equivalent proliferative index and increased apoptotic index compared to saline-injected controls (FIG. 16).

These data indicate that metastases remain dormant when tumor cell proliferation is balanced by an equivalent rate of cell death. The removal of the primary tumor causes a rapid increase in the growth of metastases, probably due to the removal of angiogenesis inhibitors (angiostatin) which control metastatic growth by increasing apoptosis in tumor cells. These effects are similar to those seen following removal of primary tumors and administration of an exogenous inhibitor of angiogenesis. Taken together, these data suggest that the primary tumor releases angiostatin which maintains dormancy of micrometastases.

EXAMPLE 21
Treatment of primary tumors with angiostatin in vivo

Angiostatin was purified from human plasminogen by limited elastase digestion as described in Example 15 above. Angiostatin was resuspended in phosphate-buffered saline for administration into six week old male C57Bl6/J mice. Animals were implanted subcutaneously with $1\times10^6$ tumor cells of either the Lewis lung carcinoma or T241 fibrosarcoma. Treatment with angiostatin is begun after four days when tumors are 80–160 mm$^3$ in size. Mice received angiostatin injections in either a single injection of 40 mg/kg or two 80 mg/kg injections via intraperitoneal (ip) or subcutaneous (sc) routes. Animals were sacrificed at various times after treatment extending to 19 days.

Angiostatin, administered at a daily dose of 40 mg/kg ip, produced a highly significant inhibition of the growth of T241 primary tumors (FIG. 17). This inhibitory effect on growth was visibly evident within 2 days and increased in magnitude throughout the time course of the study. By day 18, angiostatin-treated mice had tumors that were approximately 38% of the volume of the saline injected controls. This difference was statistically significant ($p<0.001$, Students t-test).

Angiostatin treatment (total dose of 80 mg/kg/day, administered twice daily at 40 mg/kg ip or sc) also significantly reduced the growth rate of LLC-LM primary tumors (FIG. 17). This inhibitory effect was evident at 4 days and increased in magnitude at all subsequent times examined. On the last day of the experiment (day 19), angiostatin-treated mice possessed a mean tumor volume that was only 20% of the saline-injected controls which was significantly different ($p<0.001$ Students t-test).

Figure 19:
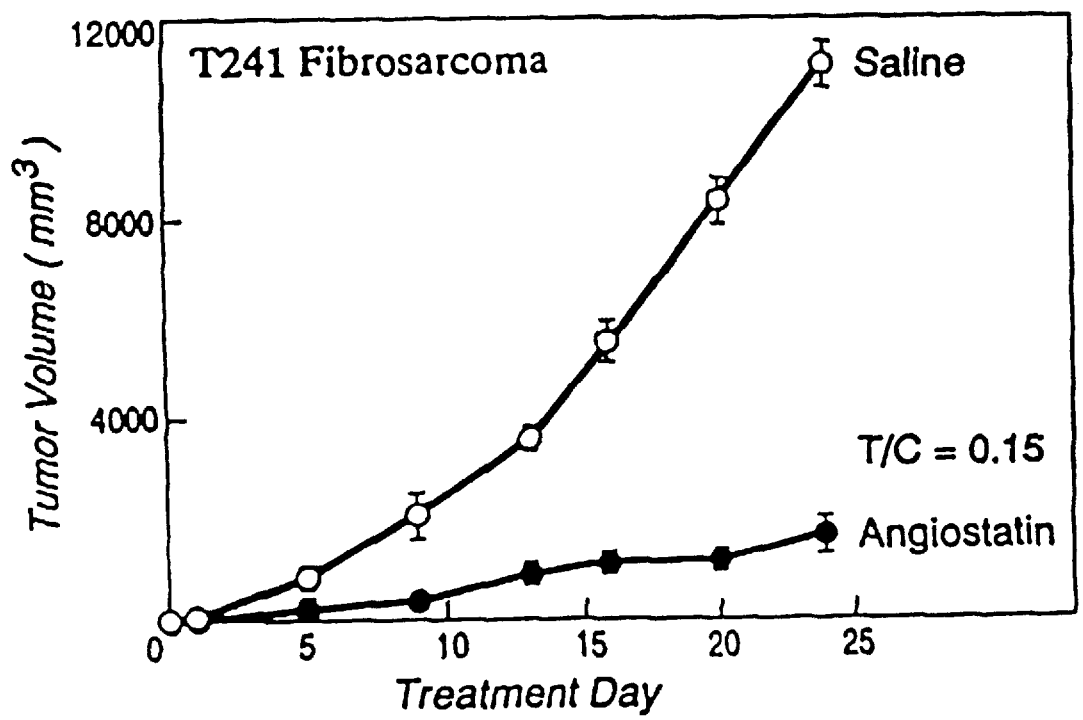
FIG. 19 shows the effect of administration of angiostatin protein to mice having implanted T241 fibrosarcoma cells on total tumor volume as a function of time.
Figure 20:
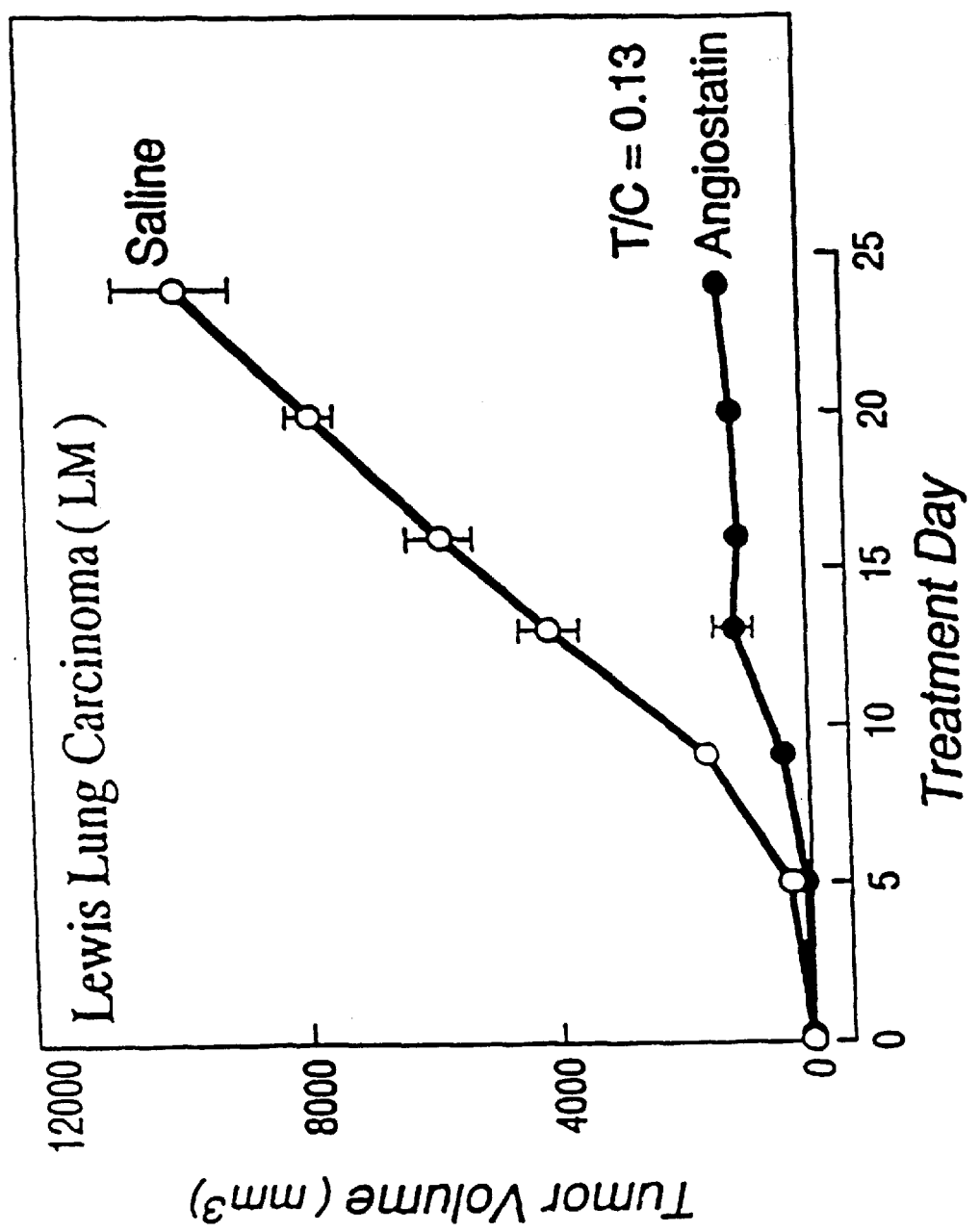
FIG. 20 shows the effect of administration of angiostatin protein to mice having implanted Lewis lung carcinoma (LM) cells on total tumor volume as a function of time.
Figure 21:
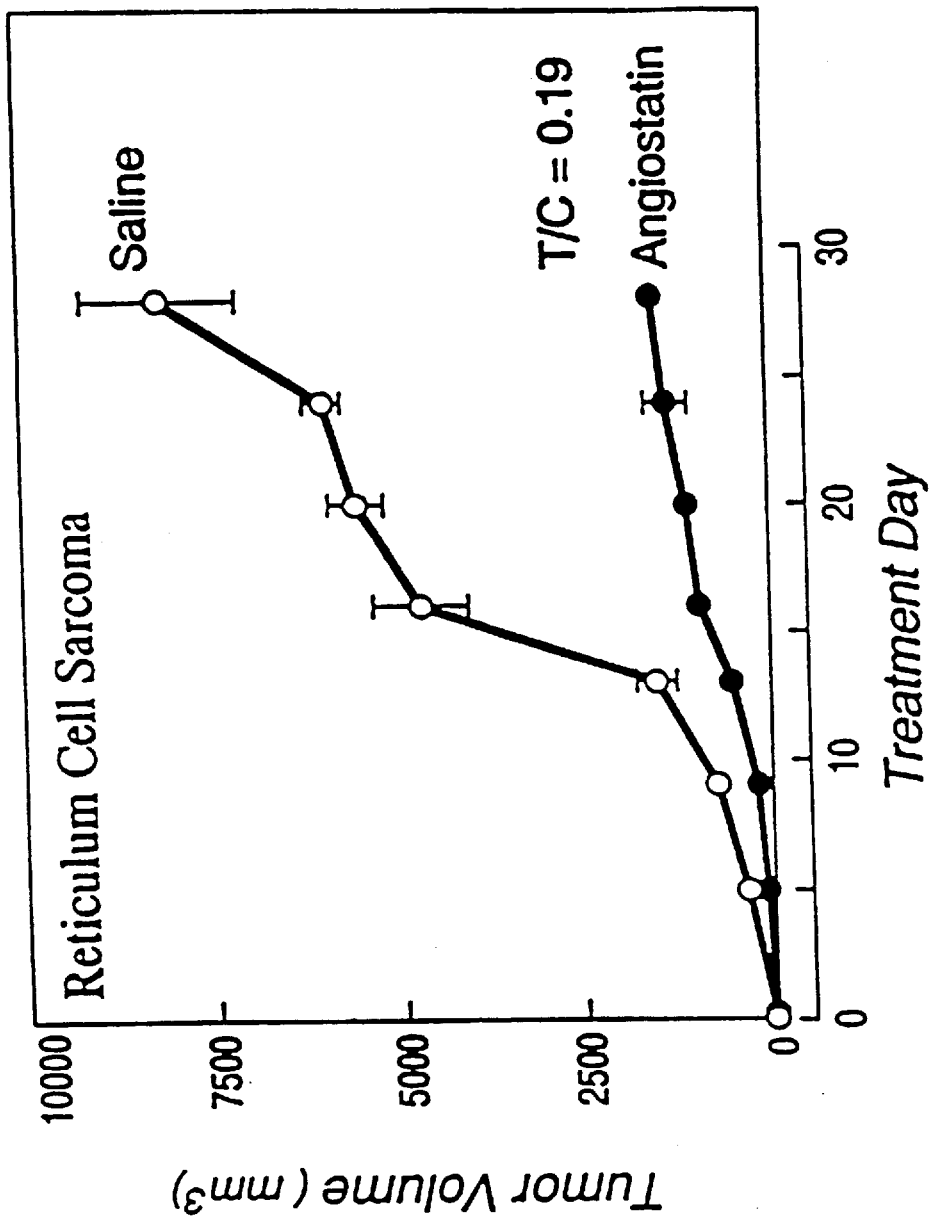
FIG. 21 shows the effect of administration of angiostatin protein to mice having implanted reticulum cell sarcoma cells on total tumor volume as a function of time.

In another series of experiments angiostatin was administered (50 mg/kg q12 h) to mice implanted with T241 fibrosarcoma, Lewis lung carcinoma (LM) or reticulum cell sarcoma cells. For each tumor cell type, the mice receiving angiostatin had substantially reduced tumor size. FIG. 19 demonstrates that for T241 fibrosarcoma, the angiostatin treated mice had mean tumor volumes that were only 15% of the untreated mice at day 24. FIG. 20 demonstrates that for Lewis lung carcinoma (LM), the angiostatin treated mice had mean tumor volumes that were only 13% of the untreated mice at day 24. FIG. 21 demonstrates that for reticulum sacroma, the angiostatin treated mice had mean tumor volumes that were only 19% of the untreated mice at day 24. The data represent the average of 4 mice at each time point.

These results demonstrate that angiostatin is an extremely potent inhibitor of the growth of three different primary tumors in vivo.

EXAMPLE 22
Treatment of human cell-derived primary tumors in mice with angiostatin in vivo The effect of angiostatin on two human tumor cell lines, human prostate carcinoma PC-3 and human breast carcinoma MDA-MB, was studied. Immunodeficient SCID mice were implanted with human tumor cells, and the mice treated with 50 mg/kg angiostatin every 12 hours essentially as described in Example 21. The results demonstrate that the angiostatin protein of the present invention is a potent inhibitor of human tumor cell growth. FIG. 22 shows that for human prostate carcinoma PC-3, the angiostatin treated mice had only 2% of the mean tumor volume compared to the untreated control mice at day 24. FIG. 23 shows that for human breast carcinoma MDA-MB, he angiostatin treated mice had only 8% of the mean tumor volume compared to the untreated control mice at day 24.

EXAMPLE 23
Gene Therapy—Effect of transfection of the angiostatin gene on tumor volume A 1380 base pair DNA sequence for angiostatin derived from mouse plasminogen cDNA (obtained from American Type Culture Collection (ATCC)), coding for mouse plasminogen amino acids 1–460, was generated using PCR and inserted into an expression vector. The expression vector was transfected into T241 fibrosarcoma cells and the transfected cells were implanted into mice. Control mice received either non-transfected T241 cells, or T241 cells transfected with the vector only (i.e. non-angiostatin expressing transfected cells). Three angiostatin-expressing transfected cell clones were used in the experiment. Mean tumor volume determined over time. The results show the surprising and dramatic reduction in mean tumor volume in mice for the angiostatin-expressing cells clones as compared with the non-transfected and non-expressing control cells.

Figure 24:
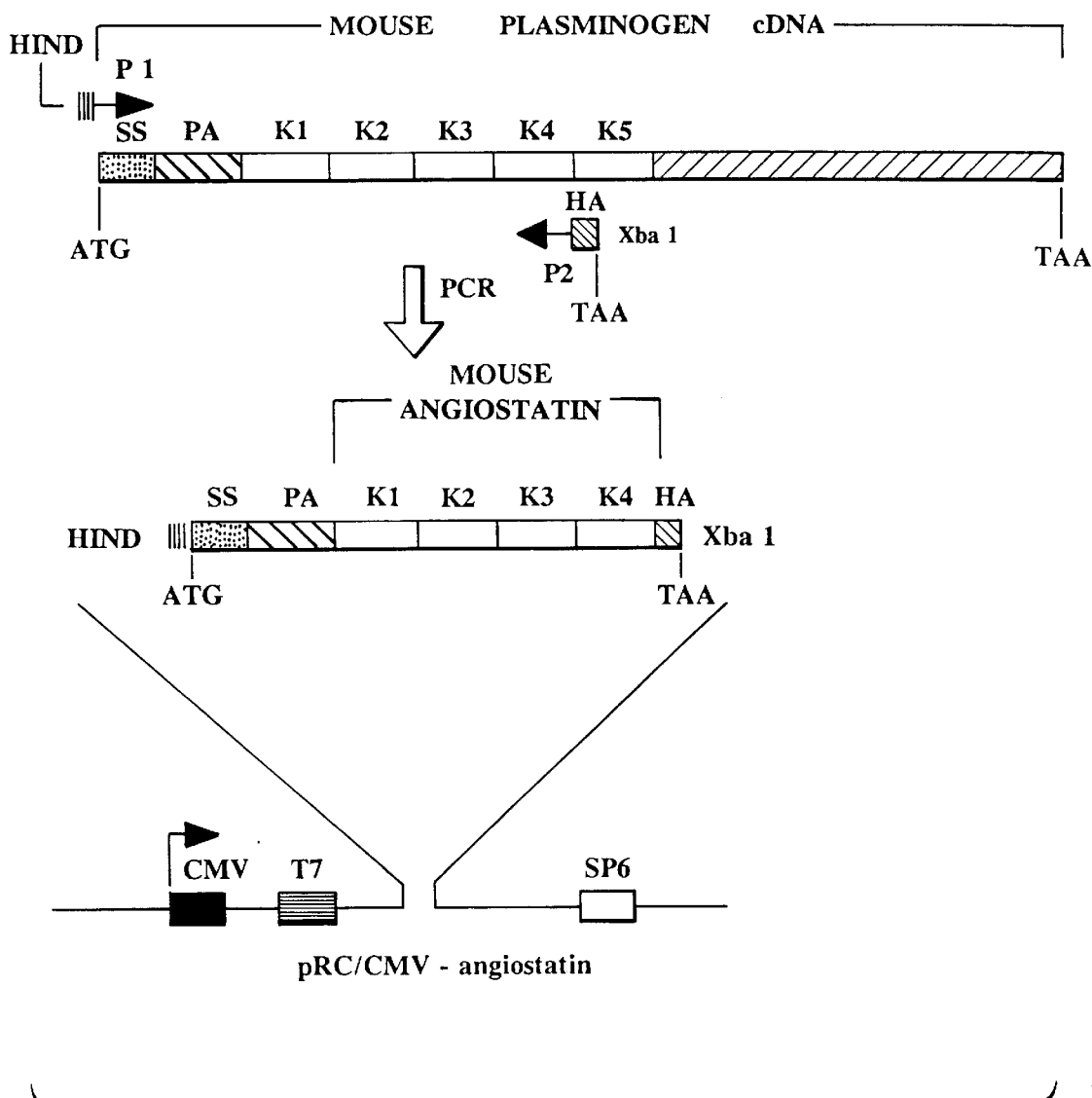
FIG. 24 is a schematic representation of cloning of the mouse DNA sequence coding for mouse angiostatin protein derived from mouse plasminogen cDNA. The mouse angiostatin encompasses mouse plasminogen kringle regions 1–4. PCR means polymerase chain reaction; P1 is the 5'-end oligonucleotide primer for PCR; P2 is the 3'-end oligonucleotide primer for PCR; SS designates the signal sequence; ATG is the translation initiation codon; TAA is the translation stop codon; HA represents the hemagglutinin epitope tag (YPYDVPDYASL); K1, K2, K3 and K4 represent mouse plasminogen kringle regions 1, 2, 3 and 4 respectively. CMV is the cytomegalovirus promoter; T7 is the bacteria phage promoter; PA represents pre-activation peptides; and SP6 is the Sp 6 promoter.

The mouse DNA sequence coding for mouse angiostatin protein is derived from mouse plasminogen cDNA. The mouse angiostatin encompasses mouse plasminogen kringle regions 1–4. The schematic for constructing this clone is shown in FIG. 24.

The mouse angiostatin protein clones were transfected into T241 fibrosarcoma cells using the LIPOFECTIN™ transfection system (available from Life Technologies, Gaithersburg, Md.). The LIPOFECTINT™ reagent is a 1:1 (w/w) liposome formulation of the cationic lipid N-[1-(2,3-dioleyloxy)propyl]-n,n,n-trimethylammonium chloride (DOTMA), and diolecoyl phosphotidylethanolamine (DOPE) in membrane filtered water.

The procedure for transient transfection of cells is as follows:

1. T241 cells are grown in 60 $cm^2$ tissue culture dishes, seed ~1–2×$10^5$ cells in 2 ml of the appropriate growth medium supplemented with serum.
2. Incubate the cells at 37° C. in a $CO_2$ incubator until the cells are 40–70% confluent will usually take 18–24 h, but the time will vary among cell types. The T241 tumor cells confluency was approximately 70%.
3. Prepare the following solutions in 12×75 mm sterile tubes:
   Solution A: For each transfection, dilute 5 μg of DNA in 100 μl of serum-free OPTI-MEM I Reduced Serum Medium (available from Life Technologies) (tissue culture grade deionized water can also be used).
   Solution B: For each transfection, dilute 30 μg of LIPO-FECTIN in 100 μl OPTI-MEM medium.
4. Combine the two solutions, mix gently, and incubate at room temperature for 10–15 min.
5. Wash cells twice with serum-free medium.
6. For each transfection, add 0.8 ml serum-free medium to each tube containing the LIPOFECTIN™ reagent-DNA complexes. Mix gently and overlay the complex onto cells.
7. Incubate the cells for approximately 12 h at 37° C. in a $CO_2$ incubator.
8. Replace the DNA containing medium with 1 mg/ml selection medium containing serum and incubate cells at 37° C. in a $CO_2$ incubator for a total of 48–72 h. 9. Assay cell extracts for gene activity at 48–72 h post transfection.

Transfected cells can be assayed for expression of angiostatin protein using angiostatin-specific antibodies. Alternatively, after about 10–14 days, G418 resistant colonies appeared in the CMV-angiostatin transfected T241 cells. Also, a number of clones were seen in the vector alone transfected clones but not in the untransfected clones. The G418 resistant clones were selected for their expression of angiostatin, using a immunofluorence method.

Interestingly, the in vitro cell growth T241 cells and Lewis lung cells transfected with angiostatin was not inhibited or otherwise adversely affected, as shown in FIGS. 25 and 26.

Figure 27:
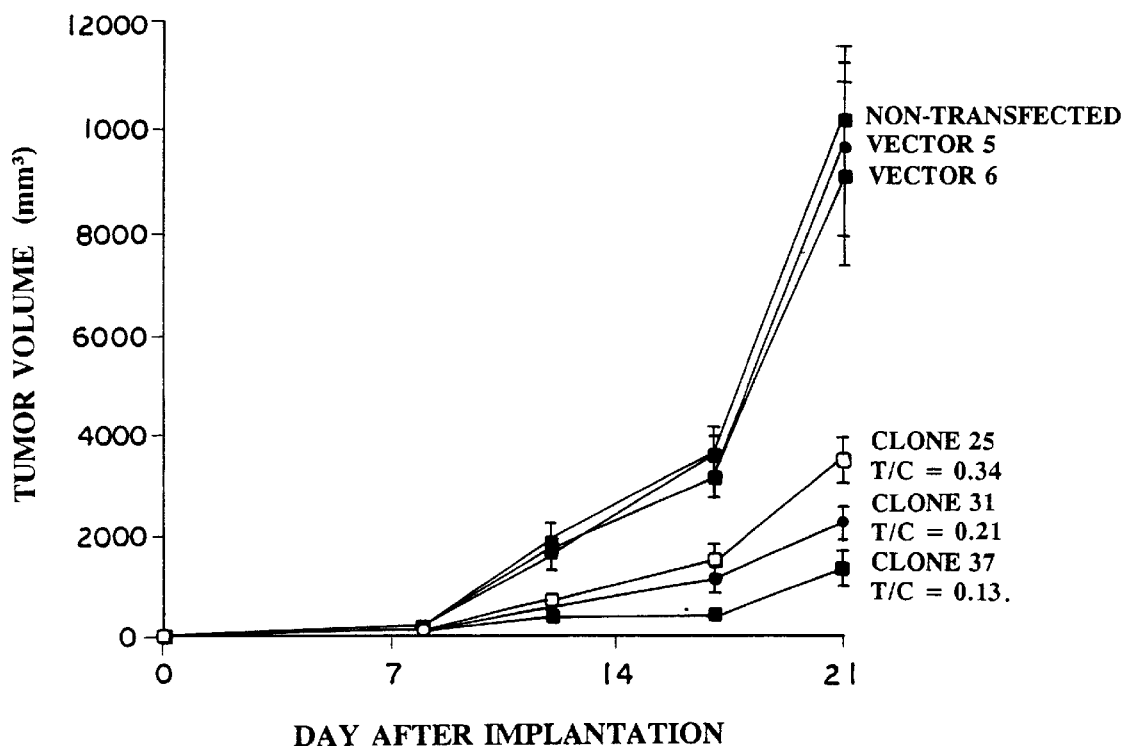
FIG. 27 shows the effect on total tumor volume as a function of time of implanting T241 fibrosarcoma cells in mice, where the fibrosarcoma cells have been transfected with a vector containing a DNA sequence coding for angiostatin protein, and where the vector is capable of expressing angiostatin protein. "Non-transfected" represents unaltered T241 fibrosarcoma cells implanted in mice. "Vector 6" represents T241 fibrosarcoma cells transfected with the vector only, which does not contain the DNA sequence coding for angiostatin protein, implanted in mice. "Clone 25, Clone 31 and Clone 37" represent three angiostatin-producing clones of T241 fibrosarcoma cells transfected with a vector containing the DNA sequence coding for angiostation protein implanted in mice.

FIG. 27 depicts the results of the transfection experiment. All three of the angiostatin-expressing T241 transfected clones produced mean tumor volumes in mice that were substantially reduced relative to the tumor volume in control mice. The mean tumor volume of the mice implanted with Clone 37 was only 13% of the control, while Clone 31 and Clone 25 tumor volumes were only 21% and 34% of the control tumor volumes, respectively. These results demonstrate that the DNA sequences coding for angiostatin can be transfected into cells, that the transfected DNA sequences are capable of expressing angiostatin protein by implanted cells, and that the expressed angiostatin functions in vivo to reduce tumor growth.

EXAMPLE 24

Localization of in vivo site of angiostatin expression

To localize the in vivo site of expression of angiostatin protein, total RNA from various cell types, Lewis lung carcinoma cells (mouse), T241 fibrosarcoma (mouse), and Burkitt's lymphoma cells (human), both from fresh tumor or cell culture after several passages were analysed to determine the presence of angiostatin transcripts. Northern analysis of samples showed an absence of any signal hybridizing with the sequence from all samples except that of normal mouse liver RNA showing a single signal of approximately 2.4 kb corresponding to mouse plasminogen. Northern analysis of human samples show an absence of any signal hybridizing with human angiostatin sequence from all samples except that of normal human liver RNA showing a single signal of approximately 2.4 kb corresponding to human plasminogen.

Reverse transcription polymerase chain reaction (RT-PCR) analysis showed an absence of any product from all samples probed with mouse angiostatin sequences except that of the normal mouse liver. RT-PCR analysis showed an absence of any product from all human samples probed with human angiostatin sequences except that of the normal human liver (expected size of 1050 bp for mouse and 1134 bp for human).

Thus it appears that mouse angiostatin transcripts (assuming identity with amino acids 97 to 450 of mouse plasminogen) are not produced by all the above mouse samples and human angiostatin transcripts (assuming identity with amino acids 93 to 470 of human plasminogen) are not produced by the above human samples. The positive signals obtained in normal mouse/human liver is from hybridization with plasminogen.

EXAMPLE 25

Expression of Angiostatin in Yeast

The gene fragment encoding amino acids 93 to 470 of human plasminogen was cloned into the XhoI/EcoRI site of pHIL-SI(Invitrogen) which allows the secreted expression of proteins using the PHOI secretion signal in the yeast *Pichia pastoris*. Similarly, the gene fragment encoding amino acids 93 to 470 of human plasminogen was cloned into the SnaBI/EcoRI site of pPIC9 (Invitrogen) which allows the secreted expression of proteins using the a-factor secretion signal in the yeast *Pichia pastoris*. The expressed human angiostatin proteins in these systems will have many advantages over those expressed in *E. coli* such as protein processing, protein folding and posttranslational modification inclusive of glycosylation.

Expression of gene in *P. pastoris*: is described in ) Sreekrishna, K. et al. (1988) High level expression of heterologous proteins in methylotropic yeast *Pichia pastoris*. J. Basic Microbiol. 29 (4): 265–278, and Clare, J. J. et al. (1991) Production of epidermal growth factor in yeast: High-level secretion using *Pichia pastoris* strains containing multiple gene copies, Gene 105:205–212, both of which are hereby incorporated herein by reference.

EXAMPLE 26

Expression of angiostatin proteins in transgenic animals and plants

Transgenic animals such as of the bovine or procine family are created which express the angiostatin gene transcript. The transgenic animal express angiostatin protein for example in the milk of these animals. Additionally edible transgenic plants which express the angiostatin gene transcript are constructed.

Constructing transgenic animals that express foreign DNA is described in Smith H. Phytochrome transgenics: functional, ecological and biotechnical applications, Semin. Cell. Biol. 1994 5(5):315–325, which is hereby incorporated herein by reference.

EXAMPLE 27

Production and administration of aggregate angiostatin

This example demonstrates the production and administration of aggregate angiostatin to inhibit endothelial cell proliferation and tumor growth. Normally, it is assumed that recombinant proteins produced from *E. coli* need to be solubilized and re-folded (renatured, reduced and alkylated) to achieve in vivo activity. In the process, a significant amount of the protein is often lost. In this example, aggregate recombinant angiostatin is produced after purification and used directly, without further renaturing, reducing or alkylating, to inhibit angiogenesis and tumor growth. Therefore, this example provides a surprisingly efficient means of producing and using angiostatin. This aggregate angiostatin and method of delivery also provides a means of sustained release of angiostatin, thereby optimizing its efficiency. As used herein "aggregate angiostatin" means angiostatin that has been substantially purified, but not re-folded, as described in more detail below.

Expression of Angiostatin

The *E. coli* expression system, which has the advantage of being fast, productive, and inexpensive, was used for the expression of mouse angiostatin. Two oligo primers, flanking a cDNA sequence of plasminogen kringles 1–4 (plasminogen cDNA was purchased from ATCC), were designed for a PCR based strategy of constructing the angiostatin expression system. (See, for example, Menhart, N., Shel, L. C., Kelly, R. F., and Castellino, F. J. (1991) *Biochem.* 30, 1948–1957); Marti, D., Schaller, J., Ochensberger, B., and Rickli, E. E. (1994) *Eur. J. Biochem.* 219, 455–462; Söhndel, S., Hu, C.-K., Marti, D., Affolter, M., Schaller, J., Llinas, M., and Rickli, E. E. (1996) *Biochem.* in press; Rejante, M. R., Byeon, I.-J. L., and Llinas, M. (1991) *Biochem.* 30, 11081–11092) The PCR product was inserted into the Nco I and Xho I sites of pET22 vector (Novegen), which contains T7 lac promoter and an oligohistidine sequence. The cDNA was then transformed into *E. coli* (strain BL21(DE3)),which contains a chromosomal copy of the T7 RNA polymerase gene under lacUV5 control. The expression of the recombinant angiostatin was induced by the addition of IPTG. The expressed angiostatin accumulated as inclusion bodies in the host cells and typically consisted of over 40% of total cellular protein, as estimated by Coomassie blue staining.

The invention contemplates that a recombinant angiostatin, or fragment thereof, derived from any appropriate species can be expressed in a variety of vector and host systems, well-known to those skilled in the art.

Purification and Aggregation of Angiostatin

Figure 28:
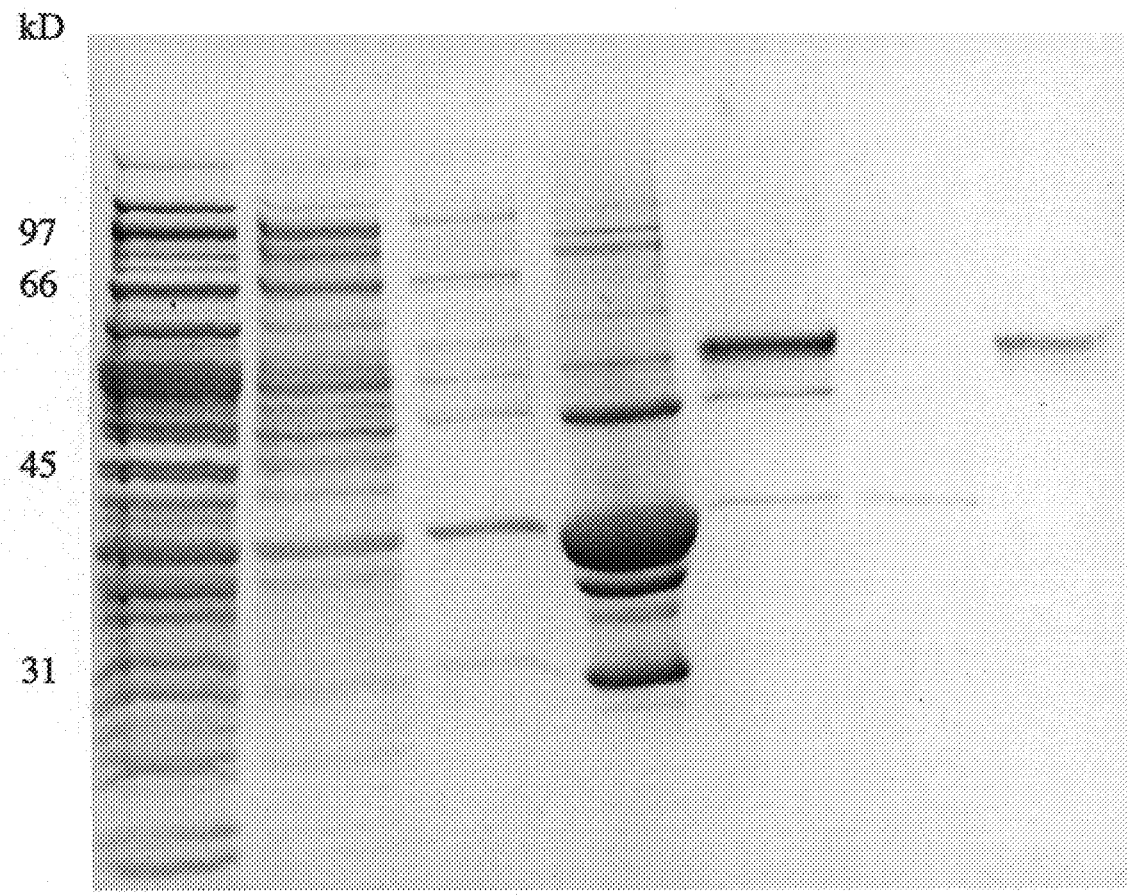
FIG. 28 shows a reducing polyacrylimide gel electrophoresis photograph (SDS-PAGE) of recombinant mouse angiostatin at various stages of purification and aggregation under nickel affinity column chromatography (lanes 1–3 inclusion body washes, lane 4 insoluble fraction in urea, lane 5 affinity column starting materials, lane 6 column flow through, lane 7 elutant angiostatin).

The insoluble fraction of the sonicated host cells containing the inclusion bodies was purified by centrifugation at 9,000 rpm for 25 minutes, and repeated washing. The resulting product contained about 80% angiostatin, as estimated by Coomassie blue staining. The N-terminal oligohistidine domain of the fusion protein made it possible for convenient and economical purification of the recombinant angiostatin with chelating affinity chromatography in a $Ni^{2+}$-NTA agarose column (1.5 cm ×5 cm) under denaturing conditions, by dissolving the inclusion bodies in 6M urea. As seen in FIG. 28, lane 7, the purified angiostatin shows a single band on SDS-PAGE by Coomassie blue staining, with a migration rate at between about 45 kD to 65 kD, and more preferably about 55 kD. This single step chromatography can purify the protein to substantial homogeneity, however, the invention contemplates that a variety of other purification techniques well-known to those skilled in the art can be employed to achieve this product.

The protein, in its elution buffer, was then dialyzed (15,000 MWCO) against phosphate buffered saline (PBS) for 24 hours with 3 changes of the dialysate at 4° C. During dialysis, a white precipitate was seen. The sample was then removed from the dialysis bags and the precipitate removed by centrifugation. The precipitate was then resuspended, using a vortex, in PBS to form a fine suspension for use in the animal models, or stored at −20° C. This precipitate provided the aggregate angiostatin. Alternatively, 20 mM tris-HCl pH 7.9/ 150 mM NaCl can be used as a dialysis buffer, for example. The invention contemplates that either more or less dialysis and a variety of other dialysis buffers may be utilized to yield a corresponding amount of aggregate angiostatin, within limitations routinely determinable by one skilled in the art, in view of the present disclosure.

In vitro tests of aggregate angiostatin

Figure 29:
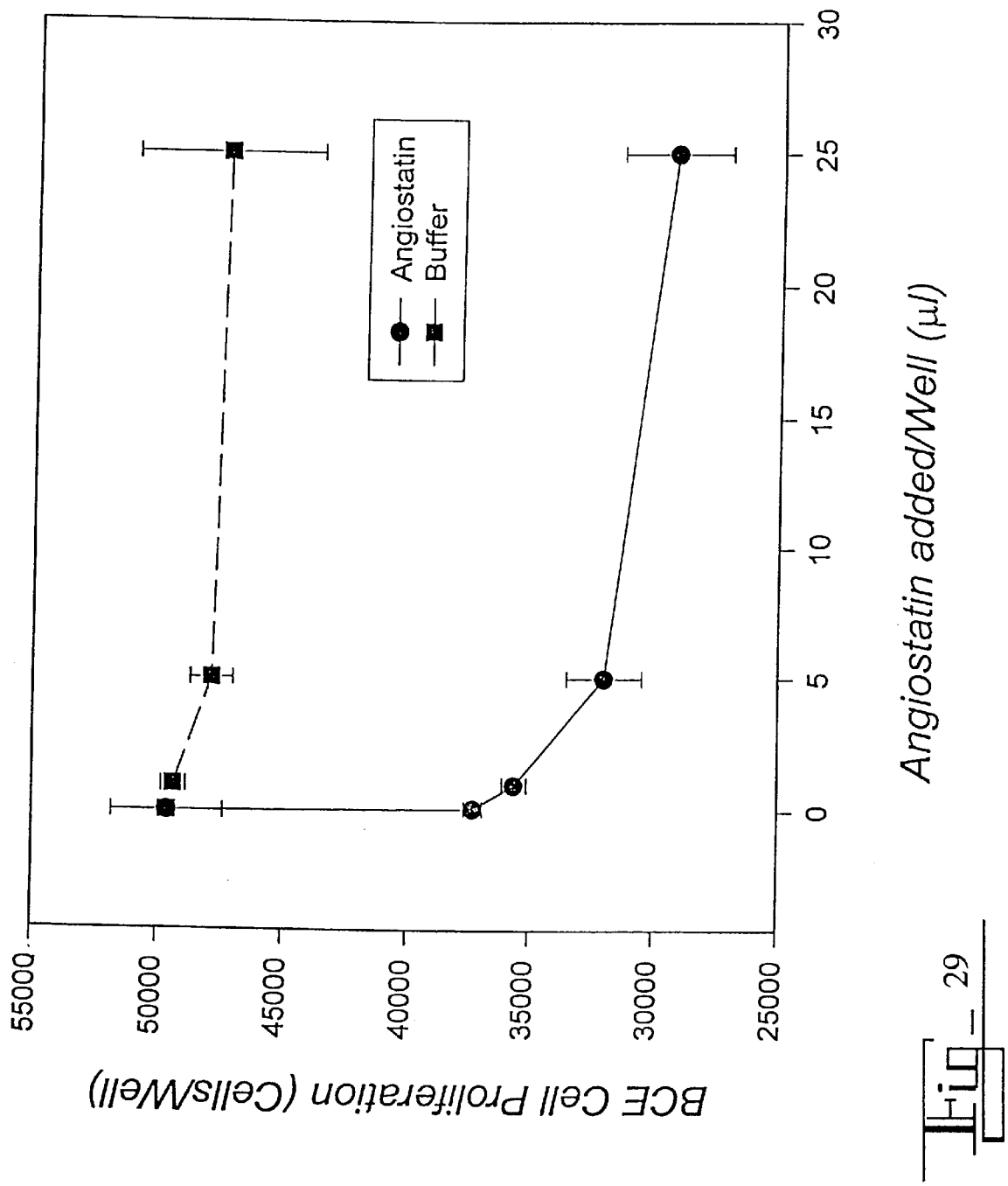
FIG. 29 shows the effect of administering aggregate recombinant mouse angiostatin on bovine capillary endothelial cells.

Bovine capillary endothelial (BCE) cells were used in an assay as outlined in Example 8. The cells were challenged with aggregate recombinant human angiostatin prepared as described in this Example. The results are shown in FIG. 29, which reveals a significant inhibition of the endothelial cells exposed to aggregate angiostatin.

In vivo tests of aggregate angiostatin

All animal work was carried out at the animal facility of Children's Hospital in accordance with institutional guidelines. A. The aggregate recombinant mouse angiostatin, prepared as described in this Example, was tested with the chick CAM assay. (O'Reilly, M. S., Holmgren, L., Shing, Y., Chen, C., Rosenthal, R. A., Moses, M., Lane, W. S., Cao, Y., Sage, E. H., and Folkman, J., *Cell* (1994) 79:315–328). At a dose of 25 ug, the inhibition of capillary formation was 100% (all five chick CAMs tested gave 2–3+ inhibitory zones). At a dose of 100 ug, the inhibition of capillary formation lasted for 96 hours. The effect of other angiogenesis inhibitors and plasminogen derived angiostatin are known to last about 48 hours. This suggests that the aggregate angiostatin provides a sustained release advantage.

B. Lewis lung carcinoma was inoculated into the subcutaneous mid-dorsum of C57B16 mice. Mice were implanted with 1×10⁶ cells in 0.1 ml PBS prepared as previously described and caged in groups of 6 or less. Tumors were measured with a dialcaliper and tumor volumes were determined using the formula width x width x length x 0.52, and the ratio of treated to control tumor volume (T/C) was determined for the last time point.

After tumor volume was 100–200 cubic millimeters, which occurred within 3–5 days, mice were randomized for two separate experiments. In the first experiment, mice received 2–3 mg/kg of the aggregate recombinant mouse angiostatin suspension in PBS injected subcutaneously at a site distant from the tumor every 24 hours (n=3 mice/group). The control group received comparable injections of saline. In the second separate experiment (n=6 mice/group), test mice received 10 mg/kg of the aggregate recombinant mouse angiostatin suspension in PBS injected subcutaneously at a site distant from the tumor every 24 hours. The control group received comparable injections of saline.

Figure 30:
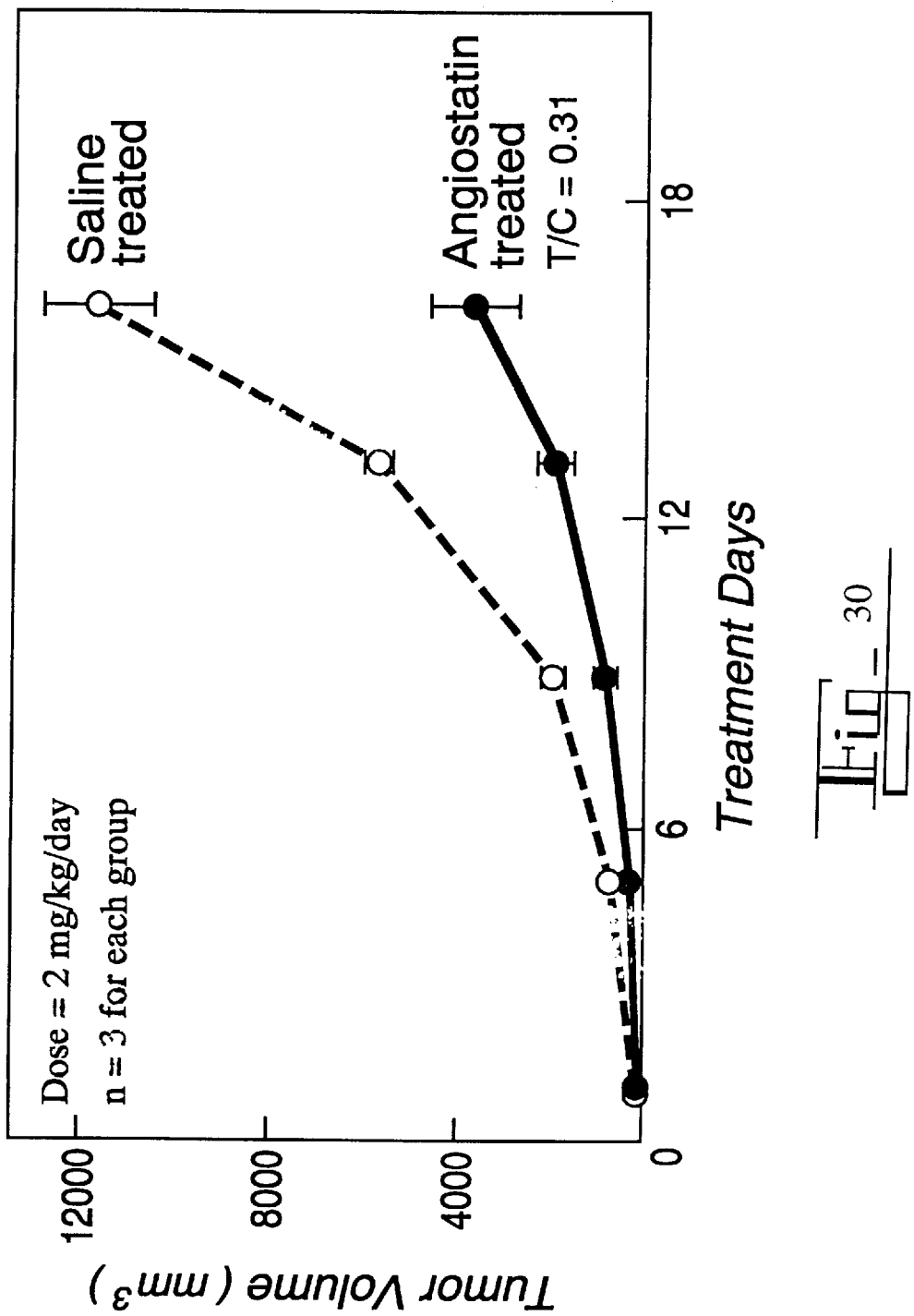
FIG. 30 shows the effect on tumor volume of administering 2 mg/kg/day aggregate angiostatin in mice innoculated with Lewis lung carcinoma.
Figure 31:
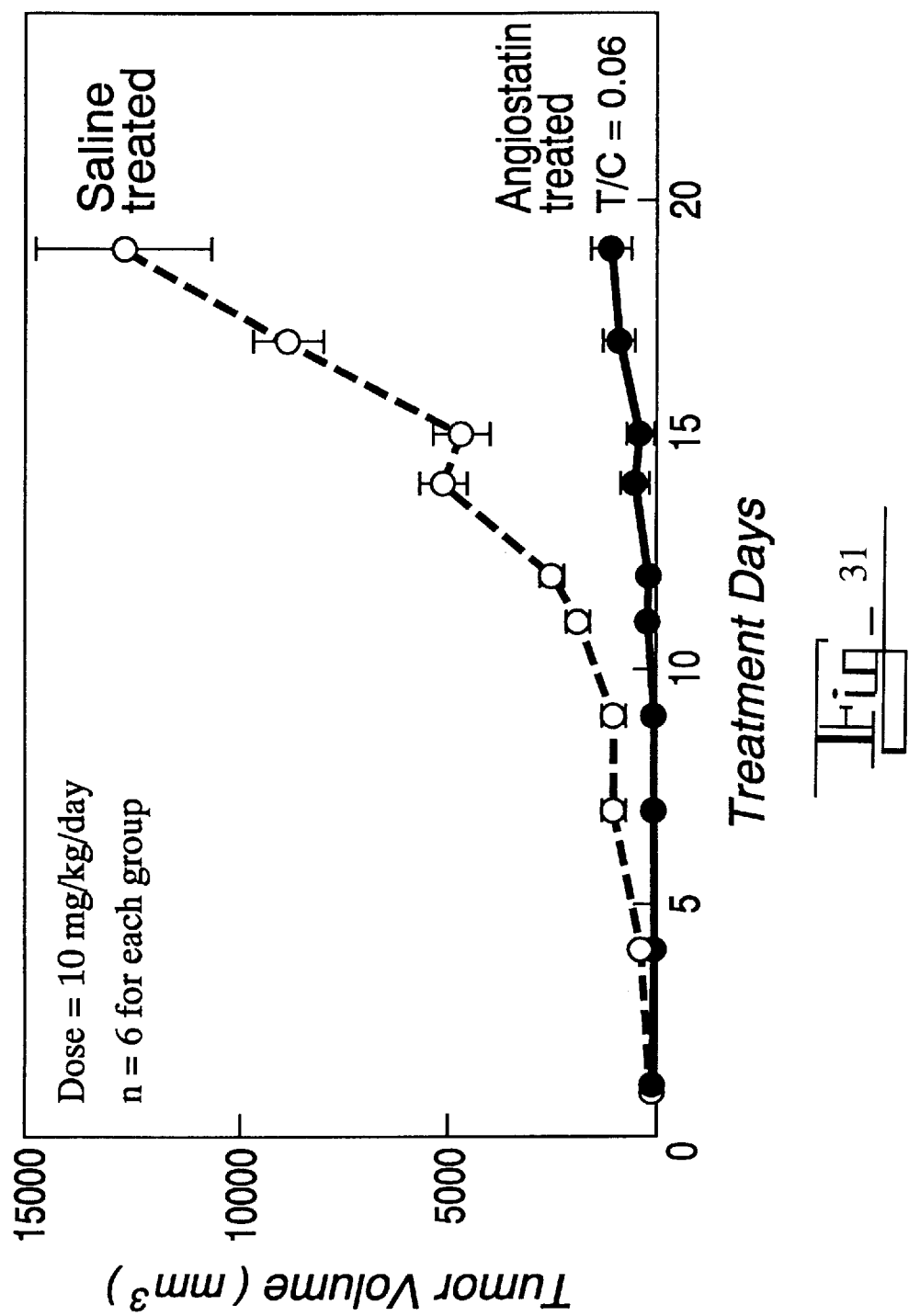
FIG. 31 shows the effect on tumor volume of administering 10 mg/kg/day aggregate angiostatin in mice innoculated with Lewis lung carcinoma.

No toxicity or weight loss was noted in any of the mice treated with the aggregated recombinant angiostatin suspension. In the mice, the aggregate angiostatin was seen as a subcutaneous mass after injection which resorbs over a period of several hours. This suggests that it was gradually being solubilized, and demonstrates that the aggregate angiostatin is an effective means of sustained release. At both doses, there was a significant inhibition of the growth of Lewis lung carcinoma primary tumors in the treated mice. See FIGS. 30 and 31. The T/C obtained by giving 10/mg/kg/day as a single injection for 19 days (when the saline control animals started to die and were sacrificed) is 0.06, which is a tumor volume reduction never before achieved to the knowledge of the inventors.

The in vitro and in vivo results of this Example provide a reasonable basis for an expectation of success for using the products and processes described for the inhibition of endothelial cell proliferation, angiogenesis, and tumor growth in humans. While not wishing to be bound by theory, the aggregate recombinant angiostatin produced by the present method may have a different conformation, and therefore different physical properties, from elastase generated angiostatin or other purified proteins that are normally renatured. Purified recombinant angiostatin was precipitated to form an aggregate suspension by dialyzing the protein solution against a relatively large volume of buffer or water. This is believed to occur because the improperly folded protein becomes insoluble and aggregated. Formerly, it would not be expected that a denatured aggregate protein would be so remarkably effective in vivo. The potent antitumoral activity demonstrated is also believed to be due to a slow but constant dissolving and releasing of the aggregate protein from the subcutaneous sites. The invention further contemplates that either naturally occurring or recombinant angiostatin, and angiostatin fragments, may be used in the described methods of purification to yield aggregate natural or recombinant angiostatin, or aggregate fragments of angiostatin, which can be used for the successful inhibition of endothelial cell proliferation and tumor growth, without the need for renaturing.

It should be understood that the foregoing relates only to preferred embodiments of the present invention, and that numerous modifications or alterations may be made therein without departing from the spirit and the scope of the invention as set forth in the appended claims. The references cited throughout are hereby incorporated by reference in their entireties.

---

We claim:

1. A composition for inhibiting endothelial cell proliferation comprising substantially purified aggregate angiostatin protein, wherein the aggregate angiostatin protein is a recombinantly produced protein which precipitates in an approximately neutral pH aqueous solution, and contains approximately a kringle 1–4 region of a plasminogen molecule.

2. The composition of claim 1, wherein the aggregate angiostatin has a molecular weight of approximately 45 to 65 kilodaltons as determined by reducing polyacrylamide gel electrophoresis.

3. The composition of claim 1, wherein the aggregate angiostatin is derived from a plasminogen fragment beginning at approximately amino acid number 98 derived from human plasminogen, murine plasminogen, bovine plasminogen, Rhesus plasminogen or porcine plasminogen.

4. The composition of claim 3, wherein the aggregate angiostatin is selected from the group consisting of SEQ ID NO:2, SEQ ID NO:3, SEQ ID NO:4, SEQ ID NO:5, and SEQ ID NO:6.

5. The composition of claim 1, wherein the aggregate angiostatin is derived from recombinant angiostatin.

6. The composition of claim 1, wherein the aggregate angiostatin is capable of inhibiting an angiogenesis-mediated disease.

7. The composition of claim 6, wherein the disease is selected from the group consisting of cancer, arthritis, macular degeneration and diabetic retinopathy.

8. A method of inhibiting endothelial cell proliferation comprising administering to the endothelial cell a proliferation inhibiting amount of aggregate angiostatin protein, wherein the aggregate angiostatin protein is a recombinantly produced protein which precipitates in an approximately neutral pH aqueous solution and contains approximately a kringle 1–4 region of a plasminogen molecule.

9. The method of claim 8, wherein the aggregate angiostatin has a molecular weight of approximately 45 to 65 kilodaltons as determined by reducing polyacrylamide gel electrophoresis.

10. The method of claim 8, wherein the amino aggregate angiostatin is derived from a plasminogen fragment beginning at approximately amino acid number 98 derived from human plasminogen, murine plasminogen, bovine plasminogen, Rhesus plasminogen or porcine plasminogen.

11. The method of claim 10, wherein the aggregate angiostatin is selected from the group consisting of SEQ ID NO:2, SEQ ID NO:3, SEQ ID NO:4, SEQ ID NO:5, and SEQ ID NO:6.

12. The method of claim 8, wherein the aggregate angiostatin is derived from recombinant angiostatin.

13. The method of claim 8, wherein the aggregate angiostatin is capable of inhibiting the angiogenesis-mediated diseases.

14. The method of claim 13, wherein the angiogenesis-mediated disease is selected from the group consisting of cancer, arthritis, macular degeneration and diabetic retinopathy.

15. A method of treating a mammal with an angiogenic-mediated disease comprising administering to the mammal an angiogenic-mediated disease treatment effective amount of aggregate angiostatin protein, wherein the aggregate angiostatin protein is a recombinantly produced protein which precipitates in an approximately neutral pH aqueous solution and contains approximately a kringle 1–4 region of a plasminogen molecule.

16. The method of claim 15, wherein angiostatin is a protein having a molecular weight of approximately 45 to 65 kilodaltons as determined by reducing polyacrylamide gel electrophoresis.

17. The method of claim 15, wherein the aggregate angiostatin is derived from a plasminogen fragment beginning at amino acid number 98 derived from human plasminogen, murine plasminogen, bovine plasminogen, Rhesus plasminogen or porcine plasminogen.

18. The method of claim 17, wherein the aggregate angiostatin is selected from the group consisting of SEQ ID NO:2, SEQ ID NO:3, SEQ ID NO:4, SEQ ID NO:5, and SEQ ID NO:6.

19. The method of claim 15, wherein the angiogenic-mediated disease is selected from the group consisting of cancer, arthritis, macular degeneration and diabetic retinopathy.

20. A method of producing aggregate angiostatin protein for inhibiting endothelial cell proliferation, wherein the aggregate angiostatin protein is a recombinantly produced protein which precipitates in an approximately neutral pH aqueous solution and contains approximately a kringle 1–4 region of a plasminogen molecule, comprising, recombinantly expressing angiostatin protein, substantially purifying angiostatin protein, and aggregating the purified angiostatin protein by precipitation.

21. The method of claim 20, wherein the aggregating step is performed by dialyzing the angiostatin.

22. The method of claim 21, wherein the dialyzing step is performed for approximately 24 hours with at least three changes of the dialysate.

23. The method of claim 22, wherein the dialyzing step is performed at approximately 4° C.

24. The method of claim 20, wherein the aggregate angiostatin is derived from recombinant angiostatin.

25. The method of claim 24, wherein the recombinant angiostatin comprises an oligohistidine portion, and the purification step is performed using a nickel affinity chromatography column.

26. The method of claim 20, wherein aggregate angiostatin has a molecular weight of approximately 45 to 65 kilodaltons as determined by reducing polyacrylamide gel electrophoresis.

27. A product made by the process of claim 20.

28. A composition comprising aggregate angiostatin and a pharmaceutically acceptable excipient.

29. The composition of claim 28, further comprising a sustained-release matrix.

30. The composition of claim 28, wherein the aggregate angiostatin has a molecular weight of approximately 45 to 55 kilodaltons as determined by reducing polyacrylamide gel electrophoresis.

* * * * *

UNITED STATES PATENT AND TRADEMARK OFFICE
CERTIFICATE OF CORRECTION

PATENT NO. : 5,861,372

DATED : January 19, 1999

INVENTOR(S) : Folkman et al.

It is certified that error appears in the above-identified patent and that said Letters Patent is hereby corrected as shown below:

Column 1, line 3, insert the following:

--This invention was made with government support under Grant No.(s) RO1-CA644-81 by the National Institutes of Health. The government may have certain rights in the invention.--

Signed and Sealed this

Twenty-eighth Day of March, 2000

*Attest:*

Q. TODD DICKINSON

*Attesting Officer*  Commissioner of Patents and Trademarks

UNITED STATES PATENT AND TRADEMARK OFFICE
CERTIFICATE OF CORRECTION

PATENT NO. : 5,861,372
DATED : January 19, 1999
INVENTOR(S) : Folkman et al.

It is certified that error appears in the above-identified patent and that said Letters Patent is hereby corrected as shown below:

Column 1,
Line 3, of the specification, please insert the following:
-- This invention was made with goverment support under Grant No. (s) CA45548 by the National Institutes of Health. The government may have certain rights in the invention. --

Signed and Sealed this

Thirtieth Day of October, 2001

Attest:

NICHOLAS P. GODICI
Attesting Officer    Acting Director of the United States Patent and Trademark Office

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 812 amino acids
        ( B ) TYPE: amino acid
        ( C ) STRANDEDNESS:
        ( D ) TOPOLOGY: linear ( i i ) MOLECULE TYPE: peptide ( v i ) ORIGINAL SOURCE:
        ( A ) ORGANISM: Murine Plasminogen ( x i ) SEQUENCE DESCRIPTION: SEQ ID NO:1:

| Met | Asp | His | Lys | Glu | Val | Ile | Leu | Leu | Phe | Leu | Leu | Leu | Leu | Lys | Pro |
|---|---|---|---|---|---|---|---|---|---|---|---|---|---|---|---|
| 1 | | | | 5 | | | | | 10 | | | | | 15 | |
| Gly | Gln | Gly | Asp | Ser | Leu | Asp | Gly | Tyr | Ile | Ser | Thr | Gln | Gly | Ala | Ser |
| | | | 20 | | | | | 25 | | | | | 30 | | |
| Leu | Phe | Ser | Leu | Thr | Lys | Lys | Gln | Leu | Ala | Ala | Gly | Gly | Val | Ser | Asp |
| | | 35 | | | | | 40 | | | | | 45 | | | |
| Cys | Leu | Ala | Lys | Cys | Glu | Gly | Glu | Thr | Asp | Phe | Val | Cys | Arg | Ser | Phe |
| | 50 | | | | | 55 | | | | | 60 | | | | |
| Gln | Tyr | His | Ser | Lys | Glu | Gln | Gln | Cys | Val | Ile | Met | Ala | Glu | Asn | Ser |
| 65 | | | | | 70 | | | | | 75 | | | | | 80 |
| Lys | Thr | Ser | Ser | Ile | Ile | Arg | Met | Arg | Asp | Val | Ile | Leu | Phe | Glu | Lys |
| | | | | 85 | | | | | 90 | | | | | 95 | |
| Arg | Val | Tyr | Leu | Ser | Glu | Cys | Lys | Thr | Gly | Ile | Gly | Asn | Gly | Tyr | Arg |
| | | | 100 | | | | | 105 | | | | | 110 | | |
| Gly | Thr | Met | Ser | Arg | Thr | Lys | Ser | Gly | Val | Ala | Cys | Gln | Lys | Trp | Gly |
| | | 115 | | | | | 120 | | | | | 125 | | | |
| Ala | Thr | Phe | Pro | His | Val | Pro | Asn | Tyr | Ser | Pro | Ser | Thr | His | Pro | Asn |

|     |     |     |     |     |     |     |     |     |     |     |     |     |     |     |     |
|---|---|---|---|---|---|---|---|---|---|---|---|---|---|---|---|
|     |     |     | 130 |     |     |     |     | 135 |     |     |     |     | 140 |     |     |
| Glu | Gly | Leu | Glu | Glu | Asn | Tyr | Cys | Arg | Asn | Pro | Asp | Asn | Asp | Glu | Gln |
| 145 |     |     |     |     | 150 |     |     |     |     | 155 |     |     |     |     | 160 |
| Gly | Pro | Trp | Cys | Tyr | Thr | Thr | Asp | Pro | Asp | Lys | Arg | Tyr | Asp | Tyr | Cys |
|     |     |     |     | 165 |     |     |     |     | 170 |     |     |     |     | 175 |     |
| Asn | Ile | Pro | Glu | Cys | Glu | Glu | Glu | Cys | Met | Tyr | Cys | Ser | Gly | Glu | Lys |
|     |     |     | 180 |     |     |     |     | 185 |     |     |     |     | 190 |     |     |
| Tyr | Glu | Gly | Lys | Ile | Ser | Lys | Thr | Met | Ser | Gly | Leu | Asp | Cys | Gln | Ala |
|     |     | 195 |     |     |     |     | 200 |     |     |     |     | 205 |     |     |     |
| Trp | Asp | Ser | Gln | Ser | Pro | His | Ala | His | Gly | Tyr | Ile | Pro | Ala | Lys | Phe |
|     | 210 |     |     |     |     | 215 |     |     |     |     | 220 |     |     |     |     |
| Pro | Ser | Lys | Asn | Leu | Lys | Met | Asn | Tyr | Cys | His | Asn | Pro | Asp | Gly | Glu |
| 225 |     |     |     |     | 230 |     |     |     |     | 235 |     |     |     |     | 240 |
| Pro | Arg | Pro | Trp | Cys | Phe | Thr | Thr | Asp | Pro | Thr | Lys | Arg | Trp | Glu | Tyr |
|     |     |     |     | 245 |     |     |     |     | 250 |     |     |     |     | 255 |     |
| Cys | Asp | Ile | Pro | Arg | Cys | Thr | Thr | Pro | Pro | Pro | Pro | Ser | Pro | Ser | Thr |
|     |     |     | 260 |     |     |     |     | 265 |     |     |     |     | 270 |     |     |
| Tyr | Gln | Cys | Leu | Lys | Gly | Arg | Gly | Glu | Asn | Tyr | Arg | Gly | Thr | Val | Ser |
|     |     | 275 |     |     |     |     | 280 |     |     |     |     | 285 |     |     |     |
| Val | Thr | Val | Ser | Gly | Lys | Thr | Cys | Gln | Arg | Trp | Ser | Glu | Gln | Thr | Pro |
|     | 290 |     |     |     |     | 295 |     |     |     |     | 300 |     |     |     |     |
| His | Arg | His | Asn | Arg | Thr | Pro | Glu | Asn | Phe | Pro | Cys | Lys | Asn | Leu | Glu |
| 305 |     |     |     |     | 310 |     |     |     |     | 315 |     |     |     |     | 320 |
| Glu | Asn | Tyr | Cys | Arg | Asn | Pro | Asp | Gly | Glu | Thr | Ala | Pro | Trp | Cys | Tyr |
|     |     |     |     | 325 |     |     |     |     | 330 |     |     |     |     | 335 |     |
| Thr | Thr | Asp | Ser | Gln | Leu | Arg | Trp | Glu | Tyr | Cys | Glu | Ile | Pro | Ser | Cys |
|     |     |     | 340 |     |     |     |     | 345 |     |     |     |     | 350 |     |     |
| Glu | Ser | Ser | Ala | Ser | Pro | Asp | Gln | Ser | Asp | Ser | Ser | Val | Pro | Pro | Glu |
|     |     | 355 |     |     |     |     | 360 |     |     |     |     | 365 |     |     |     |
| Glu | Gln | Thr | Pro | Val | Val | Gln | Glu | Cys | Tyr | Gln | Ser | Asp | Gly | Gln | Ser |
|     | 370 |     |     |     |     | 375 |     |     |     |     | 380 |     |     |     |     |
| Tyr | Arg | Gly | Thr | Ser | Ser | Thr | Thr | Ile | Thr | Gly | Lys | Lys | Cys | Gln | Ser |
| 385 |     |     |     |     | 390 |     |     |     |     | 395 |     |     |     |     | 400 |
| Trp | Ala | Ala | Met | Phe | Pro | His | Arg | His | Ser | Lys | Thr | Pro | Glu | Asn | Phe |
|     |     |     |     | 405 |     |     |     |     | 410 |     |     |     |     | 415 |     |
| Pro | Asp | Ala | Gly | Leu | Glu | Met | Asn | Tyr | Cys | Arg | Asn | Pro | Asp | Gly | Asp |
|     |     |     | 420 |     |     |     |     | 425 |     |     |     |     | 430 |     |     |
| Lys | Gly | Pro | Trp | Cys | Tyr | Thr | Thr | Asp | Pro | Ser | Val | Arg | Trp | Glu | Tyr |
|     |     | 435 |     |     |     |     | 440 |     |     |     |     | 445 |     |     |     |
| Cys | Asn | Leu | Lys | Arg | Cys | Ser | Glu | Thr | Gly | Gly | Ser | Val | Val | Glu | Leu |
|     | 450 |     |     |     |     | 455 |     |     |     |     | 460 |     |     |     |     |
| Pro | Thr | Val | Ser | Gln | Glu | Pro | Ser | Gly | Pro | Ser | Asp | Ser | Glu | Thr | Asp |
| 465 |     |     |     |     | 470 |     |     |     |     | 475 |     |     |     |     | 480 |
| Cys | Met | Tyr | Gly | Asn | Gly | Lys | Asp | Tyr | Arg | Gly | Lys | Thr | Ala | Val | Thr |
|     |     |     |     | 485 |     |     |     |     | 490 |     |     |     |     | 495 |     |
| Ala | Ala | Gly | Thr | Pro | Cys | Gln | Gly | Trp | Ala | Ala | Gln | Glu | Pro | His | Arg |
|     |     |     | 500 |     |     |     |     | 505 |     |     |     |     | 510 |     |     |
| His | Ser | Ile | Phe | Thr | Pro | Gln | Thr | Asn | Pro | Arg | Ala | Asp | Leu | Glu | Lys |
|     |     | 515 |     |     |     |     | 520 |     |     |     |     | 525 |     |     |     |
| Asn | Tyr | Cys | Arg | Asn | Pro | Asp | Gly | Asp | Val | Asn | Gly | Pro | Trp | Cys | Tyr |
|     | 530 |     |     |     |     | 535 |     |     |     |     | 540 |     |     |     |     |
| Thr | Thr | Asn | Pro | Arg | Lys | Leu | Tyr | Asp | Tyr | Cys | Asp | Ile | Pro | Leu | Cys |
| 545 |     |     |     |     | 550 |     |     |     |     | 555 |     |     |     |     | 560 |

```
Ala  Ser  Ala  Ser  Ser  Phe  Glu  Cys  Gly  Lys  Pro  Gln  Val  Glu  Pro  Lys
               565                570                     575

Lys  Cys  Pro  Gly  Arg  Val  Val  Gly  Gly  Cys  Val  Ala  Asn  Pro  His  Ser
               580                585                     590

Trp  Pro  Trp  Gln  Ile  Ser  Leu  Arg  Thr  Arg  Phe  Thr  Gly  Gln  His  Phe
               595                600                     605

Cys  Gly  Gly  Thr  Leu  Ile  Ala  Pro  Glu  Trp  Val  Leu  Thr  Ala  Ala  His
     610                          615                     620

Cys  Leu  Glu  Lys  Ser  Ser  Arg  Pro  Glu  Phe  Tyr  Lys  Val  Ile  Leu  Gly
625                      630                635                          640

Ala  His  Glu  Glu  Tyr  Ile  Arg  Gly  Leu  Asp  Val  Gln  Glu  Ile  Ser  Val
                    645                     650                     655

Ala  Lys  Leu  Ile  Leu  Glu  Pro  Asn  Asn  Arg  Asp  Ile  Ala  Leu  Leu  Lys
                    660                     665                670

Leu  Ser  Arg  Pro  Ala  Thr  Ile  Thr  Asp  Lys  Val  Ile  Pro  Ala  Cys  Leu
          675                     680                     685

Pro  Ser  Pro  Asn  Tyr  Met  Val  Ala  Asp  Arg  Thr  Ile  Cys  Tyr  Ile  Thr
          690                695                     700

Gly  Trp  Gly  Glu  Thr  Gln  Gly  Thr  Phe  Gly  Ala  Gly  Arg  Leu  Lys  Glu
705                           710                715                          720

Ala  Gln  Leu  Pro  Val  Ile  Glu  Asn  Lys  Val  Cys  Asn  Arg  Val  Glu  Tyr
               725                     730                          735

Leu  Asn  Asn  Arg  Val  Lys  Ser  Thr  Glu  Leu  Cys  Ala  Gly  Gln  Leu  Ala
               740                     745                     750

Gly  Gly  Val  Asp  Ser  Cys  Gln  Gly  Asp  Ser  Gly  Gly  Pro  Leu  Val  Cys
          755                     760                     765

Phe  Glu  Lys  Asp  Lys  Tyr  Ile  Leu  Gln  Gly  Val  Thr  Ser  Trp  Gly  Leu
     770                     775                     780

Gly  Cys  Ala  Arg  Pro  Asn  Lys  Pro  Gly  Val  Tyr  Val  Arg  Val  Ser  Arg
785                     790                     795                          800

Phe  Val  Asp  Trp  Ile  Glu  Arg  Glu  Met  Arg  Asn  Asn
                    805                     810
```

( 2 ) INFORMATION FOR SEQ ID NO:2:

( i ) SEQUENCE CHARACTERISTICS:
        ( A ) LENGTH: 339 amino acids
        ( B ) TYPE: amino acid
        ( C ) STRANDEDNESS:
        ( D ) TOPOLOGY: linear ( i i ) MOLECULE TYPE: peptide ( v i ) ORIGINAL SOURCE:
        ( A ) ORGANISM: Murine Angiostatin ( x i ) SEQUENCE DESCRIPTION: SEQ ID NO:2:

```
Val  Tyr  Leu  Ser  Glu  Cys  Lys  Thr  Gly  Ile  Gly  Asn  Gly  Tyr  Arg  Gly
1                   5                   10                          15

Thr  Met  Ser  Arg  Thr  Lys  Ser  Gly  Val  Ala  Cys  Gln  Lys  Trp  Gly  Ala
               20                     25                          30

Thr  Phe  Pro  His  Val  Pro  Asn  Tyr  Ser  Pro  Ser  Thr  His  Pro  Asn  Glu
               35                     40                     45

Gly  Leu  Glu  Glu  Asn  Tyr  Cys  Arg  Asn  Pro  Asp  Asn  Asp  Glu  Gln  Gly
     50                     55                     60

Pro  Trp  Cys  Tyr  Thr  Thr  Asp  Pro  Asp  Lys  Arg  Tyr  Asp  Tyr  Cys  Asn
65                      70                     75                          80

Ile  Pro  Glu  Cys  Glu  Glu  Glu  Cys  Met  Tyr  Cys  Ser  Gly  Glu  Lys  Tyr
```

-continued

| | | | | 85 | | | | | 90 | | | | | 95 | |
|---|---|---|---|---|---|---|---|---|---|---|---|---|---|---|---|
| Glu | Gly | Lys | Ile | Ser | Lys | Thr | Met | Ser | Gly | Leu | Asp | Cys | Gln | Ala | Trp |
| | | | 100 | | | | | 105 | | | | | 110 | | |
| Asp | Ser | Gln | Ser | Pro | His | Ala | His | Gly | Tyr | Ile | Pro | Ala | Lys | Phe | Pro |
| | | 115 | | | | | 120 | | | | | 125 | | | |
| Ser | Lys | Asn | Leu | Lys | Met | Asn | Tyr | Cys | His | Asn | Pro | Asp | Gly | Glu | Pro |
| | 130 | | | | | 135 | | | | | 140 | | | | |
| Arg | Pro | Trp | Cys | Phe | Thr | Thr | Asp | Pro | Thr | Lys | Arg | Trp | Glu | Tyr | Cys |
| 145 | | | | | 150 | | | | | 155 | | | | | 160 |
| Asp | Ile | Pro | Arg | Cys | Thr | Thr | Pro | Pro | Pro | Pro | Ser | Pro | Thr | Tyr | |
| | | | | 165 | | | | | 170 | | | | | 175 | |
| Gln | Cys | Leu | Lys | Gly | Arg | Gly | Glu | Asn | Tyr | Arg | Gly | Thr | Val | Ser | Val |
| | | | 180 | | | | | 185 | | | | | 190 | | |
| Thr | Val | Ser | Gly | Lys | Thr | Cys | Gln | Arg | Trp | Ser | Glu | Gln | Thr | Pro | His |
| | | 195 | | | | | 200 | | | | | 205 | | | |
| Arg | His | Asn | Arg | Thr | Pro | Glu | Asn | Phe | Pro | Cys | Lys | Asn | Leu | Glu | Glu |
| | 210 | | | | | 215 | | | | | 220 | | | | |
| Asn | Tyr | Cys | Arg | Asn | Pro | Asp | Gly | Glu | Thr | Ala | Pro | Trp | Cys | Tyr | Thr |
| 225 | | | | | 230 | | | | | 235 | | | | | 240 |
| Thr | Asp | Ser | Gln | Leu | Arg | Trp | Glu | Tyr | Cys | Glu | Ile | Pro | Ser | Cys | Glu |
| | | | | 245 | | | | | 250 | | | | | 255 | |
| Ser | Ser | Ala | Ser | Pro | Asp | Gln | Ser | Asp | Ser | Ser | Val | Pro | Pro | Glu | Glu |
| | | | 260 | | | | | 265 | | | | | 270 | | |
| Gln | Thr | Pro | Val | Val | Gln | Glu | Cys | Tyr | Gln | Ser | Asp | Gly | Gln | Ser | Tyr |
| | | 275 | | | | | 280 | | | | | 285 | | | |
| Arg | Gly | Thr | Ser | Ser | Thr | Thr | Ile | Thr | Gly | Lys | Lys | Cys | Gln | Ser | Trp |
| | 290 | | | | | 295 | | | | | 300 | | | | |
| Ala | Ala | Met | Phe | Pro | His | Arg | His | Ser | Lys | Thr | Pro | Glu | Asn | Phe | Pro |
| 305 | | | | | 310 | | | | | 315 | | | | | 320 |
| Asp | Ala | Gly | Leu | Glu | Met | Asn | Tyr | Cys | Arg | Asn | Pro | Asp | Gly | Asp | Lys |
| | | | | 325 | | | | | 330 | | | | | 335 | |
| Gly | Pro | Trp | | | | | | | | | | | | | |

( 2 ) INFORMATION FOR SEQ ID NO:3:

( i ) SEQUENCE CHARACTERISTICS:
        ( A ) LENGTH: 339 amino acids
        ( B ) TYPE: amino acid
        ( C ) STRANDEDNESS:
        ( D ) TOPOLOGY: linear ( i i ) MOLECULE TYPE: peptide ( v i ) ORIGINAL SOURCE:
        ( A ) ORGANISM: Human Angiostatin ( x i ) SEQUENCE DESCRIPTION: SEQ ID NO:3:

| Val | Tyr | Leu | Ser | Glu | Cys | Lys | Thr | Gly | Asn | Gly | Lys | Asn | Tyr | Arg | Gly |
|---|---|---|---|---|---|---|---|---|---|---|---|---|---|---|---|
| 1 | | | | 5 | | | | | 10 | | | | | 15 | |
| Thr | Met | Ser | Lys | Thr | Lys | Asn | Gly | Ile | Thr | Cys | Gln | Lys | Trp | Ser | Ser |
| | | | 20 | | | | | 25 | | | | | 30 | | |
| Thr | Ser | Pro | His | Arg | Pro | Arg | Phe | Ser | Pro | Ala | Thr | His | Pro | Ser | Glu |
| | | 35 | | | | | 40 | | | | | 45 | | | |
| Gly | Leu | Glu | Glu | Asn | Tyr | Cys | Arg | Asn | Pro | Asp | Asn | Asp | Pro | Gln | Gly |
| | 50 | | | | | 55 | | | | | 60 | | | | |
| Pro | Trp | Cys | Tyr | Thr | Thr | Asp | Pro | Glu | Lys | Arg | Tyr | Asp | Tyr | Cys | Asp |
| 65 | | | | | 70 | | | | | 75 | | | | | 80 |

-continued

| | | | | | | | | | | | | | | |
|---|---|---|---|---|---|---|---|---|---|---|---|---|---|---|
|Ile|Leu|Glu|Cys|Glu 85|Glu|Cys|Met|His 90|Cys|Ser|Gly|Glu|Asn|Tyr 95|
|Asp|Gly|Lys|Ile 100|Ser|Lys|Thr|Met|Ser 105|Gly|Leu|Glu|Cys|Gln 110|Ala|Trp|
|Asp|Ser|Gln 115|Ser|Pro|His|Ala|His 120|Gly|Tyr|Ile|Pro|Ser 125|Lys|Phe|Pro|
|Asn|Lys 130|Asn|Leu|Lys|Lys|Asn 135|Tyr|Cys|Arg|Asn|Pro 140|Asp|Arg|Glu|Leu|
|Arg 145|Pro|Trp|Cys|Phe|Thr 150|Thr|Asp|Pro|Asn|Lys 155|Arg|Trp|Glu|Leu|Cys 160|
|Asp|Ile|Pro|Arg|Cys 165|Thr|Thr|Pro|Pro|Pro 170|Ser|Ser|Gly|Pro|Thr 175|Tyr|
|Gln|Cys|Leu|Lys 180|Gly|Thr|Gly|Glu|Asn 185|Tyr|Arg|Gly|Asn|Val 190|Ala|Val|
|Thr|Val|Ser 195|Gly|His|Thr|Cys|Gln 200|His|Trp|Ser|Ala|Gln 205|Thr|Pro|His|
|Thr|His 210|Asn|Arg|Thr|Pro|Glu 215|Asn|Phe|Pro|Cys|Lys 220|Asn|Leu|Asp|Glu|
|Asn 225|Tyr|Cys|Arg|Asn|Pro 230|Asp|Gly|Lys|Arg|Ala 235|Pro|Trp|Cys|His|Thr 240|
|Thr|Asn|Ser|Gln|Val 245|Arg|Trp|Glu|Tyr|Cys 250|Lys|Ile|Pro|Ser|Cys 255|Asp|
|Ser|Ser|Pro|Val 260|Ser|Thr|Glu|Gln|Leu 265|Ala|Pro|Thr|Ala|Pro 270|Pro|Glu|
|Leu|Thr|Pro 275|Val|Val|Gln|Asp|Cys 280|Tyr|His|Gly|Asp|Gly 285|Gln|Ser|Tyr|
|Arg|Gly 290|Thr|Ser|Ser|Thr|Thr 295|Thr|Thr|Gly|Lys|Lys 300|Cys|Gln|Ser|Trp|
|Ser 305|Ser|Met|Thr|Pro|His 310|Arg|His|Gln|Lys|Thr 315|Pro|Glu|Asn|Tyr|Pro 320|
|Asn|Ala|Gly|Leu|Thr 325|Met|Asn|Tyr|Cys|Arg 330|Asn|Pro|Asp|Ala|Asp 335|Lys|
|Gly|Pro|Trp| | | | | | | | | | | | | |

( 2 ) INFORMATION FOR SEQ ID NO:4:

( i ) SEQUENCE CHARACTERISTICS:
        ( A ) LENGTH: 339 amino acids
        ( B ) TYPE: amino acid
        ( C ) STRANDEDNESS:
        ( D ) TOPOLOGY: linear ( i i ) MOLECULE TYPE: peptide ( v i ) ORIGINAL SOURCE:
        ( A ) ORGANISM: Rhesus Angiostatin ( x i ) SEQUENCE DESCRIPTION: SEQ ID NO:4:

| | | | | | | | | | | | | | | |
|---|---|---|---|---|---|---|---|---|---|---|---|---|---|---|
|Val 1|Tyr|Leu|Ser|Glu 5|Cys|Lys|Thr|Gly|Asn 10|Gly|Lys|Asn|Tyr|Arg 15|Gly|
|Thr|Met|Ser|Lys 20|Thr|Arg|Thr|Gly|Ile 25|Thr|Cys|Gln|Lys|Trp 30|Ser|Ser|
|Thr|Ser|Pro 35|His|Arg|Pro|Thr|Phe 40|Ser|Pro|Ala|Thr|His 45|Pro|Ser|Glu|
|Gly|Leu|Glu 50|Glu|Asn|Tyr|Cys|Arg 55|Asn|Pro|Asp|Asn|Asp 60|Gly|Gln|Gly|
|Pro 65|Trp|Cys|Tyr|Thr|Thr 70|Asp|Pro|Glu|Glu|Arg 75|Phe|Asp|Tyr|Cys|Asp 80|

|       |       |       |       |       |       |       |       |       |       |       |       |       |       |       |
|-------|-------|-------|-------|-------|-------|-------|-------|-------|-------|-------|-------|-------|-------|-------|
| Ile   | Pro   | Glu   | Cys   | Glu   | Asp   | Glu   | Cys   | Met   | His   | Cys   | Ser   | Gly   | Glu   | Asn   | Tyr |
|       |       |       |       | 85    |       |       |       |       | 90    |       |       |       |       | 95    |

Asp Gly Lys Ile Ser Lys Thr Met Ser Gly Leu Glu Cys Gln Ala Trp
                100                 105                 110

Asp Ser Gln Ser Pro His Ala His Gly Tyr Ile Pro Ser Lys Phe Pro
                115             120                 125

Asn Lys Asn Leu Lys Lys Asn Tyr Cys Arg Asn Pro Asp Gly Glu Pro
    130             135                 140

Arg Pro Trp Cys Phe Thr Thr Asp Pro Asn Lys Arg Trp Glu Leu Cys
145                 150                 155                 160

Asp Ile Pro Arg Cys Thr Thr Pro Pro Ser Ser Gly Pro Thr Tyr
                165                 170                 175

Gln Cys Leu Lys Gly Thr Gly Glu Asn Tyr Arg Gly Asp Val Ala Val
            180                 185                 190

Thr Val Ser Gly His Thr Cys His Gly Trp Ser Ala Gln Thr Pro His
        195                 200                 205

Thr His Asn Arg Thr Pro Glu Asn Phe Pro Cys Lys Asn Leu Asp Glu
    210                 215                 220

Asn Tyr Cys Arg Asn Pro Asp Gly Glu Lys Ala Pro Trp Cys Tyr Thr
225                 230                 235                 240

Thr Asn Ser Gln Val Arg Trp Glu Tyr Cys Lys Ile Pro Ser Cys Glu
                245                 250                 255

Ser Ser Pro Val Ser Thr Glu Pro Leu Asp Pro Thr Ala Pro Pro Glu
            260                 265                 270

Leu Thr Pro Val Val Gln Glu Cys Tyr His Gly Asp Gly Gln Ser Tyr
        275                 280                 285

Arg Gly Thr Ser Ser Thr Thr Thr Gly Lys Lys Cys Gln Ser Trp
    290                 295                 300

Ser Ser Met Thr Pro His Trp His Glu Lys Thr Pro Glu Asn Phe Pro
305                 310                 315                 320

Asn Ala Gly Leu Thr Met Asn Tyr Cys Arg Asn Pro Asp Ala Asp Lys
                325                 330                 335

Gly Pro Trp ( 2 ) INFORMATION FOR SEQ ID NO:5:

( i ) SEQUENCE CHARACTERISTICS:
        ( A ) LENGTH: 339 amino acids
        ( B ) TYPE: amino acid
        ( C ) STRANDEDNESS:
        ( D ) TOPOLOGY: linear ( i i ) MOLECULE TYPE: peptide ( v i ) ORIGINAL SOURCE:
        ( A ) ORGANISM: Porcine Angiostatin ( x i ) SEQUENCE DESCRIPTION: SEQ ID NO:5:

Ile Tyr Leu Ser Glu Cys Lys Thr Gly Asn Gly Lys Asn Tyr Arg Gly
1               5                   10                  15

Thr Thr Ser Lys Thr Lys Ser Gly Val Ile Cys Gln Lys Trp Ser Val
            20                  25                  30

Ser Ser Pro His Ile Pro Lys Tyr Ser Pro Glu Lys Phe Pro Leu Ala
        35                  40                  45

Gly Leu Glu Glu Asn Tyr Cys Arg Asn Pro Asp Asn Asp Glu Lys Gly
    50                  55                  60

Pro Trp Cys Tyr Thr Thr Asp Pro Glu Thr Arg Phe Asp Tyr Cys Asp

|  |  |  |  |  |  |  |  |  |  |  |  |  |  |  |  |
|---|---|---|---|---|---|---|---|---|---|---|---|---|---|---|---|
| 65 | | | | 70 | | | | 75 | | | | 80 | | | |
| Ile | Pro | Glu | Cys | Glu 85 | Asp | Glu | Cys | Met | His 90 | Cys | Ser | Gly | Glu | His 95 | Tyr |
| Glu | Gly | Lys | Ile 100 | Ser | Lys | Thr | Met | Ser 105 | Gly | Ile | Glu | Cys | Gln 110 | Ser | Trp |
| Gly | Ser | Gln 115 | Ser | Pro | His | Ala | His 120 | Gly | Tyr | Leu | Pro | Ser 125 | Lys | Phe | Pro |
| Asn | Lys 130 | Asn | Leu | Lys | Met | Asn 135 | Tyr | Cys | Arg | Asn | Pro 140 | Asp | Gly | Glu | Pro |
| Arg 145 | Pro | Trp | Cys | Phe | Thr 150 | Thr | Asp | Pro | Asn | Lys 155 | Arg | Trp | Glu | Phe | Cys 160 |
| Asp | Ile | Pro | Arg | Cys 165 | Thr | Thr | Pro | Pro | Thr 170 | Ser | Gly | Pro | Thr 175 | Tyr | |
| Gln | Cys | Leu | Lys 180 | Gly | Arg | Gly | Glu | Asn 185 | Tyr | Arg | Gly | Thr | Val 190 | Ser | Val |
| Thr | Ala | Ser 195 | Gly | His | Thr | Cys | Gln 200 | Arg | Trp | Ser | Ala | Gln 205 | Ser | Pro | His |
| Lys | His | Asn 210 | Arg | Thr | Pro | Glu | Asn 215 | Phe | Pro | Cys | Lys | Asn 220 | Leu | Glu | Glu |
| Asn 225 | Tyr | Cys | Arg | Asn | Pro 230 | Asp | Gly | Glu | Thr | Ala 235 | Pro | Trp | Cys | Tyr | Thr 240 |
| Thr | Asp | Ser | Glu | Val 245 | Arg | Trp | Asp | Tyr | Cys 250 | Lys | Ile | Pro | Ser | Cys 255 | Gly |
| Ser | Ser | Thr | Thr 260 | Ser | Thr | Glu | His | Leu 265 | Asp | Ala | Pro | Val | Pro 270 | Pro | Glu |
| Gln | Thr | Pro 275 | Val | Ala | Gln | Asp | Cys 280 | Tyr | Arg | Gly | Asn | Gly 285 | Glu | Ser | Tyr |
| Arg | Gly 290 | Thr | Ser | Ser | Thr 295 | Thr | Ile | Thr | Gly | Arg 300 | Lys | Cys | Gln | Ser | Trp |
| Val 305 | Ser | Met | Thr | Pro | His 310 | Arg | His | Glu | Lys | Thr 315 | Pro | Gly | Asn | Phe | Pro 320 |
| Asn | Ala | Gly | Leu | Thr 325 | Met | Asn | Tyr | Cys | Arg 330 | Asn | Pro | Asp | Ala | Asp 335 | Lys |
| Ser | Pro | Trp | | | | | | | | | | | | | |

( 2 ) INFORMATION FOR SEQ ID NO:6:

( i ) SEQUENCE CHARACTERISTICS:
    ( A ) LENGTH: 339 amino acids
    ( B ) TYPE: amino acid
    ( C ) STRANDEDNESS:
    ( D ) TOPOLOGY: linear ( i i ) MOLECULE TYPE: peptide ( v i ) ORIGINAL SOURCE:
    ( A ) ORGANISM: Bovine Angiostatin ( x i ) SEQUENCE DESCRIPTION: SEQ ID NO:6:

|  |  |  |  |  |  |  |  |  |  |  |  |  |  |  |  |
|---|---|---|---|---|---|---|---|---|---|---|---|---|---|---|---|
| Ile 1 | Tyr | Leu | Leu | Glu 5 | Cys | Lys | Thr | Gly | Asn 10 | Gly | Gln | Thr | Tyr | Arg 15 | Gly |
| Thr | Thr | Ala | Glu 20 | Thr | Lys | Ser | Gly | Val 25 | Thr | Cys | Gln | Lys | Trp 30 | Ser | Ala |
| Thr | Ser | Pro 35 | His | Val | Pro | Lys | Phe 40 | Ser | Pro | Glu | Lys | Phe 45 | Pro | Leu | Ala |
| Gly | Leu | Glu 50 | Glu | Asn | Tyr | Cys | Arg 55 | Asn | Pro | Asp | Asn | Asp 60 | Glu | Asn | Gly |

| | | | | | | | | | | | | | | |
|---|---|---|---|---|---|---|---|---|---|---|---|---|---|---|
| Pro 65 | Trp | Cys | Tyr | Thr | Thr 70 | Asp | Pro | Asp | Lys 75 | Arg | Tyr | Asp | Tyr | Cys | Asp 80 |
| Ile | Pro | Glu | Cys | Glu 85 | Asp | Lys | Cys | Met | His 90 | Cys | Ser | Gly | Glu | Asn 95 | Tyr |
| Glu | Gly | Lys | Ile 100 | Ala | Lys | Thr | Met | Ser 105 | Gly | Arg | Asp | Cys | Gln 110 | Ala | Trp |
| Asp | Ser | Gln 115 | Ser | Pro | His | Ala | His 120 | Gly | Tyr | Ile | Pro | Ser 125 | Lys | Phe | Pro |
| Asn | Lys 130 | Asn | Leu | Lys | Met | Asn 135 | Tyr | Cys | Arg | Asn | Pro 140 | Asp | Gly | Glu | Pro |
| Arg 145 | Pro | Trp | Cys | Phe | Thr 150 | Thr | Asp | Pro | Gln | Lys 155 | Arg | Trp | Glu | Phe | Cys 160 |
| Asp | Ile | Pro | Arg | Cys 165 | Thr | Thr | Pro | Pro | Pro 170 | Ser | Ser | Gly | Pro | Lys 175 | Tyr |
| Gln | Cys | Leu | Lys 180 | Gly | Thr | Gly | Lys | Asn 185 | Tyr | Gly | Gly | Thr | Val 190 | Ala | Val |
| Thr | Glu | Ser 195 | Gly | His | Thr | Cys | Gln 200 | Arg | Trp | Ser | Glu | Gln 205 | Thr | Pro | His |
| Lys | His 210 | Asn | Arg | Thr | Pro | Glu 215 | Asn | Phe | Pro | Cys | Lys 220 | Asn | Leu | Glu | Glu |
| Asn 225 | Tyr | Cys | Arg | Asn | Pro 230 | Asp | Gly | Glu | Lys | Ala 235 | Pro | Trp | Cys | Tyr | Thr 240 |
| Thr | Asn | Ser | Glu | Val 245 | Arg | Trp | Glu | Tyr | Cys 250 | Thr | Ile | Pro | Ser | Cys 255 | Glu |
| Ser | Ser | Pro | Leu 260 | Ser | Thr | Glu | Arg | Met 265 | Asp | Val | Pro | Val | Pro 270 | Pro | Glu |
| Gln | Thr | Pro 275 | Val | Pro | Gln | Asp | Cys 280 | Tyr | His | Gly | Asn | Gly 285 | Gln | Ser | Tyr |
| Arg | Gly 290 | Thr | Ser | Ser | Thr 295 | Thr | Ile | Thr | Gly | Arg | Lys 300 | Cys | Gln | Ser | Trp |
| Ser 305 | Ser | Met | Thr | Pro | His 310 | Arg | His | Leu | Lys | Thr 315 | Pro | Glu | Asn | Tyr | Pro 320 |
| Asn | Ala | Gly | Leu | Thr 325 | Met | Asn | Tyr | Cys | Arg 330 | Asn | Pro | Asp | Ala | Asp 335 | Lys |
| Ser | Pro | Trp | | | | | | | | | | | | | |